US008530411B2

(12) United States Patent
Cerf et al.

(10) Patent No.: US 8,530,411 B2
(45) Date of Patent: Sep. 10, 2013

(54) ***BACILLUS THURINGIENSIS* CRYSTAL POLYPEPTIDES, POLYNUCLEOTIDES, AND COMPOSITIONS THEREOF**

(75) Inventors: David Cerf, Palo Alto, CA (US); Ruth Cong, Palo Alto, CA (US); Michael Freeman, Burlingame, CA (US); Kevin E. McBride, Davis, CA (US); Takashi Yamamoto, Fremont, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 666 days.

(21) Appl. No.: 12/423,367

(22) Filed: Apr. 14, 2009

(65) Prior Publication Data

US 2009/0226998 A1 Sep. 10, 2009

Related U.S. Application Data

(62) Division of application No. 11/953,648, filed on Dec. 10, 2007, now Pat. No. 7,858,849.

(60) Provisional application No. 60/873,849, filed on Dec. 8, 2006.

(51) Int. Cl.
*C07K 14/325* (2006.01)

(52) U.S. Cl.
USPC .......... 514/4.5

(58) Field of Classification Search
None
See application file for complete search history.

(56) References Cited

U.S. PATENT DOCUMENTS

| | | | | |
|---|---|---|---|---|
| 5,424,409 | A | 6/1995 | Ely et al. | |
| 5,530,195 | A | 6/1996 | Kramer et al. | |
| 5,545,565 | A * | 8/1996 | De Greve et al. | 435/320.1 |
| 6,403,865 | B1 | 6/2002 | Koziel et al. | |
| 6,780,408 | B1 | 8/2004 | Bosch et al. | |
| 2004/0221334 | A1 | 11/2004 | Baum et al. | |

FOREIGN PATENT DOCUMENTS

| | | | |
|---|---|---|---|
| EP | 0 440 581 A | 8/1991 |
| WO | 95/30752 A | 11/1995 |
| WO | WO 98/15630 | 4/1998 |
| WO | 98/22595 A | 5/1998 |
| WO | WO 02/15701 A2 | 2/2002 |

OTHER PUBLICATIONS de Maagd et al, 1999, Appl. Environ. Microbiol. 65:4369-4374.*
Tounsi et al, 2003, J. Appl. Microbiol. 95:23-28.*
Aronson et al (2001, FEMS Microbiol. Lett. 195:1-8).*
De Maagd et al (2001, Trends Genet. 17:193-199).*
DeMaagd, Ruud A., et al., "*Bacillus thuringiensis* delta-endotoxin Cry1C domain III can function as a specificity determinant for *Spodoptera exigua* in different, but not all, Cry1-Cry1C hybrids", Applied and Environmental Microbiology 66(4):1559-1563 (2000). XP002480230.
Van Der Salm T., et al., "Insect resistance of transgenic plants that express modified *Bacillus thuringiensis* CryIA(b) and CryIC genes: a resistance management strategy", Plant Molecular Biology, Springer, Dordrecht, NL 26(1):51-59 (1994) XP001029215.
Whalon, M.E. et al., "*Bacillus thuringiensis*: Use and Resistance Management", In Insecticides with Novel Modes of Action, Mechanism and Application; Ishaaya, I., Deheele, D., Eds.; Springer-Verlag: New York, Chapter 7, pp. 106-137 (1998).
Angsuthanasombat, C., et al., "Directed Mutagenesis of the *Bacillus thuringiensis* Cry11A Toxin Reveals a Crucial Role in Larvicidal Activity of Arginine-136 in Helix 4," Journal of Biochemistry and Molecular Biology, 2001, vol. 34(5), p. 402-407.
Guo, H., et al., "Protein tolerance to random amino acid change," PNAS, 2004, vol. 101(25), pp. 9205-9210.
Walters, F., et al., "Ion Channel Activity of N-Terminal Fragments From CRYIA(c) Delta-Endotoxin," Biochemical and Biophysical Research Communications, 1993, vol. 196(2), pp. 921-926.
GenBank Accession No. P0A372, "Pesticidial crystal protein cryIAb (Insecticidal delta-endotoxin CryIA(b)) (Crystaline entomocidal protoxin) (130 kDa crystal protein)," 2005, 10 pages.

* cited by examiner

*Primary Examiner* — Anne Kubelik
(74) *Attorney, Agent, or Firm* — Alston & Bird LLP

(57) ABSTRACT

The present invention provides insecticidal polypeptides related to shuffled *Bacillus thuringiensis* Cry1 polypeptides. Nucleic acids encoding the polypeptides of the invention are also provided. Methods for using the polypeptides and nucleic acids of the invention to enhance resistance of plants to insect predation are encompassed.

6 Claims, 8 Drawing Sheets

Relative Activity
0
1
2
3
4
5
6
7
8
AR1
AR2
AR3
AR4
AR5
AR6
AR7
AR8
AR9
AR10
AR11
AR12
AR13
AR14
AR15
AR16
AR17
AR18
AR19
AR20
AR21
1Ab
Parent Gene
Test 1
Test 2
AR2
AR6

SEQUENCE LISTING

<160> NUMBER OF SEQ ID NOS: 36

<210> SEQ ID NO 1
<211> LENGTH: 3543
<212> TYPE: DNA
<213> ORGANISM: Artificial Sequence
<220> FEATURE:
<223> OTHER INFORMATION: Cry1 variant
<220> FEATURE:
<221> NAME/KEY: misc_feature
<222> LOCATION: (2033)..(2033)
<223> OTHER INFORMATION: n is a, c, g, or t

<400> SEQUENCE: 1

```
atgcataaca atccgaacac caatgaatgc attccttata attgtttaag taaccctgaa     60

gtagaagtat taggtggaga aagaatagaa actggttaca ccccaatcga tatttccttg    120

tcgctaacgc aatttctttt gagtgaattt gttcccggtg ctggatttgt gttaggacta    180

gttgatataa tatggggaat ttttggtccc tctcaatggg acgcatttct tgtacaaatt    240

gaacagttaa ttaaccaaag aataggggaa ttcgctagga accaagccat ttctagatta    300

gaaggactaa gcaatcttta tcaaatttac gcagaatctt ttagagagtg ggaagcagat    360

cctactaatc cagcattaag agaagagatg cgtattcaat tcaatgacat gaacagtgcc    420

cttacaaccg ctattcctct tttgcagtt caaaattatc aagttcctct tttatcagta     480

tatgttcaag ctgcaaattt acatttatca gttttgagag atgtttcagt gtttggacaa    540

aggtggggat ttgatgccgc gactatcaat agtcgttata atgatttaac taggcttatt    600

ggcaactata cagatcatgc tgtacgctgg tacaatacgg gattagagcg tgtatgggga    660

ccggattcta gagattggat aagatataat caatttagaa gagaattaac actaactgta    720

ttagatatcg tttctctatt tccgaactat gatagtagaa cgtatccaat tcgaacagtt    780

tcccaactaa caagggaagt ttatacggac ccagtattag aaaattttga tggtagtttt    840

cgaggctcgg ctcagggcat agaaggaagt attaggagtc cacatttgat ggatatactt    900

aacagtataa ccatctatac ggatgctcat agaggagaat attattggtc agggcatcaa    960

ataatggctt ctcctgtagg gttttcgggg ccagaattca cttttccgct atatggaact   1020

atgggaaatg cagctccaca acaacgtatt gttgctcaac taggtcaggg cgtgtataga   1080

acattatcgt ccactttata tagaagacct tttaatatag ggataaataa tcaacaacta   1140

tctgttcttg acgggacaga atttgcttat ggaacctcct caaatttgcc atccgctgta   1200

tacagaaaaa gcggaacggt agattcgctg gatgaaatac cgccacagaa taacaacgtg   1260

ccacctaggc aaggatttag tcatcgatta agccatgttt caatgtttcg ttcaggcttt   1320

agtaatagta gtgtaagtat aataagagct cctatgttct cttggataca tcgtagtgct   1380

gaatttaata atacaattga tccagagaga attaatcaaa tacctttaac aaaatctact   1440

aatcttggct ctggaacttc tgtcgttaaa ggaccaggat ttacaggagg agatattctt   1500

cgaagaactt cacctggcca gatttcaacc ttaagagtaa atattactgc accattatca   1560

caaagatatc gggtaagaat tcgctacgct tctaccacaa atttacaatt ccatacatca   1620

attgacggaa gacctattaa tcaggggaat ttttcagcaa ctatgagtag tgggagtaat   1680

ttacagtccg gaagctttag gactgtaggt tttactactc cgtttaactt ttcaaatgga   1740

tcgagtgtat ttacgttaag tgctcatgtc ttcaattcag gcaatgaatt ttatatagat   1800
```

-continued

```
cgaattgaat ttgttccggc agaagtaacc tttgaggcag aatatgattt agaaagagca   1860

caaaaggcgg tgagtgagct gcttacttct tccaatcaaa tcgggttaaa aacagatgtg   1920

acggattatc atattgatca agtatccaat ttagttgagt gtttatctga tgaattttgt   1980

ctggatgaaa aaaaagaatt gtccgaggaa gtcaaacatg cgaagcgact tantgatgag   2040

cggaatttac ttcaagatcc aaactttaga gggatcaata gacaactaga ccgtggctgg   2100

aggggaagta cggatattac catccaagga ggcgatgacg tattcaaaga gaattacgtt   2160

acgctattgg gtaccgttga tgagtgctat ccaacgtatt tatatcagaa aatagatgag   2220

tcgaaattaa aagcttatac ccgttatgaa ttaagagggt atatcgaaga tagtcaagac   2280

ttagaaatct atttgatccg ttacaatgca aaacacgaaa tagtaaatgt gccaggcacg   2340

ggttccttat ggccgctttc agcccaaagt ccaatcggaa agtgtggaga accgaatcga   2400

tgcgcgccac accttgaatg gaatcctgat ctagattgtt cctgcagaga cggggaaaaa   2460

tgtgcacatc attcccatca tttcaccttg gatattgatg ttggatgtac agacttaaat   2520

gaggacttag gtgtatgggt gatattcaag attaagacgc aagatggcca tgcaagacta   2580

gggaatctag agtttctcga agagaaacca ttattagggg aagcactagc tcgtgtgaaa   2640

agagcggaga agaagtggag agacaaacga gagaaactgc agttggaaac aaatattgtt   2700

tataaagagg caaaagaatc tgtagatgct ttatttgtaa actctcaata tgatagatta   2760

caagtggata cgaacatcgc gatgattcat gcggcagata aacgcgttca tagaatccgg   2820

gaagcgtatc tgccagagtt gtctgtgatt ccaggtgtca atgcggccat tttcgaagaa   2880

ttagagggac gtatttttac agcgtattcc ttatatgatg cgagaaatgt cattaaaaat   2940

ggcgatttca ataatggctt attatgctgg aacgtgaaag gtcatgtaga tgtagaagag   3000

caaaacaacc accgttcggt ccttgttatc ccagaatggg aggcagaagt gtcacaagag   3060

gttcgtgtct gtccaggtcg tggctatatc cttcgtgtca cagcatataa agagggatat   3120

ggagagggct gcgtaacgat ccatgagatc gaagacaata cagacgaact gaaattcagc   3180

aactgtgtag aagaggaagt atatccaaac aacacagtaa cgtgtaataa ttatactggg   3240

actcaagaag aatatgaggg tacgtacact tctcgtaatc aaggatatga cgaagcctat   3300

ggtaataacc cttccgtacc agctgattac gcttcagtct atgaagaaaa atcgtataca   3360

gatggacgaa gagagaatcc ttgtgaatct aacagaggct atggggatta cacaccacta   3420

ccggctggtt atgtaacaaa ggatttagag tacttcccag agaccgataa ggtatggatt   3480

gagatcggag aaacagaagg aacattcatc gtggatagcg tggaattact ccttatggag   3540

gaa                                                                 3543
```

```
<210> SEQ ID NO 2
<211> LENGTH: 591
<212> TYPE: PRT
<213> ORGANISM: Artificial Sequence
<220> FEATURE:
<223> OTHER INFORMATION: Cry1 variant

<400> SEQUENCE: 2

Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Ile Ile Trp Gly Ile Phe Gly Pro Ser Gln Trp Asp Ala Phe
        35                  40                  45
```

-continued

```
Leu Val Gln Ile Glu Gln Leu Ile Asn Gln Arg Ile Gly Glu Phe Ala
    50                  55                  60

Arg Asn Gln Ala Ile Ser Arg Leu Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Arg Glu Glu Met Arg Ile Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Tyr Thr
                165                 170                 175

Asp His Ala Val Arg Trp Tyr Asn Thr Gly Leu Glu Arg Val Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Val Ser Gln Leu Thr Arg Glu Val Tyr
225                 230                 235                 240

Thr Asp Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480
```

```
Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Phe Tyr Ile Asp Arg Ile Glu Phe
                565                 570                 575

Val Pro Ala Glu Val Thr Phe Glu Ala Glu Tyr Asp Leu Glu Arg
            580                 585                 590
```

<210> SEQ ID NO 3
<211> LENGTH: 3543
<212> TYPE: DNA
<213> ORGANISM: Artificial Sequence
<220> FEATURE:
<223> OTHER INFORMATION: Cry1 variant

<400> SEQUENCE: 3

```
atgcataaca atccgaacac caatgaatgc attccttata attgtttaag taaccctgaa     60

gtagaagtat taggtggaga aagaatagaa actggttaca ccccaatcga tatttccttg    120

tcgctaacgc aatttctttt gagtgaattt gttcccggtg ctggatttgt gttaggacta    180

gttgatataa tatggggaat ttttggtccc tctcaatggg acgcatttct tgtacaaatt    240

gaacagttaa ttaaccaaag aatagaagaa ttcgctagga accaagccat ttctagatta    300

gaaggactaa gcaatcttta tcaaatttac gcagaatctt ttagagagtg ggaagcagat    360

cctactaatc cagcattaag agaagagatg cgtattcaat tcaatgacat gaacagtgcc    420

cttacaaccg ctattcctct tttgcagtt caaaattatc aagttcctct tttatcagta     480

tatgttcaag ctgcaaattt acatttatca gttttgagag atgtttcagt gtttggacaa    540

aggtggggat ttgatgccgc gactatcaat agtcgttata atgatttaac taggcttatt    600

ggcaactata cagatcatgc tgtacgctgg tacaatacgg gattagagcg tgtatgggga    660

ccggattcta gagattggat aagatataat caatttagaa gagaattaac actaactgta    720

ttagatatcg tttctctatt tccgaactat gatagtagaa cgtatccaat tcgaacagtt    780

tcccaactaa caagggaagt ttatacggac ccagtattag aaaattttga tggtagtttt    840

cgaggctcgg ctcagggcat agaaggaagt attaggagtc cacatttgat ggatatactt    900

aacagtataa ccatctatac ggatgctcat agaggagaat attattggtc agggcatcaa    960

ataatggctt ctcctgtagg gttttcgggg ccagaattca cttttccgct atatggaact   1020

atgggaaatg cagctccaca acaacgtatt gttgctcaac taggtcaggg cgtgtataga   1080

acattatcgt ccactttata tagaagacct tttaatatag ggataaataa tcaacaacta   1140

tctgttcttg acgggacaga atttgcttat ggaacctcct caaatttgcc atccgctgta   1200

tacagaaaaa gcggaacggt agattcgctg gatgaaatac cgccacagaa tgacaacgtg   1260

ccacctaggc aaggatttag tcatcgatta agccatgttt caatgtttcg ttcaggcttt   1320

agtaatagta gtgtaagtat aataagagct cctatgttct cttggataca tcgtagtgct   1380

gaatttaata atacaattga tccagagaga attaatcaaa tacctttaac aaaatctact   1440
```

-continued

```
aatcttggct ctggaacttc tgtcgttaaa ggaccaggat ttacaggagg agatattctt   1500
cgaagaactt cacctggcca gatttcaacc ttaagagtaa atattactgc accattatca   1560
caaagatatc gggtaagaat tcgctacgct tctaccacaa atttacaatt ccatacatca   1620
attgacggaa gacctattaa tcaggggaat ttttcagcaa ctatgagtag tgggagtaat   1680
ttacagtccg gaagctttag gactgtaggt tttactactc cgtttaactt ttcaaatgga   1740
tcgagtgtat ttacgttaag tgctcatgtc ttcaattcag gcaatgaagt ttatatagat   1800
cgaattgaat ttgttccggc agaagtaacc tttgaggcag aatatgattt agaaagagca   1860
caaaaggcgg tgagtgagct gtttacttct tccaatcaaa tcgggttaaa aacagatgtg   1920
acggattatc atattgatca agtatccaat ttagttgagt gtttatctga tgaattttgt   1980
ctggatgaaa aaaaagaatt gtccgagaaa gtcaaacatg cgaagcgact tagtgatgag   2040
cggaatttac ttcaagatcc aaactttgga gggatcaata gacaactaga ccgtggctgg   2100
aggggaagta cggatattac catccaagga ggcgatgacg tattcaaaga gaattacgtt   2160
acgctattgg gtaccgttga tgagtgctat ccaacgtatt tatatcagaa aatagatgag   2220
tcgaaattaa aagcttatac ccgttatgaa ttaagagggt atatcgaaga tagtcaagac   2280
ttagaaatct atttgatccg ttacaatgca aaacacgaaa tagtaaatgt gccaggcacg   2340
ggttccttat ggccgctttc agcccaaagt ccaatcggaa agtgtggaga accgaatcga   2400
tgcgcgccac accttgaatg gaatcctgat ctagattgtt cctgcagaga cggggaaaaa   2460
tgtgcacatc attcccatca tttcaccttg gatattgatg ttggatgtac agacttaaat   2520
gaggacttag gtgtatgggt gatattcaag attaagacgc aagatggcca tgcaagacta   2580
gggaatctag agtttctcga agagaaacca ttattagggg aagcactagc tcgtgtgaaa   2640
agagcggaga agaagtggag agacaaacga gagaaactgc agttggaaac aaatattgtt   2700
tataaagagg caaaagaatc tgtagatgct ttatttgtaa actctcaata tgatagatta   2760
caagtggata cgaacatcgc gatgattcat gcggcagata aacgcgttca tagaatccgg   2820
gaagcgtatc tgccagagtt gtctgtgatt ccaggtgtca atgcggccat tttcgaagaa   2880
ttagagggac gtatttttac agcgtattcc ttatatgatg cgagaaatgt cattaaaaat   2940
ggcgatttca ataatggctt attatgctgg aacgtgaaag gtcatgtaga tgtagaagag   3000
caaaacaacc accgttcggt ccttgttatc ccagaatggg aggcagaagt gtcacaagag   3060
gttcgtgtct gtccaggtcg tggctatatc cttcgtgtca cagcatataa agagggatat   3120
ggagagggct gcgtaacgat ccatgagatc gaagacaata cagacgaact gaaattcagc   3180
aactgtgtag aagaggaagt atatccaaac aacacagtaa cgtgtaataa ttatactggg   3240
actcaagaag aatatgaggg tacgtacact tctcgtaatc aaggatatga cgaagcctat   3300
ggtaataacc cttccgtacc agctgattac gcttcagtct atgaagaaaa atcgtataca   3360
gatggacgaa gagagaatcc ttgtgaatct aacagaggct atggggatta cacaccacta   3420
ccggctggtt atgtaacaaa ggatttagag tacttcccag agaccgataa ggtatggatt   3480
gagatcggag aaacagaagg aacattcatc gtggatagcg tggaattact ccttatggag   3540
gaa                                                                 3543
```

<210> SEQ ID NO 4
<211> LENGTH: 591
<212> TYPE: PRT
<213> ORGANISM: Artificial Sequence
<220> FEATURE:
<223> OTHER INFORMATION: Cry1 variant -continued

<400> SEQUENCE: 4

```
Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Ile Ile Trp Gly Ile Phe Gly Pro Ser Gln Trp Asp Ala Phe
        35                  40                  45

Leu Val Gln Ile Glu Gln Leu Ile Asn Gln Arg Ile Glu Glu Phe Ala
    50                  55                  60

Arg Asn Gln Ala Ile Ser Arg Leu Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Arg Glu Glu Met Arg Ile Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Tyr Thr
                165                 170                 175

Asp His Ala Val Arg Trp Tyr Asn Thr Gly Leu Glu Arg Val Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Val Ser Gln Leu Thr Arg Glu Val Tyr
225                 230                 235                 240

Thr Asp Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asp Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415
```

-continued

```
Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590
```

<210> SEQ ID NO 5
<211> LENGTH: 3546
<212> TYPE: DNA
<213> ORGANISM: Artificial Sequence
<220> FEATURE:
<223> OTHER INFORMATION: Cry1 variant

<400> SEQUENCE: 5

```
atgggacaca acaatccaaa taccaatgaa tgcatcccct ataattgctt gagcaaccct      60

gaagttgaag ttctgggagg tgagaggata gaaactggat ataccccctat tgatatctct    120

ctgtctttga ctcagttcct cctgagtgag tttgttccag gtgcaggatt tgtgttgggt     180

ttggtagaca ttatctgggg aatctttgga ccatcccaat gggatgcctt tctggtccaa     240

atagagcaac tcataaacca gcgcattgag gaatttgcac gtaaccaggc aatctcccga     300

cttgagggat tgtcaaactt gtaccagata tatgctgaaa gtttcagaga gtgggaagct     360

gacccaacca accctgcatt gagggaagag atgaggattc agttcaatga tatgaactca     420

gcactgacca ctgccatacc cttgtttgca gtacagaact atcaagtccc attactatca     480

gtctatgtgc aagcagcaaa cctacatttg agtgtcctcc gagatgtatc agtttttggt     540

caacgttggg gatttgatgc tgctaccatc aacagtcgtt acaatgacct cacacgactg     600

attgggaact acacagatca cgcagtccgt tggtacaata ctggattgga gagagtttgg     660

ggacctgata gtcgtgattg gattcgttac aatcagtttc gtcgggaact taccctgact     720

gtcttggata tagtgtcact gtttcctaac tatgatagtc gtacatatcc aatacgaaca     780

gtaagtcagc tgactcgtga agtctacacg gaccctgtcc tggagaactt tgatggtagc     840

ttccgtggat cagcacaagg catagagggt tccatccgga gtcctcatct catggacatc     900

ctgaacagca ttacaatcta cacagatgct catcgaggtg agtattactg gtcaggacac     960

caaatcatgg catccccagt tggattttct ggtccagagt tcactttccc cttgtatgga    1020

acaatgggta atgctgctcc acagcaacga atagttgctc aattgggaca aggggtatat    1080

cgaaccttat catcaacact gtatcgacgt ccattcaaca ttgggataaa caatcaacag    1140
```

-continued

```
ttgtctgtac tagatgggac agagtttgct tatggaactt cctccaacct cccttcagca   1200
gtttatcgga agtctgggac tgtagactca ctagatgaga tacctccaca gaatgacaat   1260
gtacctccaa gacaaggatt ctcccaccgt ctctctcatg tgtctatgtt ccgtagtggc   1320
tttagtaaca gcagtgtgag catcatacgt gcacctatgt tttcatggat tcaccgtagt   1380
gcagagttca ataacaccat tgaccctgaa cgaatcaatc aaatcccact taccaaaagc   1440
accaaccttg gtagcggaac cagcgttgtg aagggtcctg gtttcactgg tggggatatt   1500
ctgcgacgta ccagccctgg acagattagc acactgcgtg tgaacatcac cgctccactg   1560
agtcagcgct atcgagtgag gattcgctat gctagcacta ccaaccttca gttccatacc   1620
agcattgatg gtcgtccaat taaccaaggc aacttcagcg ctaccatgtc cagcggctca   1680
aacctgcaaa gtggatcatt ccgcaccgtt ggctttacca ctccattcaa cttcagcaac   1740
ggcagtagcg tgttcaccct ttccgcacat gtgttcaaca gtggcaacga agtgtacatc   1800
gatagaatcg agtttgtgcc agcggaagtg acttttgaag ctgagtacga ccttgaacgt   1860
gcccaaaagg ccgttagcga gctcttcact tcttccaacc agatcggatt gaaaacagat   1920
gttacagact accacattga ccaggtgtcc aatcttgtgg attgcttgtc tgatgagttc   1980
tgtctcgatg agaagcgaga actctctgaa aaggttaagc acgctaagag actcagcgat   2040
gaacgaaacc ttcttcagga cccaaatttc aggggaatta atagacaacc agatagaggt   2100
tggcgtggat caacagacat cactatccaa ggtggagacg atgtttttaa ggagaactac   2160
gtgacccttc ctggtactgt tgacgagtgc tatcctacct acctttacca gaagattgac   2220
gaatcaaagc tcaaagcata cactcgttat gagcttcgtg gttacatcga agattcacaa   2280
gatcttgaaa tctacctcat cagatacaac gctaaacacg aaatcgtcaa cgttccaggt   2340
actggatctc tgtggccact ctctgcacag tcacctattg gcaagtgcgg tgagccaaat   2400
agatgtgcac cacacctgga gtggaatccc gatctggact gtagttgtcg tgacggggag   2460
aagtgcgctc atcacagcca tcacttcact cttgatatcg atgttggatg taccgacctt   2520
aatgaagacc tgggcgtttg ggttatcttc aagattaaga cccaggatgg tcatgccaga   2580
cttggtaatc tggagttcct tgaagagaaa cccttgttgg gtgaagctct ggccagagtc   2640
aagcgtgctg agaagaaatg gcgtgataaa cgtgaaaagt tgcaattgga gactaacatt   2700
gtctacaaag aggcaaagga gtctgtggat gccttgttcg tgaactctca gtacgaccga   2760
ctccaagtgg ataccaacat tgctatgatt catgctgctg acaaacgtgt tcaccgtatc   2820
agagaagcct atctccctga actgtcagtg atcccaggag tcaacgctgc aatcttcgag   2880
gagcttgaag gtcgaatctt cactgcctat tcactttacg atgcacgaaa cgtgattaag   2940
aatggggatt ttaataacgg gttgttgtgc tggaatgtga aggggcacgt ggatgttgag   3000
gaacaaaaca accaccgttc cgtgcttgtt attcctgagt gggaagcaga ggtgtctcag   3060
gaggttaggg tgtgtcctgg tagaggatat atcttgagag tgactgccta taaggaaggc   3120
tatggtgaag gttgcgtgac aatccacgag atcgaagaca acacagatga gcttaagttc   3180
tctaactgcg ttgaggagga agtctaccca aacaataccg tcacttgtaa caattacaca   3240
ggcacacaag aagagtacga aggaacctac acctcccgaa atcagggtta tgatgaggcc   3300
tatggtaata atccttctgt gcctgccgat tatgcttctg tttacgagga aaagtcttac   3360
actgatggcc gtcgtgagaa cccttgcgaa tccaaccgtg gatacggtga ttacactcca   3420
cttccagcag gatacgttac taaggatctt gagtactttc cagagactga taaagtttgg   3480
atcgaaatcg gagagactga aggcacattc atcgtggatt ctgtggagct cttgctcatg   3540
```

gaggaa 3546

<210> SEQ ID NO 6
<211> LENGTH: 591
<212> TYPE: PRT
<213> ORGANISM: Artificial Sequence
<220> FEATURE:
<223> OTHER INFORMATION: Cry1 variant

<400> SEQUENCE: 6

Ile Glu Thr Gly Tyr Thr Pro Ile Asp Ile Ser Leu Ser Leu Thr Gln
1 5 10 15

Phe Leu Leu Ser Glu Phe Val Pro Gly Ala Gly Phe Val Leu Gly Leu
20 25 30

Val Asp Ile Ile Trp Gly Ile Phe Gly Pro Ser Gln Trp Asp Ala Phe
35 40 45

Leu Val Gln Ile Glu Gln Leu Ile Asn Gln Arg Ile Glu Glu Phe Ala
50 55 60

Arg Asn Gln Ala Ile Ser Arg Leu Glu Gly Leu Ser Asn Leu Tyr Gln
65 70 75 80

Ile Tyr Ala Glu Ser Phe Arg Glu Trp Glu Ala Asp Pro Thr Asn Pro
85 90 95

Ala Leu Arg Glu Glu Met Arg Ile Gln Phe Asn Asp Met Asn Ser Ala
100 105 110

Leu Thr Thr Ala Ile Pro Leu Phe Ala Val Gln Asn Tyr Gln Val Pro
115 120 125

Leu Leu Ser Val Tyr Val Gln Ala Ala Asn Leu His Leu Ser Val Leu
130 135 140

Arg Asp Val Ser Val Phe Gly Gln Arg Trp Gly Phe Asp Ala Ala Thr
145 150 155 160

Ile Asn Ser Arg Tyr Asn Asp Leu Thr Arg Leu Ile Gly Asn Tyr Thr
165 170 175

Asp His Ala Val Arg Trp Tyr Asn Thr Gly Leu Glu Arg Val Trp Gly
180 185 190

Pro Asp Ser Arg Asp Trp Ile Arg Tyr Asn Gln Phe Arg Arg Glu Leu
195 200 205

Thr Leu Thr Val Leu Asp Ile Val Ser Leu Phe Pro Asn Tyr Asp Ser
210 215 220

Arg Thr Tyr Pro Ile Arg Thr Val Ser Gln Leu Thr Arg Glu Val Tyr
225 230 235 240

Thr Asp Pro Val Leu Glu Asn Phe Asp Gly Ser Phe Arg Gly Ser Ala
245 250 255

Gln Gly Ile Glu Gly Ser Ile Arg Ser Pro His Leu Met Asp Ile Leu
260 265 270

Asn Ser Ile Thr Ile Tyr Thr Asp Ala His Arg Gly Glu Tyr Tyr Trp
275 280 285

Ser Gly His Gln Ile Met Ala Ser Pro Val Gly Phe Ser Gly Pro Glu
290 295 300

Phe Thr Phe Pro Leu Tyr Gly Thr Met Gly Asn Ala Ala Pro Gln Gln
305 310 315 320

Arg Ile Val Ala Gln Leu Gly Gln Gly Val Tyr Arg Thr Leu Ser Ser
325 330 335

Thr Leu Tyr Arg Arg Pro Phe Asn Ile Gly Ile Asn Asn Gln Gln Leu
340 345 350

Ser Val Leu Asp Gly Thr Glu Phe Ala Tyr Gly Thr Ser Ser Asn Leu

-continued

```
        355                 360                 365

Pro Ser Ala Val Tyr Arg Lys Ser Gly Thr Val Asp Ser Leu Asp Glu
    370                 375                 380

Ile Pro Pro Gln Asn Asp Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590
```

<210> SEQ ID NO 7
<211> LENGTH: 3567
<212> TYPE: DNA
<213> ORGANISM: Artificial Sequence
<220> FEATURE:
<223> OTHER INFORMATION: Cry1 variant

<400> SEQUENCE: 7

```
atgcaggaaa ataatcaaaa tcaatgcata ccttacaatt gtttaagtaa tcctgaagaa      60

gtacttttgg atggagaacg gatatcaact ggtaattcat caattgatat ttctctgtca     120

cttgttcagt ttctggtatc taactttgta ccagggggag gatttttagt tggattaata     180

gattttgtat ggggaatagt tggcccttct caatgggatg catttctagt gcaaattgaa     240

caattaatta atgaaagaat agctgaattt gctaggaatg ctgctattgc taatttagaa     300

ggattaggaa acaatttcaa tatatatgtg gaagcattta aagaatggga agaagatcct     360

aataatccag caaccaggac cagagtaatt gatcgctttc gtatacttga tgggctgctt     420

gaaagggaca ttccttcgtt tcgaatttct ggatttgaag taccccttt atccgtttat      480

gcccaagcgg ccaatctgca tctagctata ttaagagatt ctgtaatttt tggagaaaga     540

tggggattga caacgataaa tgtcaatgag aactataata gactaattag gcatattgat     600

gaatatgctg atcactgtgc aaatacgtat aatcggggat taaataattt accgaaatct     660

acgtatcaag attggataac atataaccga ttacggagag acttaacatt gactgtatta     720

gatatcgccg ctttctttcc aaactatgac aataggagat atccaattca gccagttggt     780
```

-continued

```
caactaacaa gggaagttta tgcggaccca ttaattaatt ttaatccaca gttacagtct    840

gtagctcaat tacctacttt taacgttatg gagagcagcg caattagaaa tcctcattta    900

tttgatatat tgaataatct tacaatcttt acgggttggt ttagtgttgg acgcaatttt    960

tattggggag gacatcgagt aatatctagc cttataggag gtggtaacat aacatctccc   1020

atatatggaa gagaggcgaa ccaggagccc ccaagatcct ttacttttaa tggaccggta   1080

tttaggactt tatcaaatcc tactttacga ttattacagc aaccatggcc agcgccacca   1140

tttaatctac gtggtgttga aggagtagaa ttttctacac ctacaaatag cttaacgtat   1200

cgaggaagag gtacggttga ttctttaact gaattgccgc ctgaggataa tagtgtgcca   1260

cctcgcgaag gatatagtca tcgtttatgt catgcaactt ttgttcaaag atctggaaca   1320

ccttttttaa caactggtgt agtattttct tggacgcatc gtagtgctac tcttacaaat   1380

acaattgatc cagagagaat taatcaaata cctttagtga aaggatttag agtttggggg   1440

ggcacctctg tcgttacagg accaggattt acaggagggg atatccttcg aagaaatacc   1500

tttggtgatt ttgtatctct acaagtcaat attaattcac caattaccca aagataccgt   1560

ttaagatttc gttacgcttc cagtagggat gcacgagtta tagtattaac aggagcggca   1620

tccacaggag tgggaggcca agttagtgta aatatgcctc ttcagaaaac tatggaaata   1680

ggggagaact taacatctag aacatttaga tataccgatt ttagtaatcc tttttcattt   1740

agagccaatc cagatacaat tgggataagt gaacaacctc tatttggtgc aggttctatt   1800

agtagcggtg aactttatat agataaaatt gaaattattc tagcagatgc aacatttgaa   1860

gcggaatctg atttagaaag agcacaaaag gcggtgaatg ccctgtttac ttcttccaat   1920

caaatcgggt taaaaaccga tgtgacggat tatcatattg atcaagtatc caatttagtg   1980

gattgtttat cagatgaatt ttgtctggat gaaaagcgag aattgtccga gaaagtcaaa   2040

catgcgaagc gactcagtga tgagcggaat ttacttcaag atccaaactt cagagggatc   2100

aatagacaac cagaccgtgg ctggagagga agtacagata ttaccatcca aggaggagat   2160

gacgtattca aagagaatta cgtcacacta ccgggtaccg ttgatgagtg ctatccaacg   2220

tatttatatc agaaaataga tgagtcgaaa ttaaaagctt atacccgtta tgaattaaga   2280

gggtatatcg aagatagtca agacttagaa atctatttga tccgttacaa tgcaaaacac   2340

gaaatagtaa atgtgccagg cacgggttcc ttatggccgc tttcagccca aagtccaatc   2400

ggaaagtgtg gagaaccgaa tcgatgcgcg ccacaccttg aatggaatcc tgatctagat   2460

tgttcctgca gagacgggga aaaatgtgca catcattccc atcatttcac cttggatatt   2520

gatgttggat gtacagactt aaatgaggac ttaggtgtat gggtgatatt caagattaag   2580

acgcaagatg gccatgcaag actagggaat ctagagtttc tcgaagagaa accattatta   2640

ggggaagcac tagctcgtgt gaaaagagcg gagaagaagt ggagagacaa acgagagaaa   2700

ctgcagttgg aaacaaatat tgtttataaa gaggcaaaag aatctgtaga tgctttattt   2760

gtaaactctc aatatgatag attacaagtg gatacgaaca tcgcgatgat tcatgcggca   2820

gataaacgcg ttcatagaat ccgggaagcg tatctgccag agttgtctgt gattccaggt   2880

gtcaatgcgg ccattttcga agaattagag ggacgtattt ttacagcgta ttccttatat   2940

gatgcgagaa atgtcattaa aaatggcgat ttcaataatg gcttattatg ctggaacgtg   3000

aaaggtcatg tagatgtaga agagcaaaac aaccaccgtt cggtccttgt tatcccagaa   3060

tgggaggcag aagtgtcaca agaggttcgt gtctgtccag gtcgtggcta tatccttcgt   3120

gtcacagcat ataaagaggg atatggagag ggctgcgtaa cgatccatga gatcgaagac   3180
```

-continued

```
aatacagacg aactgaaatt cagcaactgt gtagaagagg aagtatatcc aaacaacaca   3240

gtaacgtgta ataattatac tgggactcaa gaagaatatg agggtacgta cacttctcgt   3300

aatcaaggat atgacgaagc ctatggtaat aacccttccg taccagctga ttacgcttca   3360

gtctatgaag aaaaatcgta tacagatgga cgaagagaga atccttgtga atctaacaga   3420

ggctatgggg attacacacc actaccggct ggttatgtaa caaaggattt agagtacttc   3480

ccagagaccg ataaggtatg gattgagatc ggagaaacag aaggaacatt catcgtggat   3540

agcgtggaat tactccttat ggaggaa                                        3567
```

```
<210> SEQ ID NO 8
<211> LENGTH: 600
<212> TYPE: PRT
<213> ORGANISM: Artificial Sequence
<220> FEATURE:
<223> OTHER INFORMATION: Cry1 variant

<400> SEQUENCE: 8

Ile Ser Thr Gly Asn Ser Ser Ile Asp Ile Ser Leu Ser Leu Val Gln
1               5                   10                  15

Phe Leu Val Ser Asn Phe Val Pro Gly Gly Gly Phe Leu Val Gly Leu
            20                  25                  30

Ile Asp Phe Val Trp Gly Ile Val Gly Pro Ser Gln Trp Asp Ala Phe
        35                  40                  45

Leu Val Gln Ile Glu Gln Leu Ile Asn Glu Arg Ile Ala Glu Phe Ala
    50                  55                  60

Arg Asn Ala Ala Ile Ala Asn Leu Glu Gly Leu Gly Asn Asn Phe Asn
65                  70                  75                  80

Ile Tyr Val Glu Ala Phe Lys Glu Trp Glu Glu Asp Pro Asn Asn Pro
                85                  90                  95

Ala Thr Arg Thr Arg Val Ile Asp Arg Phe Arg Ile Leu Asp Gly Leu
            100                 105                 110

Leu Glu Arg Asp Ile Pro Ser Phe Arg Ile Ser Gly Phe Glu Val Pro
        115                 120                 125

Leu Leu Ser Val Tyr Ala Gln Ala Ala Asn Leu His Leu Ala Ile Leu
    130                 135                 140

Arg Asp Ser Val Ile Phe Gly Glu Arg Trp Gly Leu Thr Thr Ile Asn
145                 150                 155                 160

Val Asn Glu Asn Tyr Asn Arg Leu Ile Arg His Ile Asp Glu Tyr Ala
                165                 170                 175

Asp His Cys Ala Asn Thr Tyr Asn Arg Gly Leu Asn Asn Leu Pro Lys
            180                 185                 190

Ser Thr Tyr Gln Asp Trp Ile Thr Tyr Asn Arg Leu Arg Arg Asp Leu
        195                 200                 205

Thr Leu Thr Val Leu Asp Ile Ala Ala Phe Phe Pro Asn Tyr Asp Asn
    210                 215                 220

Arg Arg Tyr Pro Ile Gln Pro Val Gly Gln Leu Thr Arg Glu Val Tyr
225                 230                 235                 240

Ala Asp Pro Leu Ile Asn Phe Asn Pro Gln Leu Gln Ser Val Ala Gln
                245                 250                 255

Leu Pro Thr Phe Asn Val Met Glu Ser Ser Ala Ile Arg Asn Pro His
            260                 265                 270

Leu Phe Asp Ile Leu Asn Asn Leu Thr Ile Phe Thr Gly Trp Phe Ser
        275                 280                 285

Val Gly Arg Asn Phe Tyr Trp Gly Gly His Arg Val Ile Ser Ser Leu
    290                 295                 300
```

```
Ile Gly Gly Gly Asn Ile Thr Ser Pro Ile Tyr Gly Arg Glu Ala Asn
305                 310                 315                 320

Gln Glu Pro Pro Arg Ser Phe Thr Phe Asn Gly Pro Val Phe Arg Thr
                325                 330                 335

Leu Ser Asn Pro Thr Leu Arg Leu Leu Gln Gln Pro Trp Pro Ala Pro
            340                 345                 350

Pro Phe Asn Leu Arg Gly Val Glu Gly Val Glu Phe Ser Thr Pro Thr
        355                 360                 365

Asn Ser Leu Thr Tyr Arg Gly Arg Gly Thr Val Asp Ser Leu Thr Glu
    370                 375                 380

Leu Pro Pro Glu Asp Asn Ser Val Pro Pro Arg Glu Gly Tyr Ser His
385                 390                 395                 400

Arg Leu Cys His Ala Thr Phe Val Gln Arg Ser Gly Thr Pro Phe Leu
                405                 410                 415

Thr Thr Gly Val Val Phe Ser Trp Thr His Arg Ser Ala Thr Leu Thr
            420                 425                 430

Asn Thr Ile Asp Pro Glu Arg Ile Asn Gln Ile Pro Leu Val Lys Gly
        435                 440                 445

Phe Arg Val Trp Gly Gly Thr Ser Val Val Thr Gly Pro Gly Phe Thr
    450                 455                 460

Gly Gly Asp Ile Leu Arg Arg Asn Thr Phe Gly Asp Phe Val Ser Leu
465                 470                 475                 480

Gln Val Asn Ile Asn Ser Pro Ile Thr Gln Arg Tyr Arg Leu Arg Phe
                485                 490                 495

Arg Tyr Ala Ser Ser Arg Asp Ala Arg Val Ile Val Leu Thr Gly Ala
            500                 505                 510

Ala Ser Thr Gly Val Gly Gly Gln Val Ser Val Asn Met Pro Leu Gln
        515                 520                 525

Lys Thr Met Glu Ile Gly Glu Asn Leu Thr Ser Arg Thr Phe Arg Tyr
    530                 535                 540

Thr Asp Phe Ser Asn Pro Phe Ser Phe Arg Ala Asn Pro Asp Thr Ile
545                 550                 555                 560

Gly Ile Ser Glu Gln Pro Leu Phe Gly Ala Gly Ser Ile Ser Ser Gly
                565                 570                 575

Glu Leu Tyr Ile Asp Lys Ile Glu Ile Ile Leu Ala Asp Ala Thr Phe
            580                 585                 590

Glu Ala Glu Ser Asp Leu Glu Arg
        595                 600
```

<210> SEQ ID NO 9
<211> LENGTH: 3567
<212> TYPE: DNA
<213> ORGANISM: Artificial Sequence
<220> FEATURE:
<223> OTHER INFORMATION: Cry1 variant

<400> SEQUENCE: 9

```
atggaggaga acaaccaaaa ccaatgcatc ccatataact gcttgagtaa ccctgaggaa      60

gtgctcctcg acggtgagcg tatctctaca ggtaattctt caatcgacat ctccctttcc     120

ttggtgcaat tcctcgtttc aaatttcgtg ccaggaggtg gattccttgt gggattgatc     180

gacttcgttt ggggaatcgt gggcccaagt caatgggatg ctttcctggt gcaaattgaa     240

caacttatca acgagcgtat cgccgagttt gcacgtaacg ctgctattgc aaatctggag     300

ggtctgggga ataacttcaa tatctacgtt gaggctttta aggaatggga ggaagatcct     360
```

-continued

```
aacaatccag caacacgtac ccgtgtgatt gaccgtttta gaattttgga tgggctgctt    420
gaaagggata tcccttcatt ccgaatttct ggttttgagg tgcccctcct ttctgtttat    480
gctcaagcag ctaacctcca tttggctatc cttcgtgata gcgtgatctt tggggagcgt    540
tggggactta ctacaatcaa cgtcaacgag aactataacc gactgatcag acacattgat    600
gagtatgccg atcactgcgc taatacctac aatcgcggac ttaacaatct tccaaagtct    660
acctaccagg actggattac ttacaaccgt ttgcgtaggg atcttacact tacagttctt    720
gacattgcag ctttcttccc aaactatgat aaccgaagat accctatcca gccagtggga    780
caacttacac gagaggttta cgcagatcca ttgattaact tcaaccctca acttcaatca    840
gttgctcaat tgccaacctt caacgttatg gaaagctctg ctatcaggaa tccccatctg    900
ttcgacattc ttaacaacct cacaatcttt acaggttggt tcagtgtcgg ccgtaatttc    960
tattggggag gacaccgtgt catctctagt cttatcggtg gaggtaatat tacctcccca   1020
atttatggga gagaggccaa ccaggaacct ccacgtagtt tcactttcaa tggtccagtc   1080
tttcgtactt tgagcaaccc aactctgagg cttctccaac aaccttggcc agcacctcca   1140
ttcaatcttc gtggagttga aggtgtggag ttttccactc caaccaacag cttgacttat   1200
cgtggtagag gtactgtcga ctccttgacc gaacttccac ctgaggataa ctctgtgcca   1260
ccacgtgagg gttattcaca tcgtttgtgt cacgcaactt ttgttcagag aagtggcaca   1320
ccatttctga ctactggcgt ggtcttcagt tggacacatc gtagcgcaac tcttactaac   1380
acaatcgacc ctgaacgtat caatcaaatc ccactcgtca aaggttttcg tgtttgggga   1440
ggcacatccg ttgtcactgg acctggtttc acaggtggcg atatccttcg aaggaacacc   1500
ttcggtgatt tcgtgagtct gcaagttaac atcaatagtc ccatcacaca aagatatcgt   1560
ctcagattca gatacgcatc atctcgtgat gcacgtgtca ttgtgcttac tggtgcagca   1620
tctactggag ttggtggtca agttagtgtc aatatgccac tgcaaaagac tatggaaatc   1680
ggcgagaact tgacatccag aacctttagg tacactgact tttccaatcc tttttcattc   1740
cgtgccaatc ctgacactat tggtatctcc gaacaaccac tttttggagc tggatcaatt   1800
tcatctggag aattgtacat tgacaagatt gagatcattc ttgctgatgc aacctttgaa   1860
gctgagtctg acctggaaag agcacaaaag gccgttaacg ccctcttcac ttcttccaac   1920
cagatcggat tgaaaacaga tgttacagac taccacattg accaggtgtc caatcttgtg   1980
gattgcttgt ctgatgaatt ctgtctcgat gagaagcgag aactctctga aaaggttaag   2040
cacgctaaga gactcagcga tgaacgaaac cttcttcagg acccaaattt caggggaatt   2100
aatagacaac cagatagagg ttggcgtgga tcaacagaca tcactatcca aggtggagac   2160
gatgttttta aggagaacta cgtgaccctt cctggtactg ttgacgagtg ctatcctacc   2220
tacctttacc agaagattga cgaatcaaag ctcaaagcat acactcgtta tgagcttcgt   2280
ggttacatcg aagattcaca agatcttgaa atctacctca tcagatacaa cgctaaacac   2340
gaaatcgtca acgttccagg tactggatct ctgtggccac tctctgcaca gtcacctatt   2400
ggcaagtgcg gtgagccaaa tagatgtgca ccacacctgg agtggaatcc cgatctggac   2460
tgtagttgtc gtgacgggga gaagtgcgct catcacagcc atcacttcac tcttgatatc   2520
gatgttggat gtaccgacct taatgaagac ctgggcgttt gggttatctt caagattaag   2580
acccaggatg gtcatgccag acttggtaat ctggagttcc ttgaagagaa acccttgttg   2640
ggtgaagctc tggccagagt caagcgtgct gagaagaaat ggcgtgataa acgtgaaaag   2700
ttgcaattgg agactaacat tgtctacaaa gaggcaaagg agtctgtgga tgccttgttc   2760
```

-continued

```
gtgaactctc agtacgaccg actccaagtg gataccaaca ttgctatgat tcatgctgct   2820

gacaaacgtg ttcaccgtat cagagaagcc tatctccctg aactgtcagt gatcccagga   2880

gtcaacgctg caatcttcga ggagcttgaa ggtcgaatct tcactgccta ttcactttac   2940

gatgcacgaa acgtgattaa gaatggggat tttaataacg ggttgttgtg ctggaatgtg   3000

aaggggcacg tggatgttga ggaacaaaac aaccaccgtt ccgtgcttgt tattcctgag   3060

tgggaagcag aggtgtctca ggaggttagg gtgtgtcctg gtagaggata tatcttgaga   3120

gtgactgcct ataaggaagg ctatggtgaa ggttgcgtga caatccacga gatcgaagac   3180

aacacagatg agcttaagtt ctctaactgc gttgaggagg aagtctaccc aaacaatacc   3240

gtcacttgta acaattacac aggcacacaa gaagagtacg aaggaaccta cacctcccga   3300

aatcagggtt atgatgaggc ctatggtaat aatccttctg tgcctgccga ttatgcttct   3360

gtttacgagg aaaagtctta cactgatggc cgtcgtgaga acccttgcga atccaaccgt   3420

ggatacggtg attacactcc acttccagca ggatacgtta ctaaggatct tgagtacttt   3480

ccagagactg ataaagtttg gatcgaaatc ggagagactg aaggcacatt catcgtggat   3540

tctgtggagc tcttgctcat ggaggaa                                       3567
```

```
<210> SEQ ID NO 10
<211> LENGTH: 600
<212> TYPE: PRT
<213> ORGANISM: Artificial Sequence
<220> FEATURE:
<223> OTHER INFORMATION: Cry1 variant

<400> SEQUENCE: 10

Ile Ser Thr Gly Asn Ser Ser Ile Asp Ile Ser Leu Ser Leu Val Gln
1               5                   10                  15

Phe Leu Val Ser Asn Phe Val Pro Gly Gly Gly Phe Leu Val Gly Leu
            20                  25                  30

Ile Asp Phe Val Trp Gly Ile Val Gly Pro Ser Gln Trp Asp Ala Phe
        35                  40                  45

Leu Val Gln Ile Glu Gln Leu Ile Asn Glu Arg Ile Ala Glu Phe Ala
    50                  55                  60

Arg Asn Ala Ala Ile Ala Asn Leu Glu Gly Leu Gly Asn Asn Phe Asn
65                  70                  75                  80

Ile Tyr Val Glu Ala Phe Lys Glu Trp Glu Glu Asp Pro Asn Asn Pro
                85                  90                  95

Ala Thr Arg Thr Arg Val Ile Asp Arg Phe Arg Ile Leu Asp Gly Leu
            100                 105                 110

Leu Glu Arg Asp Ile Pro Ser Phe Arg Ile Ser Gly Phe Glu Val Pro
        115                 120                 125

Leu Leu Ser Val Tyr Ala Gln Ala Ala Asn Leu His Leu Ala Ile Leu
    130                 135                 140

Arg Asp Ser Val Ile Phe Gly Glu Arg Trp Gly Leu Thr Thr Ile Asn
145                 150                 155                 160

Val Asn Glu Asn Tyr Asn Arg Leu Ile Arg His Ile Asp Glu Tyr Ala
                165                 170                 175

Asp His Cys Ala Asn Thr Tyr Asn Arg Gly Leu Asn Asn Leu Pro Lys
            180                 185                 190

Ser Thr Tyr Gln Asp Trp Ile Thr Tyr Asn Arg Leu Arg Arg Asp Leu
        195                 200                 205

Thr Leu Thr Val Leu Asp Ile Ala Ala Phe Phe Pro Asn Tyr Asp Asn
    210                 215                 220
```

-continued

```
Arg Arg Tyr Pro Ile Gln Pro Val Gly Gln Leu Thr Arg Glu Val Tyr
225                 230                 235                 240

Ala Asp Pro Leu Ile Asn Phe Asn Pro Gln Leu Gln Ser Val Ala Gln
                245                 250                 255

Leu Pro Thr Phe Asn Val Met Glu Ser Ser Ala Ile Arg Asn Pro His
            260                 265                 270

Leu Phe Asp Ile Leu Asn Asn Leu Thr Ile Phe Thr Gly Trp Phe Ser
        275                 280                 285

Val Gly Arg Asn Phe Tyr Trp Gly Gly His Arg Val Ile Ser Ser Leu
    290                 295                 300

Ile Gly Gly Gly Asn Ile Thr Ser Pro Ile Tyr Gly Arg Glu Ala Asn
305                 310                 315                 320

Gln Glu Pro Pro Arg Ser Phe Thr Phe Asn Gly Pro Val Phe Arg Thr
                325                 330                 335

Leu Ser Asn Pro Thr Leu Arg Leu Leu Gln Gln Pro Trp Pro Ala Pro
            340                 345                 350

Pro Phe Asn Leu Arg Gly Val Glu Gly Val Glu Phe Ser Thr Pro Thr
        355                 360                 365

Asn Ser Leu Thr Tyr Arg Gly Arg Gly Thr Val Asp Ser Leu Thr Glu
    370                 375                 380

Leu Pro Pro Glu Asp Asn Ser Val Pro Pro Arg Glu Gly Tyr Ser His
385                 390                 395                 400

Arg Leu Cys His Ala Thr Phe Val Gln Arg Ser Gly Thr Pro Phe Leu
                405                 410                 415

Thr Thr Gly Val Val Phe Ser Trp Thr His Arg Ser Ala Thr Leu Thr
            420                 425                 430

Asn Thr Ile Asp Pro Glu Arg Ile Asn Gln Ile Pro Leu Val Lys Gly
        435                 440                 445

Phe Arg Val Trp Gly Gly Thr Ser Val Val Thr Gly Pro Gly Phe Thr
    450                 455                 460

Gly Gly Asp Ile Leu Arg Arg Asn Thr Phe Gly Asp Phe Val Ser Leu
465                 470                 475                 480

Gln Val Asn Ile Asn Ser Pro Ile Thr Gln Arg Tyr Arg Leu Arg Phe
                485                 490                 495

Arg Tyr Ala Ser Ser Arg Asp Ala Arg Val Ile Val Leu Thr Gly Ala
            500                 505                 510

Ala Ser Thr Gly Val Gly Gly Gln Val Ser Val Asn Met Pro Leu Gln
        515                 520                 525

Lys Thr Met Glu Ile Gly Glu Asn Leu Thr Ser Arg Thr Phe Arg Tyr
    530                 535                 540

Thr Asp Phe Ser Asn Pro Phe Ser Phe Arg Ala Asn Pro Asp Thr Ile
545                 550                 555                 560

Gly Ile Ser Glu Gln Pro Leu Phe Gly Ala Gly Ser Ile Ser Ser Gly
                565                 570                 575

Glu Leu Tyr Ile Asp Lys Ile Glu Ile Ile Leu Ala Asp Ala Thr Phe
            580                 585                 590

Glu Ala Glu Ser Asp Leu Glu Arg
        595                 600
```

<210> SEQ ID NO 11
<211> LENGTH: 3546
<212> TYPE: DNA
<213> ORGANISM: Artificial Sequence
<220> FEATURE:
<223> OTHER INFORMATION: Cry1 variant

<400> SEQUENCE: 11

```
atgggacaca acaatccaaa tatcaatgaa tgcatcccct ataattgctt gagcaaccct     60
gaagttgaag ttctgggagg tgagaggata gaaactggat ataccccctat tgatatctct    120
ctgtctttga ctcagttcct cctgagtgag tttgttccag gtgcaggatt tgtgttgggt    180
ttggtagaca ttatctgggg aatctttgga ccatcccaat gggatgcctt tctggtccaa    240
atagagcaac tcataaacca gcgcattgag gaatttgcac gtaaccaggc aatctcccga    300
gttgagggat tgtcaaactt gtaccagata tatgctgaaa gtttcagaga gtgggaagct    360
gacccaacca accctgcatt gaaggaagag atgaggactc agttcaatga tatgaactca    420
gcactgacca ctgccatacc cttgtttgca gtacagaact atcaagtccc attactatca    480
gtctatgtgc aagcagcaaa cctacatttg agtgtcctcc gagatgtatc agtttttggt    540
caacgttggg gatttgatgc tgctaccatc aacagtcgtt acaatgacct cacacgactg    600
attgggaact acacagatca tgcagtccgt tggcacaata ctggattgga gagagtttgg    660
ggacctgata gtcgtgattg gattcgttac aatcagtttc gtcgggaact taccctgact    720
gtcttggata tagtgtcact gtttcctaac tatgatagtc gtacatatcc aatacgaaca    780
gcaagtcagc tgactcgtga aatctacacg aaccctgtcc tggagaactt tgatggtagc    840
ttccgtggat cagcacaagg catagagggt tccatccgga gtcctcatct catggacatc    900
ctgaacagca ttacaatcta cacagatgct catcgaggtg agtattactg gtcaggacac    960
caaatcatgg catccccagt tggattttct ggtccagagt tcactttccc cttgtatgga   1020
acaatgggta atgctgctcc acagcaacga atagttgctc aattgggaca aggggtatat   1080
cgaaccttat catcaacact gtatcgacgt ccattcaaca ttgggataaa caatcaacag   1140
ttgtctgtac tagatgggac agagtttgct tatggaactt cctccaacct cccttcagca   1200
gtttatcgga agtctgggac tgtagactca ctagatgaga tacctccaca gaataacaat   1260
gtacctccaa gacaaggatt ctcccaccgt ctctctcatg tgtctatgtt ccgtagtggc   1320
tttagtaaca gcagtgtgag catcatacgt gcacctatgt tttcatggat tcaccgtagt   1380
gcagagttca ataacaccat tgaccctgaa cgaatcaatc aaatcccact taccaaaagc   1440
accaaccttg gtagcggaac cagcgttgtg aagggtcctg gtttcactgg tggggatatt   1500
ctgcgacgta ccagccctgg acagattagc acactgcgtg tgaacatcac cgctccactg   1560
agtcagcgct atcgagtgag gattcgctat gctagcacta ccaaccttca gttccatacc   1620
agcattgatg gtcgtccaat taaccaaggc aacttcagcg ctaccatgtc cagcggctca   1680
aacctgcaaa gtggatcatt ccgcaccgtt ggctttacca ctccattcaa cttcagcaac   1740
ggcagtagcg tgttcaccct ttccgcacat gtgttcaaca gtggcaacga agtgtacatc   1800
gatagaatcg agtttgtgcc agcggaagtg acttttgaag ctgagtacga ccttgaacgt   1860
gcccaaaagg tcgttaacgc cctcttcact tcttccaacc agatcggatt gaaaacagat   1920
gttacagact accacattga ccaggtgtcc aatcttgtgg attgcttgtc tgatgagttc   1980
tgtctcgatg agaagcgaga actctctgaa aaggttaagc acgctaagag actcagcgat   2040
gaacgaaacc ttcttcagga cccaaatttc aggggaatta atagacaacc agatagaggt   2100
tggcgtggat caacagacat cactatccaa ggtggagacg atgtttttaa ggagaactac   2160
gtgacccttc ctggtactgt tgacgagtgc tatcctacct acctttacca gaagattgac   2220
gaatcaaagc tcaaagcata cactcgttat gagcttcgtg gttacatcga agattcacaa   2280
gatcttgaaa tctacctcat cagatacaac gctaaacacg aaatcgtcaa cgttccaggt   2340
```

-continued

```
actggatctc tgtggccact ctctgcacag tcacctattg gcaagtgcgg tgagccaaat   2400

agatgtgcac cacacctgga gtggaatccc gatctggact gtagttgtcg tgacggggag   2460

aagtgcgctc atcacagcca tcacttcact cttgatatcg atgttggatg taccgacctt   2520

aatgaagacc tgggcgtttg ggttatcttc aagattaaga cccaggatgg tcatgccaga   2580

cttggtaatc tggagttcct tgaagagaaa cccttgttgg gtgaagctct ggccagagtc   2640

aagcgtgctg agaagaaatg gcgtgataaa cgtgaaaagt tgcaattgga gactaacatt   2700

gtctacaaag aggcaaagga gtctgtggat gccttgttcg tgaactctca gtacgaccga   2760

ctccaagtgg ataccaacat tgctatgatt catgctgctg acaaacgtgt tcaccgtatc   2820

agagaagcct atctccctga actgtcagtg atcccaggag tcaacgctgc aatcttcgag   2880

gagcttgaag gtcgaatctt cactgcctat tcactttacg atgcacgaaa cgtgattaag   2940

aatggggatt ttaataacgg gttgttgtgc tggaatgtga aggggcacgt ggatgttgag   3000

gaacaaaaca accaccgttc cgtgcttgtt attcctgagt gggaagcaga ggtgtctcag   3060

gaggttaggg tgtgtcctgg tagaggatat atcttgagag tgactgccta taaggaaggc   3120

tatggtgaag gttgcgtgac aatccacgag atcgaagaca acacagatga gcttaagttc   3180

tctaactgcg ttgaggagga agtctaccca aacaataccg tcacttgtaa caattacaca   3240

ggcacacaag aagagtacga aggaacctac acctcccgaa atcagggtta tgatgaggcc   3300

tatggtaata atccttctgt gcctgccgat tatgcttctg tttacgagga aaagtcttac   3360

actgatggcc gtcgtgagaa cccttgcgaa tccaaccgtg gatacggtga ttacactcca   3420

cttccagcag gatacgttac taaggatctt gagtactttc cagagactga taaagtttgg   3480

atcgaaatcg gagagactga aggcacattc atcgtggatt ctgtggagct cttgctcatg   3540

gaggaa                                                              3546
```

<210> SEQ ID NO 12
<211> LENGTH: 591
<212> TYPE: PRT
<213> ORGANISM: Artificial Sequence
<220> FEATURE:
<223> OTHER INFORMATION: Cry1 variant

<400> SEQUENCE: 12

```
Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Ile Ile Trp Gly Ile Phe Gly Pro Ser Gln Trp Asp Ala Phe
        35                  40                  45

Leu Val Gln Ile Glu Gln Leu Ile Asn Gln Arg Ile Glu Glu Phe Ala
    50                  55                  60

Arg Asn Gln Ala Ile Ser Arg Val Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Lys Glu Glu Met Arg Thr Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
```

-continued

```
145                 150                 155                 160

Ile Asn Ser Arg Tyr Asn Asp Leu Thr Arg Leu Ile Gly Asn Tyr Thr
                165                 170                 175

Asp His Ala Val Arg Trp His Asn Thr Gly Leu Glu Arg Val Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Ala Ser Gln Leu Thr Arg Glu Ile Tyr
225                 230                 235                 240

Thr Asn Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575
```

-continued

Val Pro Ala Glu Val Thr Phe Glu Ala Glu Tyr Asp Leu Glu Arg
580 585 590

<210> SEQ ID NO 13
<211> LENGTH: 3546
<212> TYPE: DNA
<213> ORGANISM: Artificial Sequence
<220> FEATURE:
<223> OTHER INFORMATION: Cry1 variant

<400> SEQUENCE: 13
atgggacaca acaatccaaa tatcaatgaa tgcatcccct ataattgctt gagcaaccct 60
gaagttgaag ttctgggagg tgagaggata gaaactggat atacccctat tgatatctct 120
ctgtctttga ctcagttcct cctgagtgag tttgttccag gtgcaggatt tgtgttgggt 180
ttggtagaca ttatctgggg aatctttgga ccatcccaat gggatgcctt tctggtccaa 240
atagagcaac tcatatccca gcgcattgag gaatttgcac gtaaccaggc aatctcccga 300
gttgagggat tgtcaaactt gtaccagata tatgccgaaa gtttcagaga gtgggaagct 360
gacccaacca accctgcatt gaaagaagag atgaggattc agttcaatga tatgaactca 420
gcactgacca ctgccatacc cttgtttgca gtacagaact atcaagtccc attactatca 480
gtctatgtgc aagcagcaaa cctacatttg agtgtcctcc gagatgtatc agtttttggt 540
caacgttggg gatttgatgc tgctaccatc aacagtcgtt acaatgacct cacacgactg 600
attgggaact acacagatca tgcagtccgt tggtacaata ctggattgga gagagtttgg 660
ggacctgata gtcgtgattg gattcgttac aatcagtttc gtcgggaact taccctgact 720
gtcttggata tagtgtcact gtttcctaac tatgatagtc gtacatatcc aatacgaaca 780
gtcagtcagc tgactcgtga agtctacacg aaccctgtcc tggagaactt tgatgctagc 840
ttccgtggat cagcacaagg catagagggt tccatccgga gtcctcatct catggacatc 900
ctgaacagca ttacaatcta cacagatgct catcgaggtg agtattactg gtcaggacac 960
caaatcatgg catccccagt tggattttct ggtccagagt tcactttccc cttgtatgga 1020
acaatgggta atgctgctcc acagcaacga atagttgctc aattgggaca aggggtatat 1080
cgaaccttat catcaacact gtatcgacgt ccattcaaca ttgggataaa caatcaacag 1140
ttgtctgtac tagatgggac agagtttgct tatggaactt cctccaacct cccttcagca 1200
gtttatcgga agtctgggac tgtagactca ctagatgaga tacctccaca gaataacaat 1260
gtacctccaa gacaaggatt ctcccaccgt ctctctcatg tgtctatgtt ccgtagtggc 1320
tttagtaaca gcagtgtgag catcatacgt gcacctatgt tttcatggat tcaccgtagt 1380
gcagagttca ataacaccat tgaccctgaa cgaatcaatc aaatcccact taccaaaagc 1440
accaaccttg gtagcggaac cagcgttgtg aagggtcctg gtttcactgg tggggatatt 1500
ctgcgacgta ccagccctgg acagattagc acactgcgtg tgaacatcac cgctccactg 1560
agtcagcgct atcgagtgag gattcgctat gctagcacta ccaaccttca gttccatacc 1620
agcattgatg gtcgtccaat taaccaaggc aacttcagcg ctaccatgtc cagcggctca 1680
aacctgcaaa gtggatcatt ccgcaccgtt ggctttacca ctccattcaa cttcagcaac 1740
ggcagtagcg tgttcaccct ttccgcacat gtgttcaaca gtggcaacga agtgtacatc 1800
gatagaatcg agtttgtgcc agcggaagtg acttttgaag ctgagtacga ccttgaacgt 1860
gcccaaaagg tcgttaacgc cctcttcact tcttccaacc agatcggatt gaaaacagat 1920
gttacagact accacattga ccaggtgtcc aatcttgtgg attgcttgtc tgatgagttc 1980
tgtctcgatg agaagcgaga actctctgaa aaggttaagc acgctaagag actcagcgat 2040

-continued

```
gaacgaaacc ttcttcagga cccaaatttc aggggaatta atagacaacc agatagaggt   2100

tggcgtggat caacagacat cactatccaa ggtggagacg atgtttttaa ggagaactac   2160

gtgacccttc ctggtactgt tgacgagtgc tatcctacct acctttacca gaagattgac   2220

gaatcaaagc tcaaagcata cactcgttat gagcttcgtg gttacatcga agattcacaa   2280

gatcttgaaa tctacctcat cagatacaac gctaaacacg aaatcgtcaa cgttccaggt   2340

actggatctc tgtggccact ctctgcacag tcacctattg gcaagtgcgg tgagccaaat   2400

agatgtgcac cacacctgga gtggaatccc gatctggact gtagttgtcg tgacggggag   2460

aagtgcgctc atcacagcca tcacttcact cttgatatcg atgttggatg taccgacctt   2520

aatgaagacc tgggcgtttg ggttatcttc aagattaaga cccaggatgg tcatgccaga   2580

cttggtaatc tggagttcct tgaagagaaa cccttgttgg gtgaagctct ggccagagtc   2640

aagcgtgctg agaagaaatg gcgtgataaa cgtgaaaagt tgcaattgga gactaacatt   2700

gtctacaaag aggcaaagga gtctgtggat gccttgttcg tgaactctca gtacgaccga   2760

ctccaagtgg ataccaacat tgctatgatt catgctgctg acaaacgtgt tcaccgtatc   2820

agagaagcct atctccctga actgtcagtg atcccaggag tcaacgctgc aatcttcgag   2880

gagcttgaag gtcgaatctt cactgcctat tcactttacg atgcacgaaa cgtgattaag   2940

aatggggatt ttaataacgg gttgttgtgc tggaatgtga aggggcacgt ggatgttgag   3000

gaacaaaaca accaccgttc cgtgcttgtt attcctgagt gggaagcaga ggtgtctcag   3060

gaggttaggg tgtgtcctgg tagaggatat atcttgagag tgactgccta taaggaaggc   3120

tatggtgaag gttgcgtgac aatccacgag atcgaagaca acacagatga gcttaagttc   3180

tctaactgcg ttgaggagga agtctaccca aacaataccg tcacttgtaa caattacaca   3240

ggcacacaag aagagtacga aggaacctac acctcccgaa atcagggtta tgatgaggcc   3300

tatggtaata atccttctgt gcctgccgat tatgcttctg tttacgagga aaagtcttac   3360

actgatggcc gtcgtgagaa cccttgcgaa tccaaccgtg gatacggtga ttacactcca   3420

cttccagcag gatacgttac taaggatctt gagtactttc cagagactga taaagtttgg   3480

atcgaaatcg gagagactga aggcacattc atcgtggatt ctgtggagct cttgctcatg   3540

gaggaa                                                              3546
```

<210> SEQ ID NO 14
<211> LENGTH: 591
<212> TYPE: PRT
<213> ORGANISM: Artificial Sequence
<220> FEATURE:
<223> OTHER INFORMATION: Cry1 variant

<400> SEQUENCE: 14

```
Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Ile Ile Trp Gly Ile Phe Gly Pro Ser Gln Trp Asp Ala Phe
        35                  40                  45

Leu Val Gln Ile Glu Gln Leu Ile Ser Gln Arg Ile Glu Glu Phe Ala
    50                  55                  60

Arg Asn Gln Ala Ile Ser Arg Val Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95
```

```
Ala Leu Lys Glu Glu Met Arg Ile Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Tyr Thr
                165                 170                 175

Asp His Ala Val Arg Trp Tyr Asn Thr Gly Leu Glu Arg Val Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Val Ser Gln Leu Thr Arg Glu Val Tyr
225                 230                 235                 240

Thr Asn Pro Val Leu Glu Asn Phe Asp Ala Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
```

-continued

```
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590
```

<210> SEQ ID NO 15
<211> LENGTH: 3546
<212> TYPE: DNA
<213> ORGANISM: Artificial Sequence
<220> FEATURE:
<223> OTHER INFORMATION: Cry1 variant

<400> SEQUENCE: 15

```
atgggacaca acaatccaaa tatcaatgaa tgcatcccct ataattgctt gagcaaccct     60

gaagttgaag ttctgggagg tgagaggata gaaactggat ataccccctat tgatatctct    120

ctgtctttga ctcagttcct cctgagtgag tttgttccag gtgcaggatt tgtgttgggt    180

ttggtagacg ttatctgggg agttttcgga ccatcccaat gggatgcctt tctggtccaa    240

atagagcaac tcataaacca gcgcattgag gaatttgcac gtaaccaggc aatctcccga    300

gttgagggat tgtcaaactt gtaccagata tatgctgaaa gtttcagaga gtgggaagct    360

gacccaacca accctgcatt gaaggaagag atgaggactc agttcaatga tatgaactca    420

gcactgacca ctgccatacc cttgtttgca gtacagaact atcaagtccc attactatca    480

gtctatgtgc aagcagcaaa cctacatttg agtgtcctcc gagatgtttc agttttcggt    540

caacgttggg gatttgatgc tgctaccatc aacagtcgtt acaatgacct cacacgactg    600

attgggaact acacagatca tgcagtccgt tggcacaata ctggattggg gagagtttgg    660

ggacctgata gtcgtgattg gattcgttac aatcagtttc gtcgggaact taccctgact    720

gtcttggata tagtgtcact gtttcctaac tatgatagtc gtacatatcc aatacgaaca    780

gcaagtcagc tgactcgtga aatctacacg aaccctgtcc tggagaactt tgatggtaac    840

ttccgtggat cagcacaagg catagagggt tccatccgga gtcctcatct catggacatc    900

ctgaacagca ttacaatcta cacagatgct catcgaggtg agtattactg gtcaggacac    960

caaatcatgg catccccagt tggattttct ggtccagagt tcactttccc cttgtatgga   1020

acaatgggta atgctgctcc acagcaacga atagttgctc aattgggaca aggggtatat   1080

cgaaccttat catcaacact gtatcgacgt ccattcaaca ttgggataaa caatcaacag   1140

ttgtctgtac tagatgggac agagtttgct tatggaactt cctccaacct cccttcagca   1200

gtttatcgga agtctgggac tgtagactca ctagatgaga tacctccaca gaataacaat   1260

gtacctccaa gacaaggatt ctcccaccgt ctctctcatg tgtctatgtt ccgtagtggc   1320

tttagtaaca gcagtgtgag catcatacgt gcacctatgt tttcatggat tcaccgtagt   1380

gcagagttca ataacaccat tgaccctgaa cgaatcaatc aaatccccact taccaaaagc   1440

accaaccttg gtagcggaac cagcgttgtg aagggtcctg gtttcactgg tggggatatt   1500

ctgcgacgta ccagccctgg acagattagc acactgcgtg tgaacatcac cgctccactg   1560

agtcagcgct atcgagtgag gattcgctat gctagcacta ccaaccttca gttccatacc   1620

agcattgatg gtcgtccaat taaccaaggc aacttcagcg ctaccatgtc cagcggctca   1680
```

-continued

```
aacctgcaaa gtggatcatt ccgcaccgtt ggctttacca ctccattcaa cttcagcaac   1740
ggcagtagcg tgttcaccct ttccgcacat gtgttcaaca gtggcaacga agtgtacatc   1800
gatagaatcg agtttgtgcc agcggaagtg acttttgaag ctgagtacga ccttgaacgt   1860
gcccaaaagg tcgttaacgc cctcttcact tcttccaacc agatcggatt gaaaacagat   1920
gttacagact accacattga ccaggtgtcc aatcttgtgg attgcttgtc tgatgagttc   1980
tgtctcgatg agaagcgaga actctctgaa aaggttaagc acgctaagag actcagcgat   2040
gaacgaaacc ttcttcagga cccaaatttc aggggaatta atagacaacc agatagaggt   2100
tggcgtggat caacagacat cactatccaa ggtggagacg atgtttttaa ggagaactac   2160
gtgacccttc ctggtactgt tgacgagtgc tatcctacct acctttacca gaagattgac   2220
gaatcaaagc tcaaagcata cactcgttat gagcttcgtg gttacatcga agattcacaa   2280
gatcttgaaa tctacctcat cagatacaac gctaaacacg aaatcgtcaa cgttccaggt   2340
actggatctc tgtggccact ctctgcacag tcacctattg gcaagtgcgg tgagccaaat   2400
agatgtgcac cacacctgga gtggaatccc gatctggact gtagttgtcg tgacggggag   2460
aagtgcgctc atcacagcca tcacttcact cttgatatcg atgttggatg taccgacctt   2520
aatgaagacc tgggcgtttg ggttatcttc aagattaaga cccaggatgg tcatgccaga   2580
cttggtaatc tggagttcct tgaagagaaa cccttgttgg gtgaagctct ggccagagtc   2640
aagcgtgctg agaagaaatg gcgtgataaa cgtgaaaagt tgcaattgga gactaacatt   2700
gtctacaaag aggcaaagga gtctgtggat gccttgttcg tgaactctca gtacgaccga   2760
ctccaagtgg ataccaacat tgctatgatt catgctgctg acaaacgtgt tcaccgtatc   2820
agagaagcct atctccctga actgtcagtg atcccaggag tcaacgctgc aatcttcgag   2880
gagcttgaag gtcgaatctt cactgcctat tcactttacg atgcacgaaa cgtgattaag   2940
aatggggatt ttaataacgg gttgttgtgc tggaatgtga aggggcacgt ggatgttgag   3000
gaacaaaaca accaccgttc cgtgcttgtt attcctgagt gggaagcaga ggtgtctcag   3060
gaggttaggg tgtgtcctgg tagaggatat atcttgagag tgactgccta taaggaaggc   3120
tatggtgaag gttgcgtgac aatccacgag atcgaagaca acacagatga gcttaagttc   3180
tctaactgcg ttgaggagga agtctaccca aacaataccg tcacttgtaa caattacaca   3240
ggcacacaag aagagtacga aggaacctac acctcccgaa atcagggtta tgatgaggcc   3300
tatggtaata atccttctgt gcctgccgat tatgcttctg tttacgagga aaagtcttac   3360
actgatggcc gtcgtgagaa cccttgcgaa tccaaccgtg gatacggtga ttacactcca   3420
cttccagcag gatacgttac taaggatctt gagtactttc cagagactga taaagtttgg   3480
atcgaaatcg gagagactga aggcacattc atcgtggatt ctgtggagct cttgctcatg   3540
gaggaa                                                              3546
```

```
<210> SEQ ID NO 16
<211> LENGTH: 591
<212> TYPE: PRT
<213> ORGANISM: Artificial Sequence
<220> FEATURE:
<223> OTHER INFORMATION: Cry1 variant

<400> SEQUENCE: 16

Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30
```

-continued

```
Val Asp Val Ile Trp Gly Val Phe Gly Pro Ser Gln Trp Asp Ala Phe
        35                  40                  45

Leu Val Gln Ile Glu Gln Leu Ile Asn Gln Arg Ile Glu Glu Phe Ala
    50                  55                  60

Arg Asn Gln Ala Ile Ser Arg Val Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Lys Glu Glu Met Arg Thr Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Tyr Thr
                165                 170                 175

Asp His Ala Val Arg Trp His Asn Thr Gly Leu Gly Arg Val Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Ala Ser Gln Leu Thr Arg Glu Ile Tyr
225                 230                 235                 240

Thr Asn Pro Val Leu Glu Asn Phe Asp Gly Asn Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460
```

```
Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590


<210> SEQ ID NO 17
<211> LENGTH: 3546
<212> TYPE: DNA
<213> ORGANISM: Artificial Sequence
<220> FEATURE:
<223> OTHER INFORMATION: Cry1 variant

<400> SEQUENCE: 17

atgggacaca acaatccaaa tatcaatgaa tgcatcccct ataattgctt gagcaaccct     60

gaagttgaag ttctgggagg tgagaggata gaaactggat ataccccctat tgatatctct    120

ctgtctttga ctcagttcct cctgagtgag tttgttccag gtgcaggatt tgtgttgggt    180

ttggtagacg ttatctgggg aatctttgga ccatcccaat gggatgcctt tctggtccaa    240

atagagcaac tcataaacca gcgcattgag gaatttgcac gtaaccaggc aatctcccga    300

gttgagggat tgtcaaactt gtaccagata tatgctgaaa gtttcagaga gtgggaagct    360

gacccaacca accctgcatt gaaggaagag atgaggactc agttcaatga tatgaactca    420

gcactgacca ctgccatacc cttgtttgca gtacagaact atcaagtccc attactatca    480

gtctatgtgc aagcagcaaa cctacatttg agtgtcctcc gagatgtatc agtttttggt    540

caacgttggg gatttgatgc tgctaccatc aacagtcgtt acaatgacct cacacgactg    600

attgggaact tcacagatca tgcagtccgt tggcacaata ctggattgga gagaatctgg    660

ggacctgata gtcgtgattg gattcgttac aatcagtttc gtcgggaact taccctgact    720

gtcttggata tagtgtcact gtttcctaac tatgatagtc gtacatatcc aatacgaaca    780

gcaagtcagc tgactcgtga aatctacacg aaccctgtcc tggagaactt tgatggtagc    840

ttccgtggat cagcacaagg catagagggt tccatccgga gtcctcatct catggacatc    900

ctgaacagca ttacaatcta cacagatgct catcgaggtg agtattactg gtcaggacac    960

caaatcatgg catccccagt tggattttct ggtccagagt tcactttccc cttgtatgga   1020

acaatgggta atgctgctcc acagcaacga atagttgctc aattgggaca aggggtatat   1080

cgaaccttat catcaacact gtatcgacgt ccattcaaca ttgggataaa caatcaacag   1140

ttgtctgtac tagatgggac agagtttgct tatggaactt cctccaacct cccttcagca   1200

gtttatcgga agtctgggac tgtagactca ctagatgaga tacctccaca gaataacaat   1260

gtacctccaa gacaaggatt ctcccaccgt ctctctcatg tgtctatgtt ccgtagtggc   1320

tttagtaaca gcagtgtgag catcatacgt gcacctatgt tttcatggat tcaccgtagt   1380
```

```
gcagagttca ataacaccat tgaccctgaa cgaatcaatc aaatcccact taccaaaagc   1440

accaaccttg gtagcggaac cagcgttgtg aagggtcctg gtttcactgg tggggatatt   1500

ctgcgacgta ccagccctgg acagattagc acactgcgtg tgaacatcac cgctccactg   1560

agtcagcgct atcgagtgag gattcgctat gctagcacta ccaaccttca gttccatacc   1620

agcattgatg gtcgtccaat taaccaaggc aacttcagcg ctaccatgtc cagcggctca   1680

aacctgcaaa gtggatcatt ccgcaccgtt ggctttacca ctccattcaa cttcagcaac   1740

ggcagtagcg tgttcaccct ttccgcacat gtgttcaaca gtggcaacga agtgtacatc   1800

gatagaatcg agtttgtgcc agcggaagtg acttttgaag ctgagtacga ccttgaacgt   1860

gcccaaaagg tcgttaacgc cctcttcact tcttccaacc agatcggatt gaaaacagat   1920

gttacagact accacattga ccaggtgtcc aatcttgtgg attgcttgtc tgatgagttc   1980

tgtctcgatg agaagcgaga actctctgaa aaggttaagc acgctaagag actcagcgat   2040

gaacgaaacc ttcttcagga cccaaatttc aggggaatta atagacaacc agatagaggt   2100

tggcgtggat caacagacat cactatccaa ggtggagacg atgtttttaa ggagaactac   2160

gtgacccttc ctggtactgt tgacgagtgc tatcctacct acctttacca gaagattgac   2220

gaatcaaagc tcaaagcata cactcgttat gagcttcgtg gttacatcga agattcacaa   2280

gatcttgaaa tctacctcat cagatacaac gctaaacacg aaatcgtcaa cgttccaggt   2340

actggatctc tgtggccact ctctgcacag tcacctattg gcaagtgcgg tgagccaaat   2400

agatgtgcac cacacctgga gtggaatccc gatctggact gtagttgtcg tgacggggag   2460

aagtgcgctc atcacagcca tcacttcact cttgatatcg atgttggatg taccgacctt   2520

aatgaagacc tgggcgtttg ggttatcttc aagattaaga cccaggatgg tcatgccaga   2580

cttggtaatc tggagttcct tgaagagaaa cccttgttgg gtgaagctct ggccagagtc   2640

aagcgtgctg agaagaaatg gcgtgataaa cgtgaaaagt tgcaattgga gactaacatt   2700

gtctacaaag aggcaaagga gtctgtggat gccttgttcg tgaactctca gtacgaccga   2760

ctccaagtgg ataccaacat tgctatgatt catgctgctg acaaacgtgt tcaccgtatc   2820

agagaagcct atctccctga actgtcagtg atcccaggag tcaacgctgc aatcttcgag   2880

gagcttgaag gtcgaatctt cactgcctat tcactttacg atgcacgaaa cgtgattaag   2940

aatggggatt ttaataacgg gttgttgtgc tggaatgtga aggggcacgt ggatgttgag   3000

gaacaaaaca accaccgttc cgtgcttgtt attcctgagt gggaagcaga ggtgtctcag   3060

gaggttaggg tgtgtcctgg tagaggatat atcttgagag tgactgccta taaggaaggc   3120

tatggtgaag gttgcgtgac aatccacgag atcgaagaca acacagatga gcttaagttc   3180

tctaactgcg ttgaggagga agtctaccca aacaataccg tcacttgtaa caattacaca   3240

ggcacacaag aagagtacga aggaacctac acctcccgaa atcagggtta tgatgaggcc   3300

tatggtaata atccttctgt gcctgccgat tatgcttctg tttacgagga aaagtcttac   3360

actgatggcc gtcgtgagaa cccttgcgaa tccaaccgtg gatacggtga ttacactcca   3420

cttccagcag gatacgttac taaggatctt gagtactttc cagagactga taaagtttgg   3480

atcgaaatcg gagagactga aggcacattc atcgtggatt ctgtggagct cttgctcatg   3540

gaggaa                                                              3546
```

<210> SEQ ID NO 18
<211> LENGTH: 591
<212> TYPE: PRT
<213> ORGANISM: Artificial Sequence

```
<220> FEATURE:
<223> OTHER INFORMATION: Cry1 variant

<400> SEQUENCE: 18

Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Val Ile Trp Gly Ile Phe Gly Pro Ser Gln Trp Asp Ala Phe
        35                  40                  45

Leu Val Gln Ile Glu Gln Leu Ile Asn Gln Arg Ile Glu Glu Phe Ala
    50                  55                  60

Arg Asn Gln Ala Ile Ser Arg Val Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Lys Glu Glu Met Arg Thr Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Phe Thr
                165                 170                 175

Asp His Ala Val Arg Trp His Asn Thr Gly Leu Glu Arg Ile Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Ala Ser Gln Leu Thr Arg Glu Ile Tyr
225                 230                 235                 240

Thr Asn Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400
```

```
Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590


<210> SEQ ID NO 19
<211> LENGTH: 3546
<212> TYPE: DNA
<213> ORGANISM: Artificial Sequence
<220> FEATURE:
<223> OTHER INFORMATION: Cry1 variant

<400> SEQUENCE: 19

atgggacaca acaatccaaa tatcaatgaa tgcatcccct ataattgctt gagcaaccct     60

gaagttgaag ttctgggagg tgagaggata gaaactggat atacccctat tgatatctct    120

ctgtctttga ctcagttcct cctgagtgag tttgttccag gtgcaggatt tgtgttgggt    180

ttggtagaca ttatctgggg aatctttgga ccatcccaat gggatgcctt tctggtccaa    240

atagagcaac tcgtgaacca gcgcattgag gaatttgcac gtaaccaggc aatctcccga    300

gttgagggat tgtcaaactt gtaccaggtt tatgctgaaa gtttcagaga gtgggaagct    360

gacccaacca accctgcatt gaaggaagag atgaggactc agttcaatga tatgaactca    420

gcactgacca ctgccatacc cttgtttgca gtacagaact atcaagtccc attactatca    480

gtctatgtgc aagcagcaaa cctacatttg agtgtcctcc gagatgtatc agtttttggt    540

caacgttggg gatttgatgc tgctaccatc aacagtcgtt acaatgacct cacacgactg    600

attgggaact acacagatca tgcagtccgt tggcacaata ctggattgga gagaatctgg    660

ggacctgata gtcgtgattg gattcgttac aatcagtttc gtcgggaact taccctgact    720

gtcttggata tagtgtcact gtttcctaac tatgatagtc gtacatatcc aatacgaaca    780

gcaagtcagc tgactcgtga aatctacacg aaccctgtcc tggagaactt tgatggtagc    840

ttccgtggat cagcacaagg catagagggt tccatccgga gtcctcatct catggacatc    900

ctgaacagca ttacaatcta cacagatgct catcgaggtg agtattactg gtcaggacac    960

caaatcatgg catccccagt tggattttct ggtccagagt tcactttccc cttgtatgga   1020
```

-continued

```
acaatgggta atgctgctcc acagcaacga atagttgctc aattgggaca aggggtatat   1080
cgaaccttat catcaacact gtatcgacgt ccattcaaca ttgggataaa caatcaacag   1140
ttgtctgtac tagatgggac agagtttgct tatggaactt cctccaacct cccttcagca   1200
gtttatcgga agtctgggac tgtagactca ctagatgaga tacctccaca gaataacaat   1260
gtacctccaa gacaaggatt ctcccaccgt ctctctcatg tgtctatgtt ccgtagtggc   1320
tttagtaaca gcagtgtgag catcatacgt gcacctatgt tttcatggat tcaccgtagt   1380
gcagagttca ataacaccat tgaccctgaa cgaatcaatc aaatcccact taccaaaagc   1440
accaaccttg gtagcggaac cagcgttgtg aagggtcctg gtttcactgg tggggatatt   1500
ctgcgacgta ccagccctgg acagattagc acactgcgtg tgaacatcac cgctccactg   1560
agtcagcgct atcgagtgag gattcgctat gctagcacta ccaaccttca gttccatacc   1620
agcattgatg gtcgtccaat taaccaaggc aacttcagcg ctaccatgtc cagcggctca   1680
aacctgcaaa gtggatcatt ccgcaccgtt ggctttacca ctccattcaa cttcagcaac   1740
ggcagtagcg tgttcaccct ttccgcacat gtgttcaaca gtggcaacga agtgtacatc   1800
gatagaatcg agtttgtgcc agcggaagtg acttttgaag ctgagtacga ccttgaacgt   1860
gcccaaaagg tcgttaacgc cctcttcact tcttccaacc agatcggatt gaaaacagat   1920
gttacagact accacattga ccaggtgtcc aatcttgtgg attgcttgtc tgatgagttc   1980
tgtctcgatg agaagcgaga actctctgaa aaggttaagc acgctaagag actcagcgat   2040
gaacgaaacc ttcttcagga cccaaatttc aggggaatta atagacaacc agatagaggt   2100
tggcgtggat caacagacat cactatccaa ggtggagacg atgtttttaa ggagaactac   2160
gtgacccttc ctggtactgt tgacgagtgc tatcctacct acctttacca gaagattgac   2220
gaatcaaagc tcaaagcata cactcgttat gagcttcgtg gttacatcga agattcacaa   2280
gatcttgaaa tctacctcat cagatacaac gctaaacacg aaatcgtcaa cgttccaggt   2340
actggatctc tgtggccact ctctgcacag tcacctattg gcaagtgcgg tgagccaaat   2400
agatgtgcac cacacctgga gtggaatccc gatctggact gtagttgtcg tgacggggag   2460
aagtgcgctc atcacagcca tcacttcact cttgatatcg atgttggatg taccgacctt   2520
aatgaagacc tgggcgtttg ggttatcttc aagattaaga cccaggatgg tcatgccaga   2580
cttggtaatc tggagttcct tgaagagaaa cccttgttgg gtgaagctct ggccagagtc   2640
aagcgtgctg agaagaaatg gcgtgataaa cgtgaaaagt tgcaattgga gactaacatt   2700
gtctacaaag aggcaaagga gtctgtggat gccttgttcg tgaactctca gtacgaccga   2760
ctccaagtgg ataccaacat tgctatgatt catgctgctg acaaacgtgt tcaccgtatc   2820
agagaagcct atctccctga actgtcagtg atcccaggag tcaacgctgc aatcttcgag   2880
gagcttgaag gtcgaatctt cactgcctat tcactttacg atgcacgaaa cgtgattaag   2940
aatggggatt ttaataacgg gttgttgtgc tggaatgtga aggggcacgt ggatgttgag   3000
gaacaaaaca accaccgttc cgtgcttgtt attcctgagt gggaagcaga ggtgtctcag   3060
gaggttaggg tgtgtcctgg tagaggatat atcttgagag tgactgccta taaggaaggc   3120
tatggtgaag gttgcgtgac aatccacgag atcgaagaca acacagatga gcttaagttc   3180
tctaactgcg ttgaggagga agtctaccca aacaataccg tcacttgtaa caattacaca   3240
ggcacacaag aagagtacga aggaacctac acctcccgaa atcagggtta tgatgaggcc   3300
tatggtaata atccttctgt gcctgccgat tatgcttctg tttacgagga aaagtcttac   3360
actgatggcc gtcgtgagaa cccttgcgaa tccaaccgtg gatacggtga ttacactcca   3420
```

```
cttccagcag gatacgttac taaggatctt gagtactttc cagagactga taaagtttgg   3480

atcgaaatcg gagagactga aggcacattc atcgtggatt ctgtggagct cttgctcatg   3540

gaggaa                                                              3546


<210> SEQ ID NO 20
<211> LENGTH: 591
<212> TYPE: PRT
<213> ORGANISM: Artificial Sequence
<220> FEATURE:
<223> OTHER INFORMATION: Cry1 variant

<400> SEQUENCE: 20

Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Ile Ile Trp Gly Ile Phe Gly Pro Ser Gln Trp Asp Ala Phe
        35                  40                  45

Leu Val Gln Ile Glu Gln Leu Val Asn Gln Arg Ile Glu Glu Phe Ala
    50                  55                  60

Arg Asn Gln Ala Ile Ser Arg Val Glu Gly Leu Ser Asn Leu Tyr Gln
65                  70                  75                  80

Val Tyr Ala Glu Ser Phe Arg Glu Trp Glu Ala Asp Pro Thr Asn Pro
                85                  90                  95

Ala Leu Lys Glu Glu Met Arg Thr Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Tyr Thr
                165                 170                 175

Asp His Ala Val Arg Trp His Asn Thr Gly Leu Glu Arg Ile Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Ala Ser Gln Leu Thr Arg Glu Ile Tyr
225                 230                 235                 240

Thr Asn Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
```

```
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590
```

<210> SEQ ID NO 21
<211> LENGTH: 3546
<212> TYPE: DNA
<213> ORGANISM: Artificial Sequence
<220> FEATURE:
<223> OTHER INFORMATION: Cry1 variant

<400> SEQUENCE: 21

```
atgggacaca acaatccaaa tatcaatgaa tgcatcccct ataattgctt gagcaaccct     60

gaagttgaag ttctgggagg tgagaggata gaaactggat atacccctat tgatatctct    120

ctgtctttga ctcagttcct cctgagtgag tttgttccag gtgcaggatt tgtgttgggt    180

ttggtagacg ttatctgggg aatctttgga ccatcccaat gggatgcctt tctggtccaa    240

atagagcaac tcataaacca gcgcattgag gaattcgcac gtaaccaggc aatctcccga    300

gttgagggat tgtcaaactt gtaccagata tatgctgaaa gtttcagaga gtgggaagct    360

gacccaacca accctgcatt gaaggaagag atgaggactc agttcaatga tatgaactca    420

gcactgacca ctgccatacc cttgtttgca gtacagaact atcaagtccc attactatca    480

gtctatgtgc aagcagcaaa cctacatttg agtgtcctcc gagatgtatc agtttttggt    540

caacgttggg gatttgatgc tgctaccatc aacagtcgtt acaatgacct cacacgactg    600

attgggaact acacagatca tgcagtccgt tggcacaata ctggattgga gagaatctgg    660

ggacctgata gtcgtgattg gattcgttac aatcagtttc gtcgggaact taccctgact    720
```

```
gttttggata tagtgtcact gtttcctaac tatgatagtc gtacatatcc aatacgaaca    780
gcaagtcagc tgactcgtga aatctacacg aaccctgtcc tggagaactt tgatggtagc    840
ttccgtggat cagcacaagg catagagggt tccatccgga gtcctcatct catggacatc    900
ctgaacagca ttacaatcta cacagatgct catcgaggtg agtattactg gtcaggacac    960
caaatcatgg catccccagt tggattttct ggtccagagt tcactttccc cttgtatgga   1020
acaatgggta atgctgctcc acagcaacga atagttgctc aattgggaca aggggtatat   1080
cgaaccttat catcaacact gtatcgacgt ccattcaaca ttgggataaa caatcaacag   1140
ttgtctgtac tagatgggac agagtttgct tatggaactt cctccaacct cccttcagca   1200
gtttatcgga agtctgggac tgtagactca ctagatgaga tacctccaca gaataacaat   1260
gtacctccaa gacaaggatt ctcccaccgt ctctctcatg tgtctatgtt ccgtagtggc   1320
tttagtaaca gcagtgtgag catcatacgt gcacctatgt tttcatggat tcaccgtagt   1380
gcagagttca ataacaccat tgaccctgaa cgaatcaatc aaatcccact taccaaaagc   1440
accaaccttg gtagcggaac cagcgttgtg aagggtcctg gtttcactgg tggggatatt   1500
ctgcgacgta ccagccctgg acagattagc acactgcgtg tgaacatcac cgctccactg   1560
agtcagcgct atcgagtgag gattcgctat gctagcacta ccaaccttca gttccatacc   1620
agcattgatg gtcgtccaat taaccaaggc aacttcagcg ctaccatgtc cagcggctca   1680
aacctgcaaa gtggatcatt ccgcaccgtt ggctttacca ctccattcaa cttcagcaac   1740
ggcagtagcg tgttcaccct ttccgcacat gtgttcaaca gtggcaacga agtgtacatc   1800
gatagaatcg agtttgtgcc agcggaagtg acttttgaag ctgagtacga ccttgaacgt   1860
gcccaaaagg tcgttaacgc cctcttcact tcttccaacc agatcggatt gaaaacagat   1920
gttacagact accacattga ccaggtgtcc aatcttgtgg attgcttgtc tgatgagttc   1980
tgtctcgatg agaagcgaga actctctgaa aaggttaagc acgctaagag actcagcgat   2040
gaacgaaacc ttcttcagga cccaaatttc aggggaatta atagacaacc agatagaggt   2100
tggcgtggat caacagacat cactatccaa ggtggagacg atgtttttaa ggagaactac   2160
gtgacccttc ctggtactgt tgacgagtgc tatcctacct acctttacca gaagattgac   2220
gaatcaaagc tcaaagcata cactcgttat gagcttcgtg gttacatcga agattcacaa   2280
gatcttgaaa tctacctcat cagatacaac gctaaacacg aaatcgtcaa cgttccaggt   2340
actggatctc tgtggccact ctctgcacag tcacctattg gcaagtgcgg tgagccaaat   2400
agatgtgcac cacacctgga gtggaatccc gatctggact gtagttgtcg tgacggggag   2460
aagtgcgctc atcacagcca tcacttcact cttgatatcg atgttggatg taccgacctt   2520
aatgaagacc tgggcgtttg ggttatcttc aagattaaga cccaggatgg tcatgccaga   2580
cttggtaatc tggagttcct tgaagagaaa cccttgttgg gtgaagctct ggccagagtc   2640
aagcgtgctg agaagaaatg gcgtgataaa cgtgaaaagt tgcaattgga gactaacatt   2700
gtctacaaag aggcaaagga gtctgtggat gccttgttcg tgaactctca gtacgaccga   2760
ctccaagtgg ataccaacat tgctatgatt catgctgctg acaaacgtgt tcaccgtatc   2820
agagaagcct atctccctga actgtcagtg atcccaggag tcaacgctgc aatcttcgag   2880
gagcttgaag gtcgaatctt cactgcctat tcactttacg atgcacgaaa cgtgattaag   2940
aatggggatt ttaataacgg gttgttgtgc tggaatgtga aggggcacgt ggatgttgag   3000
gaacaaaaca accaccgttc cgtgcttgtt attcctgagt gggaagcaga ggtgtctcag   3060
gaggttaggg tgtgtcctgg tagaggatat atcttgagag tgactgccta taaggaaggc   3120
```

```
tatggtgaag gttgcgtgac aatccacgag atcgaagaca acacagatga gcttaagttc   3180

tctaactgcg ttgaggagga agtctaccca aacaataccg tcacttgtaa caattacaca   3240

ggcacacaag aagagtacga aggaacctac acctcccgaa atcagggtta tgatgaggcc   3300

tatggtaata atccttctgt gcctgccgat tatgcttctg tttacgagga aaagtcttac   3360

actgatggcc gtcgtgagaa cccttgcgaa tccaaccgtg gatacggtga ttacactcca   3420

cttccagcag gatacgttac taaggatctt gagtactttc cagagactga taaagtttgg   3480

atcgaaatcg gagagactga aggcacattc atcgtggatt ctgtggagct cttgctcatg   3540

gaggaa                                                              3546
```

<210> SEQ ID NO 22
<211> LENGTH: 591
<212> TYPE: PRT
<213> ORGANISM: Artificial Sequence
<220> FEATURE:
<223> OTHER INFORMATION: Cry1 variant

<400> SEQUENCE: 22

```
Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Val Ile Trp Gly Ile Phe Gly Pro Ser Gln Trp Asp Ala Phe
        35                  40                  45

Leu Val Gln Ile Glu Gln Leu Ile Asn Gln Arg Ile Glu Glu Phe Ala
    50                  55                  60

Arg Asn Gln Ala Ile Ser Arg Val Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Lys Glu Glu Met Arg Thr Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Tyr Thr
                165                 170                 175

Asp His Ala Val Arg Trp His Asn Thr Gly Leu Glu Arg Ile Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Ala Ser Gln Leu Thr Arg Glu Ile Tyr
225                 230                 235                 240

Thr Asn Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285
```

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590

<210> SEQ ID NO 23
<211> LENGTH: 3546
<212> TYPE: DNA
<213> ORGANISM: Artificial Sequence
<220> FEATURE:
<223> OTHER INFORMATION: Cry1 variant

<400> SEQUENCE: 23
atgggacaca acaatccaaa tatcaatgaa tgcatcccct ataattgctt gagcaaccct 60
gaagttgaag ttctgggagg tgagaggata gaaactggat atacccctat tgatatctct 120
ctgtctttga ctcagttcct cctgagtgag tttgttccag gtgcaggatt tgtgttgggt 180
ttggtagaca ttatctgggg aatctttgga ccatcccaat gggatgcctt tctggtccaa 240
atagagcaac tcataaacca gcgcattgag gaatttgcac gtaaccaggc aatctcccga 300
gttgagggat tgtcaaactt gtaccagata tatgctgaaa gtttcagaga gtgggaagct 360

-continued

```
gacccaacca accctgcatt gaaggaagag atgaggactc agttcaatga tatgaactca    420
gcactgacca ctgccatacc cttgtttgca gtacagaact atcaagtccc attactatca    480
gttttcgtgc aagcagcaaa cctacatttg agtgtcctcc gagatgtatc agttttcggt    540
caacgttggg gatttgatgc tgctaccatc aacagtcgtt acaatgacct cacacgactg    600
attgggaact tcacagatca tgcagtccgt tggcacaata ctggattgga gagaatctgg    660
ggacctgata gtcgtgattg gattcgttac aatcagtttc gtcgggaact taccctgact    720
gtcttggata tagtgtcact gtttcctaac tatgatagtc gtacatatcc aatacgaaca    780
gcaagtcagc tgactcgtga aatctacacg aaccctgtcc tggagaactt tgatggtagc    840
ttccgtggat cagcacaagg catagagggt tccatccgga gtcctcatct catggacatc    900
ctgaacagca ttacaatcta cacagatgct catcgaggtg agtattactg gtcaggacac    960
caaatcatgg catccccagt tggattttct ggtccagagt tcactttccc cttgtatgga   1020
acaatgggta atgctgctcc acagcaacga atagttgctc aattgggaca aggggtatat   1080
cgaaccttat catcaacact gtatcgacgt ccattcaaca ttgggataaa caatcaacag   1140
ttgtctgtac tagatgggac agagtttgct tatggaactt cctccaacct cccttcagca   1200
gtttatcgga agtctgggac tgtagactca ctagatgaga tacctccaca gaataacaat   1260
gtacctccaa gacaaggatt ctcccaccgt ctctctcatg tgtctatgtt ccgtagtggc   1320
tttagtaaca gcagtgtgag catcatacgt gcacctatgt tttcatggat tcaccgtagt   1380
gcagagttca ataacaccat tgaccctgaa cgaatcaatc aaatcccact taccaaaagc   1440
accaaccttg gtagcggaac cagcgttgtg aagggtcctg gtttcactgg tggggatatt   1500
ctgcgacgta ccagccctgg acagattagc acactgcgtg tgaacatcac cgctccactg   1560
agtcagcgct atcgagtgag gattcgctat gctagcacta ccaaccttca gttccatacc   1620
agcattgatg gtcgtccaat taaccaaggc aacttcagcg ctaccatgtc cagcggctca   1680
aacctgcaaa gtggatcatt ccgcaccgtt ggctttacca ctccattcaa cttcagcaac   1740
ggcagtagcg tgttcaccct ttccgcacat gtgttcaaca gtggcaacga agtgtacatc   1800
gatagaatcg agtttgtgcc agcggaagtg acttttgaag ctgagtacga ccttgaacgt   1860
gcccaaaagg tcgttaacgc cctcttcact tcttccaacc agatcggatt gaaaacagat   1920
gttacagact accacattga ccaggtgtcc aatcttgtgg attgcttgtc tgatgagttc   1980
tgtctcgatg agaagcgaga actctctgaa aaggttaagc acgctaagag actcagcgat   2040
gaacgaaacc ttcttcagga cccaaatttc aggggaatta atagacaacc agatagaggt   2100
tggcgtggat caacagacat cactatccaa ggtggagacg atgtttttaa ggagaactac   2160
gtgacccttc ctggtactgt tgacgagtgc tatcctacct acctttacca gaagattgac   2220
gaatcaaagc tcaaagcata cactcgttat gagcttcgtg gttacatcga agattcacaa   2280
gatcttgaaa tctacctcat cagatacaac gctaaacacg aaatcgtcaa cgttccaggt   2340
actggatctc tgtggccact ctctgcacag tcacctattg gcaagtgcgg tgagccaaat   2400
agatgtgcac cacacctgga gtggaatccc gatctggact gtagttgtcg tgacggggag   2460
aagtgcgctc atcacagcca tcacttcact cttgatatcg atgttggatg taccgacctt   2520
aatgaagacc tgggcgtttg ggttatcttc aagattaaga cccaggatgg tcatgccaga   2580
cttggtaatc tggagttcct tgaagagaaa cccttgttgg gtgaagctct ggccagagtc   2640
aagcgtgctg agaagaaatg gcgtgataaa cgtgaaaagt tgcaattgga gactaacatt   2700
gtctacaaag aggcaaagga gtctgtggat gccttgttcg tgaactctca gtacgaccga   2760
```

-continued

```
ctccaagtgg ataccaacat tgctatgatt catgctgctg acaaacgtgt tcaccgtatc   2820

agagaagcct atctccctga actgtcagtg atcccaggag tcaacgctgc aatcttcgag   2880

gagcttgaag gtcgaatctt cactgcctat tcactttacg atgcacgaaa cgtgattaag   2940

aatggggatt ttaataacgg gttgttgtgc tggaatgtga aggggcacgt ggatgttgag   3000

gaacaaaaca accaccgttc cgtgcttgtt attcctgagt gggaagcaga ggtgtctcag   3060

gaggttaggg tgtgtcctgg tagaggatat atcttgagag tgactgccta taaggaaggc   3120

tatggtgaag gttgcgtgac aatccacgag atcgaagaca acacagatga gcttaagttc   3180

tctaactgcg ttgaggagga agtctaccca aacaataccg tcacttgtaa caattacaca   3240

ggcacacaag aagagtacga aggaacctac acctcccgaa atcagggtta tgatgaggcc   3300

tatggtaata atccttctgt gcctgccgat tatgcttctg tttacgagga aaagtcttac   3360

actgatggcc gtcgtgagaa cccttgcgaa tccaaccgtg gatacggtga ttacactcca   3420

cttccagcag gatacgttac taaggatctt gagtactttc cagagactga taaagtttgg   3480

atcgaaatcg gagagactga aggcacattc atcgtggatt ctgtggagct cttgctcatg   3540

gaggaa                                                               3546
```

```
<210> SEQ ID NO 24
<211> LENGTH: 591
<212> TYPE: PRT
<213> ORGANISM: Artificial Sequence
<220> FEATURE:
<223> OTHER INFORMATION: Cry1 variant

<400> SEQUENCE: 24

Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Ile Ile Trp Gly Ile Phe Gly Pro Ser Gln Trp Asp Ala Phe
        35                  40                  45

Leu Val Gln Ile Glu Gln Leu Ile Asn Gln Arg Ile Glu Glu Phe Ala
    50                  55                  60

Arg Asn Gln Ala Ile Ser Arg Val Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Lys Glu Glu Met Arg Thr Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Phe Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Phe Thr
                165                 170                 175

Asp His Ala Val Arg Trp His Asn Thr Gly Leu Glu Arg Ile Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220
```

```
Arg Thr Tyr Pro Ile Arg Thr Ala Ser Gln Leu Thr Arg Glu Ile Tyr
225                 230                 235                 240

Thr Asn Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590


<210> SEQ ID NO 25
<211> LENGTH: 3546
<212> TYPE: DNA
<213> ORGANISM: Artificial Sequence
<220> FEATURE:
<223> OTHER INFORMATION: Cry1 variant

<400> SEQUENCE: 25

atgggacaca acaatccaaa tatcaatgaa tgcatcccct ataattgctt gagcaaccct     60
```

```
gaagttgaag ttctgggagg tgagaggata gaaactggat ataccccctat tgatatctct    120
ctgtctttga ctcagttcct cctgagtgag tttgttccag gtgcaggatt tgtgttgggt    180
ttggtagaca ttatctgggg aatctttgga ccatcccaat gggatgcctt tctggtccaa    240
atagagcaac tcataaacca gcgcattgag gaatttgcac gtaaccaggc aatctcccga    300
gttgagggat tgtcaaactt gtaccagata tatgctgaaa gtttcagaga gtgggaagct    360
gacccaacca accctgcatt gaaggaagag atgaggactc agttcaatga tatgaactca    420
gcactgacca ctgccatacc cttgtttgca gtacagaact atcaagtccc attactatca    480
gtctatgtgc aagcagcaaa cctacatttg agtgtcctcc gagatgtatc agtttttggt    540
caacgttggg gatttgatgc tgctaccatc aacagtcgtt acaatgacct cacacgactg    600
attgggaact acacagatca tgcagtccgt tggcacaata ctggattgga gagagtttgg    660
ggacctgata gtcgtgattg gattcgttac aatcagtttc gtcgggaact taccctgact    720
gtcttggata tagtgtcact gtttcctaac tatgatagtc gtacatatcc aatacgaaca    780
gcaagtcagc tgactcgtga aatctacacg aaccctgtcc tggagaactt tgacggtagc    840
ttccgtggat cagcacaagg tatagagggt tccatccgga gccctcatct catggacgtg    900
ctgaacagca ttacaatcta cacagatgct catcgaggtg agtattactg gtcaggacac    960
caaatcatgg catccccagt tggattttct ggtccagagt tcactttccc cttgtatgga   1020
acaatgggta atgctgctcc acagcaacga atagttgctc aattgggaca aggggtatat   1080
cgaaccttat catcaacact gtatcgacgt ccattcaaca ttgggataaa caatcaacag   1140
ttgtctgtac tagatgggac agagtttgct tatggaactt cctccaacct cccttcagca   1200
gtttatcgga agtctgggac tatcgactca ctagatgaga tacctccaca gaataacaat   1260
gtacctccaa gacaaggatt ctcccaccgt ctctctcatg tgtctatgtt ccgtagtggc   1320
tttagtaaca gcagtgtgag catcatacgt gcacctatgt tttcatgggt tcaccgtagt   1380
gcagagttca ataacaccat tgaccctgaa cgaatcaatc aaatcccact taccaaaagc   1440
accaaccttg gtagcggaac cagcgttgtg aagggtcctg gtttcaccgg tggggatatt   1500
ctgcgacgta ccagccctgg acagattagc acactgcgtg tgaacatcac tgctccactg   1560
agtcagcgct atcgagtgag gattcgctat gctagcacta ccaaccttca gttccatacc   1620
agcattgatg gtcgtccaat taaccaaggc aacttcagcg ctaccatgtc cagcggctca   1680
aacctgcaaa gtggatcatt ccgcaccgtt ggctttacca ctccattcaa cttcagcaac   1740
ggcagtagcg tgttcaccct ttccgcacat gtgttcaaca gtggcaacga agtgtacatc   1800
gatagaatcg agtttgtgcc agcggaagtg acttttgaag ctgagtacga ccttgaacgt   1860
gcccaaaagg tcgttaacgc cctcttcact tcttccaacc agatcggatt gaaaacagat   1920
gttacagact accacattga ccaggtgtcc aatcttgtgg attgcttgtc tgatgagttc   1980
tgtctcgatg agaagcgaga actctctgaa aaggttaagc acgctaagag actcagcgat   2040
gaacgaaacc ttcttcagga cccaaatttc aggggaatta atagacaacc agatagaggt   2100
tggcgtggat caacagacat cactatccaa ggtggagacg atgtttttaa ggagaactac   2160
gtgacccttc ctggtactgt tgacgagtgc tatcctacct acctttacca gaagattgac   2220
gaatcaaagc tcaaagcata cactcgttat gagcttcgtg gttacatcga agattcacaa   2280
gatcttgaaa tctacctcat cagatacaac gctaaacacg aaatcgtcaa cgttccaggt   2340
actggatctc tgtggccact ctctgcacag tcacctattg gcaagtgcgg tgagccaaat   2400
agatgtgcac cacacctgga gtggaatccc gatctggact gtagttgtcg tgacggggag   2460
```

```
aagtgcgctc atcacagcca tcacttcact cttgatatcg atgttggatg taccgacctt   2520

aatgaagacc tgggcgtttg ggttatcttc aagattaaga cccaggatgg tcatgccaga   2580

cttggtaatc tggagttcct tgaagagaaa cccttgttgg gtgaagctct ggccagagtc   2640

aagcgtgctg agaagaaatg gcgtgataaa cgtgaaaagt tgcaattgga gactaacatt   2700

gtctacaaag aggcaaagga gtctgtggat gccttgttcg tgaactctca gtacgaccga   2760

ctccaagtgg ataccaacat tgctatgatt catgctgctg acaaacgtgt tcaccgtatc   2820

agagaagcct atctccctga actgtcagtg atcccaggag tcaacgctgc aatcttcgag   2880

gagcttgaag gtcgaatctt cactgcctat tcactttacg atgcacgaaa cgtgattaag   2940

aatggggatt ttaataacgg gttgttgtgc tggaatgtga aggggcacgt ggatgttgag   3000

gaacaaaaca accaccgttc cgtgcttgtt attcctgagt gggaagcaga ggtgtctcag   3060

gaggttaggg tgtgtcctgg tagaggatat atcttgagag tgactgccta taaggaaggc   3120

tatggtgaag gttgcgtgac aatccacgag atcgaagaca acacagatga gcttaagttc   3180

tctaactgcg ttgaggagga agtctaccca aacaataccg tcacttgtaa caattacaca   3240

ggcacacaag aagagtacga aggaacctac acctcccgaa atcagggtta tgatgaggcc   3300

tatggtaata atccttctgt gcctgccgat tatgcttctg tttacgagga aaagtcttac   3360

actgatggcc gtcgtgagaa cccttgcgaa tccaaccgtg gatacggtga ttacactcca   3420

cttccagcag gatacgttac taaggatctt gagtactttc cagagactga taaagtttgg   3480

atcgaaatcg gagagactga aggcacattc atcgtggatt ctgtggagct cttgctcatg   3540

gaggaa                                                              3546
```

<210> SEQ ID NO 26
<211> LENGTH: 591
<212> TYPE: PRT
<213> ORGANISM: Artificial Sequence
<220> FEATURE:
<223> OTHER INFORMATION: Cry1 variant

<400> SEQUENCE: 26

```
Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Ile Ile Trp Gly Ile Phe Gly Pro Ser Gln Trp Asp Ala Phe
        35                  40                  45

Leu Val Gln Ile Glu Gln Leu Ile Asn Gln Arg Ile Glu Glu Phe Ala
    50                  55                  60

Arg Asn Gln Ala Ile Ser Arg Val Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Lys Glu Glu Met Arg Thr Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Tyr Thr
```

-continued

```
                165                 170                 175

Asp His Ala Val Arg Trp His Asn Thr Gly Leu Glu Arg Val Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Ala Ser Gln Leu Thr Arg Glu Ile Tyr
225                 230                 235                 240

Thr Asn Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Val Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Ile Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Val His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590
```

<210> SEQ ID NO 27
<211> LENGTH: 3546
<212> TYPE: DNA
<213> ORGANISM: Artificial Sequence
<220> FEATURE:
<223> OTHER INFORMATION: Cry1 variant

<400> SEQUENCE: 27
atgggacaca acaatccaaa tatcaatgaa tgcatcccct ataattgctt gagcaaccct 60
gaagttgaag ttctgggagg tgagaggata gaaactggat ataccccctat tgatatctct 120 ctgtctttga ctcagttcct cctgagtgag tttgttccag gtgcaggatt tgtgttgggt 180
ttggtagaca ttatctgggg aatctttgga ccatcccaat gggatgcctt tctggtccaa 240
atagagcaac tcataaacca gcgcattgag gaatttgcac gtaaccaggc aatctcccga 300
gttgagggat tgtcaaactt gtaccagata tatgctgaaa gtttcagaga gtgggaagct 360
gacccaacca accctgcatt gaaggaagag atgaggactc agttcaatga tatgaactca 420
gcactgacca ctgccatacc cttgtttgca gtacagaact atcaagtccc attactatca 480
gtctatgtgc aagcagcaaa cctacatttg agtgtcctcc gagatgtatc agtttttggt 540
caacgttggg gatttgatgc tgctaccatc aacagtcgtt acaatgacct cacacgactg 600
attgggaact acacagatca tgcagtccgt tggcacaata ctggattgga gagagtttgg 660
ggacctgata gtcgtgattg gattcgttac aatcagtttc gtcgggaact taccctgact 720
gtcttggata tagtgtcact gtttcctaac tatgatagtc gtacatatcc aatacgaaca 780
gcaagtcagc tgactcgtga aatctacacg aaccctgtcc tggagaactt tgatggtagc 840
ttccgtggat cagcacaagg catagagggt tccatccgga gtcctcatct catggacatc 900
ctgaacagca ttacaatcta cacagatgct catcgaggtg agtattactg gtcaggacac 960
caaatcatgg catccccagt tggattttct ggtccagagt tcactttccc cttgtatgga 1020
acaatgggta atgctgctcc acagcaacga atagttgctc aattgggaca aggggtatat 1080
cgaaccttat catcaacact gtatcgacgt ccattcaaca ttgggataaa caatcaacag 1140
ttgtctgtac tagatgggac agagtttgct tatggaactt cctccaacct cccttcagca 1200
gttttccgga agtctgggac tgtagactca ctagatgaga tacctccaca gaataacaat 1260
gtacctccaa gacaaggatt ctcccaccgt ctctctcatg tgtctatgta ccgtagtggc 1320
ttcagtaaca gcagtgtgag catcatacgt gcacctatgt tttcatgggt tcaccgtagt 1380
gcagagttca ataacaccat tgaccctgaa cgaatcaatc aaatcccact taccaaaagc 1440
accaaccttg gtagcggaac cagcgttgtg aagggtcctg gtttcactgg tggggatatt 1500
ctgcgacgta ccagccctgg acagattagc acactgcgtg tgaacatcac cgctccactg 1560
agtcagcgct atcgagtgag gattcgctat gctagcacta ccaaccttca gttccatacc 1620
agcattgatg gtcgtccaat taaccaaggc aacttcagcg ctaccatgtc cagcggctca 1680
aacctgcaaa gtggatcatt ccgcaccgtt ggctttacca ctccattcaa cttcagcaac 1740
ggcagtagcg tgttcaccct ttccgcacat gtgttcaaca gtggcaacga agtgtacatc 1800
gatagaatcg agtttgtgcc agcggaagtg acttttgaag ctgagtacga ccttgaacgt 1860
gcccaaaagg tcgttaacgc cctcttcact tcttccaacc agatcggatt gaaaacagat 1920
gttacagact accacattga ccaggtgtcc aatcttgtgg attgcttgtc tgatgagttc 1980
tgtctcgatg agaagcgaga actctctgaa aaggttaagc acgctaagag actcagcgat 2040
gaacgaaacc ttcttcagga cccaaatttc aggggaatta atagacaacc agatagaggt 2100

```
tggcgtggat caacagacat cactatccaa ggtggagacg atgtttttaa ggagaactac   2160

gtgacccttc ctggtactgt tgacgagtgc tatcctacct acctttacca gaagattgac   2220

gaatcaaagc tcaaagcata cactcgttat gagcttcgtg gttacatcga agattcacaa   2280

gatcttgaaa tctacctcat cagatacaac gctaaacacg aaatcgtcaa cgttccaggt   2340

actggatctc tgtggccact ctctgcacag tcacctattg gcaagtgcgg tgagccaaat   2400

agatgtgcac cacacctgga gtggaatccc gatctggact gtagttgtcg tgacggggag   2460

aagtgcgctc atcacagcca tcacttcact cttgatatcg atgttggatg taccgacctt   2520

aatgaagacc tgggcgtttg ggttatcttc aagattaaga cccaggatgg tcatgccaga   2580

cttggtaatc tggagttcct tgaagagaaa cccttgttgg gtgaagctct ggccagagtc   2640

aagcgtgctg agaagaaatg gcgtgataaa cgtgaaaagt tgcaattgga gactaacatt   2700

gtctacaaag aggcaaagga gtctgtggat gccttgttcg tgaactctca gtacgaccga   2760

ctccaagtgg ataccaacat tgctatgatt catgctgctg acaaacgtgt tcaccgtatc   2820

agagaagcct atctccctga actgtcagtg atcccaggag tcaacgctgc aatcttcgag   2880

gagcttgaag gtcgaatctt cactgcctat tcactttacg atgcacgaaa cgtgattaag   2940

aatggggatt ttaataacgg gttgttgtgc tggaatgtga aggggcacgt ggatgttgag   3000

gaacaaaaca accaccgttc cgtgcttgtt attcctgagt gggaagcaga ggtgtctcag   3060

gaggttaggg tgtgtcctgg tagaggatat atcttgagag tgactgccta taaggaaggc   3120

tatggtgaag gttgcgtgac aatccacgag atcgaagaca acacagatga gcttaagttc   3180

tctaactgcg ttgaggagga agtctaccca aacaataccg tcacttgtaa caattacaca   3240

ggcacacaag aagagtacga aggaacctac acctcccgaa atcagggtta tgatgaggcc   3300

tatggtaata atccttctgt gcctgccgat tatgcttctg tttacgagga aaagtcttac   3360

actgatggcc gtcgtgagaa cccttgcgaa tccaaccgtg gatacggtga ttacactcca   3420

cttccagcag gatacgttac taaggatctt gagtactttc cagagactga taaagtttgg   3480

atcgaaatcg gagagactga aggcacattc atcgtggatt ctgtggagct cttgctcatg   3540

gaggaa                                                              3546
```

<210> SEQ ID NO 28
<211> LENGTH: 591
<212> TYPE: PRT
<213> ORGANISM: Artificial Sequence
<220> FEATURE:
<223> OTHER INFORMATION: Cry1 variant

<400> SEQUENCE: 28

```
Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Ile Ile Trp Gly Ile Phe Gly Pro Ser Gln Trp Asp Ala Phe
        35                  40                  45

Leu Val Gln Ile Glu Gln Leu Ile Asn Gln Arg Ile Glu Glu Phe Ala
    50                  55                  60

Arg Asn Gln Ala Ile Ser Arg Val Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Lys Glu Glu Met Arg Thr Gln Phe Asn Asp Met Asn Ser Ala
            100                 105                 110
```

-continued

```
Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Tyr Thr
                165                 170                 175

Asp His Ala Val Arg Trp His Asn Thr Gly Leu Glu Arg Val Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Ala Ser Gln Leu Thr Arg Glu Ile Tyr
225                 230                 235                 240

Thr Asn Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Phe Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Tyr Arg Ser Gly Phe Ser Asn Ser Ser
                405                 410                 415

Val Ser Ile Ile Arg Ala Pro Met Phe Ser Trp Val His Arg Ser Ala
            420                 425                 430

Glu Phe Asn Asn Thr Ile Asp Pro Glu Arg Ile Asn Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
```

-continued

```
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590


<210> SEQ ID NO 29
<211> LENGTH: 3567
<212> TYPE: DNA
<213> ORGANISM: Bacillus thuringiensis

<400> SEQUENCE: 29

atggaggaaa ataatcaaaa tcaatgcata ccttacaatt gtttaagtaa tcctgaagaa     60

gtacttttgg atggagaacg gatatcaact ggtaattcat caattgatat ttctctgtca    120

cttgttcagt ttctggtatc taactttgta ccagggggag gatttttagt tggattaata    180

gattttgtat ggggaatagt tggcccttct caatgggatg catttctagt acaaattgaa    240

caattaatta atgaaagaat agctgaattt gctaggaatg ctgctattgc taatttagaa    300

ggattaggaa acaatttcaa tatatatgtg gaagcattta aagaatggga agaagatcct    360

aataatccag aaaccaggac cagagtaatt gatcgctttc gtatacttga tgggctactt    420

gaaagggaca ttccttcgtt tcgaatttct ggatttgaag taccccttt atccgtttat    480

gctcaagcgg ccaatctgca tctagctata ttaagagatt ctgtaatttt tggagaaaga    540

tggggattga caacgataaa tgtcaatgaa aactataata gactaattag gcatattgat    600

gaatatgctg atcactgtgc aaatacgtat aatcggggat taaataattt accgaaatct    660

acgtatcaag attggataac atataatcga ttacggagag acttaacatt gactgtatta    720

gatatcgccg ctttctttcc aaactatgac aataggagat atccaattca gccagttggt    780

caactaacaa gggaagttta tacggaccca ttaattaatt ttaatccaca gttacagtct    840

gtagctcaat tacctacttt taacgttatg gagagcagcc gaattagaaa tcctcattta    900

tttgatatat tgaataatct tacaatcttt acggattggt ttagtgttgg acgcaatttt    960

tattggggag gacatcgagt aatatctagc cttataggag gtggtaacat aacatctcct   1020

atatatggaa gagaggcgaa ccaggagcct ccaagatcct ttacttttaa tggaccggta   1080

tttaggactt tatcaaatcc tactttacga ttattacagc aaccttggcc agcgccacca   1140

tttaatttac gtggtgttga aggagtagaa ttttctacac ctacaaatag ctttacgtat   1200

cgaggaagag gtacggttga ttctttaact gaattaccgc ctgaggataa tagtgtgcca   1260

cctcgcgaag gatatagtca tcgtttatgt catgcaactt ttgttcaaag atctggaaca   1320

cctttttaa caactggtgt agtattttct tggaccgatc gtagtgcaac tcttacaaat   1380

acaattgatc cagagagaat taatcaaata cctttagtga aaggatttag agtttggggg   1440

ggcacctctg tcattacagg accaggattt acaggagggg atatccttcg aagaaatacc   1500

tttggtgatt ttgtatctct acaagtcaat attaattcac caattaccca aagataccgt   1560

ttaagatttc gttacgcttc cagtagggat gcacgagtta tagtattaac aggagcggca   1620

tccacaggag tgggaggcca agttagtgta aatatgcctc ttcagaaaac tatggaaata   1680

ggggagaact taacatctag aacatttaga tataccgatt ttagtaatcc tttttcattt   1740

agagctaatc cagatataat tgggataagt gaacaacctc tatttggtgc aggttctatt   1800

agtagcggtg aactttatat agataaaatt gaaattattc tagcagatgc aacatttgaa   1860
```

```
gcagaatctg atttagaaag agcacaaaag gcggtgaatg ccctgtttac ttcttccaat   1920

caaatcgggt taaaaaccga tgtgacggat tatcatattg atcaagtatc caatttagtg   1980

gattgtttat cagatgaatt ttgtctggat gaaaagcgag aattgtccga gaaagtcaaa   2040

catgcgaagc gactcagtga tgagcggaat ttacttcaag atccaaactt cagagggatc   2100

aatagacaac cagaccgtgg ctggagagga agtacagata ttaccatcca aggaggagat   2160

gacgtattca aagagaatta cgtcacacta ccgggtaccg ttgatgagtg ctatccaacg   2220

tatttatatc agaaaataga tgagtcgaaa ttaaaagctt atacccgtta tgaattaaga   2280

gggtatatcg aagatagtca agacttagaa atctatttga tccgttacaa tgcaaaacac   2340

gaaatagtaa atgtgccagg cacgggttcc ttatggccgc tttcagccca aagtccaatc   2400

ggaaagtgtg gagaaccgaa tcgatgcgcg ccacaccttg aatggaatcc tgatctagat   2460

tgttcctgca gagacgggga aaaatgtgca catcattccc atcatttcac cttggatatt   2520

gatgttggat gtacagactt aaatgaggac ttaggtgtat gggtgatatt caagattaag   2580

acgcaagatg gccatgcaag actagggaat ctagagtttc tcgaagagaa accattatta   2640

ggggaagcac tagctcgtgt gaaaagagcg gagaagaagt ggagagacaa acgagagaaa   2700

ctgcagttgg aaacaaatat tgtttataaa gaggcaaaag aatctgtaga tgctttattt   2760

gtaaactctc aatatgatag attacaagtg gatacgaaca tcgcgatgat tcatgcggca   2820

gataaacgcg ttcatagaat ccgggaagcg tatctgccag agttgtctgt gattccaggt   2880

gtcaatgcgg ccattttcga agaattagag ggacgtattt ttacagcgta ttccttatat   2940

gatgcgagaa atgtcattaa aaatggcgat ttcaataatg gcttattatg ctggaacgtg   3000

aaaggtcatg tagatgtaga agagcaaaac aaccaccgtt cggtccttgt tatcccagaa   3060

tgggaggcag aagtgtcaca agaggttcgt gtctgtccag gtcgtggcta tatccttcgt   3120

gtcacagcat ataaagaggg atatggagag ggctgcgtaa cgatccatga gatcgaagac   3180

aatacagacg aactgaaatt cagcaactgt gtagaagagg aagtatatcc aaacaacaca   3240

gtaacgtgta ataattatac tgggactcaa gaagaatatg agggtacgta cacttctcgt   3300

aatcaaggat atgacgaagc ctatggtaat aacccttccg taccagctga ttacgcttca   3360

gtctatgaag aaaaatcgta tacagatgga cgaagagaga atccttgtga atctaacaga   3420

ggctatgggg attacacacc actaccggct ggttatgtaa caaaggattt agagtacttc   3480

ccagagaccg ataaggtatg gattgagatc ggagaaacag aaggaacatt catcgtggat   3540

agcgtggaat tactccttat ggaggaa                                       3567
```

<210> SEQ ID NO 30
<211> LENGTH: 600
<212> TYPE: PRT
<213> ORGANISM: Bacillus thuringiensis

<400> SEQUENCE: 30

```
Ile Ser Thr Gly Asn Ser Ser Ile Asp Ile Ser Leu Ser Leu Val Gln
1               5                   10                  15

Phe Leu Val Ser Asn Phe Val Pro Gly Gly Gly Phe Leu Val Gly Leu
            20                  25                  30

Ile Asp Phe Val Trp Gly Ile Val Gly Pro Ser Gln Trp Asp Ala Phe
        35                  40                  45

Leu Val Gln Ile Glu Gln Leu Ile Asn Glu Arg Ile Ala Glu Phe Ala
    50                  55                  60

Arg Asn Ala Ala Ile Ala Asn Leu Glu Gly Leu Gly Asn Asn Phe Asn
```

-continued

```
65                  70                  75                  80

Ile Tyr Val Glu Ala Phe Lys Glu Trp Glu Glu Asp Pro Asn Asn Pro
                85                  90                  95

Glu Thr Arg Thr Arg Val Ile Asp Arg Phe Arg Ile Leu Asp Gly Leu
            100                 105                 110

Leu Glu Arg Asp Ile Pro Ser Phe Arg Ile Ser Gly Phe Glu Val Pro
        115                 120                 125

Leu Leu Ser Val Tyr Ala Gln Ala Ala Asn Leu His Leu Ala Ile Leu
    130                 135                 140

Arg Asp Ser Val Ile Phe Gly Glu Arg Trp Gly Leu Thr Thr Ile Asn
145                 150                 155                 160

Val Asn Glu Asn Tyr Asn Arg Leu Ile Arg His Ile Asp Glu Tyr Ala
                165                 170                 175

Asp His Cys Ala Asn Thr Tyr Asn Arg Gly Leu Asn Asn Leu Pro Lys
            180                 185                 190

Ser Thr Tyr Gln Asp Trp Ile Thr Tyr Asn Arg Leu Arg Arg Asp Leu
        195                 200                 205

Thr Leu Thr Val Leu Asp Ile Ala Ala Phe Phe Pro Asn Tyr Asp Asn
    210                 215                 220

Arg Arg Tyr Pro Ile Gln Pro Val Gly Gln Leu Thr Arg Glu Val Tyr
225                 230                 235                 240

Thr Asp Pro Leu Ile Asn Phe Asn Pro Gln Leu Gln Ser Val Ala Gln
                245                 250                 255

Leu Pro Thr Phe Asn Val Met Glu Ser Ser Arg Ile Arg Asn Pro His
            260                 265                 270

Leu Phe Asp Ile Leu Asn Asn Leu Thr Ile Phe Thr Asp Trp Phe Ser
        275                 280                 285

Val Gly Arg Asn Phe Tyr Trp Gly Gly His Arg Val Ile Ser Ser Leu
    290                 295                 300

Ile Gly Gly Gly Asn Ile Thr Ser Pro Ile Tyr Gly Arg Glu Ala Asn
305                 310                 315                 320

Gln Glu Pro Pro Arg Ser Phe Thr Phe Asn Gly Pro Val Phe Arg Thr
                325                 330                 335

Leu Ser Asn Pro Thr Leu Arg Leu Leu Gln Gln Pro Trp Pro Ala Pro
            340                 345                 350

Pro Phe Asn Leu Arg Gly Val Glu Gly Val Glu Phe Ser Thr Pro Thr
        355                 360                 365

Asn Ser Phe Thr Tyr Arg Gly Arg Gly Thr Val Asp Ser Leu Thr Glu
    370                 375                 380

Leu Pro Pro Glu Asp Asn Ser Val Pro Pro Arg Glu Gly Tyr Ser His
385                 390                 395                 400

Arg Leu Cys His Ala Thr Phe Val Gln Arg Ser Gly Thr Pro Phe Leu
                405                 410                 415

Thr Thr Gly Val Val Phe Ser Trp Thr Asp Arg Ser Ala Thr Leu Thr
            420                 425                 430

Asn Thr Ile Asp Pro Glu Arg Ile Asn Gln Ile Pro Leu Val Lys Gly
        435                 440                 445

Phe Arg Val Trp Gly Gly Thr Ser Val Ile Thr Gly Pro Gly Phe Thr
    450                 455                 460

Gly Gly Asp Ile Leu Arg Arg Asn Thr Phe Gly Asp Phe Val Ser Leu
465                 470                 475                 480

Gln Val Asn Ile Asn Ser Pro Ile Thr Gln Arg Tyr Arg Leu Arg Phe
                485                 490                 495
```

```
Arg Tyr Ala Ser Ser Arg Asp Ala Arg Val Ile Val Leu Thr Gly Ala
            500                 505                 510

Ala Ser Thr Gly Val Gly Gly Gln Val Ser Val Asn Met Pro Leu Gln
        515                 520                 525

Lys Thr Met Glu Ile Gly Glu Asn Leu Thr Ser Arg Thr Phe Arg Tyr
    530                 535                 540

Thr Asp Phe Ser Asn Pro Phe Ser Phe Arg Ala Asn Pro Asp Ile Ile
545                 550                 555                 560

Gly Ile Ser Glu Gln Pro Leu Phe Gly Ala Gly Ser Ile Ser Ser Gly
                565                 570                 575

Glu Leu Tyr Ile Asp Lys Ile Glu Ile Ile Leu Ala Asp Ala Thr Phe
            580                 585                 590

Glu Ala Glu Ser Asp Leu Glu Arg
        595                 600


<210> SEQ ID NO 31
<211> LENGTH: 3567
<212> TYPE: DNA
<213> ORGANISM: Artificial Sequence
<220> FEATURE:
<223> OTHER INFORMATION: Cry1 variant

<400> SEQUENCE: 31

atggaggaga acaaccaaaa ccaatgcatc ccatataact gcttgagtaa ccctgaggaa     60

gtgctcctcg acggtgagcg tatctctaca ggtaattctt caatcgacat ctccctttcc    120

ttggtgcaat tcctcgtttc aaatttcgtg ccaggaggtg gattccttgt gggattgatc    180

gacttcgttt ggggaatcgt gggcccaagt caatgggatg ctttcctggt gcaaattgaa    240

caacttatca acgagcgtat cgccgagttt gcacgtaacg ctgctattgc aaatctggag    300

ggtctgggga ataacttcaa tatctacgtt gaggctttta aggaatggga ggaagatcct    360

aacaatccag aaacacgtac ccgtgtgatt gaccgtttta gaattttgga tgggctgctt    420

gaaagggata tcccttcatt ccgaatttct ggttttgagg tgcccctcct ttctgtttat    480

gctcaagcag ctaacctcca tttggctatc cttcgtgata gcgtgatctt tggggagcgt    540

tggggactta ctacaatcaa cgtcaacgag aactataacc gactgatcag acacattgat    600

gagtatgccg atcactgcgc taatacctac aatcgcggac ttaacaatct tccaaagtct    660

acctaccagg actggattac ttacaaccgt ttgcgtaggg atcttacact tacagttctt    720

gacattgcag ctttcttccc aaactatgat aaccgaagat accctatcca gccagtggga    780

caacttacac gagaggttta cacagatcca ttgattaact tcaaccctca acttcaatca    840

gttgctcaat tgccaacctt caacgttatg gaaagctctc gtatcaggaa tccccatctg    900

ttcgacattc ttaacaacct cacaatcttt acagattggt tcagtgtcgg ccgtaatttc    960

tattggggag gacaccgtgt catctctagt cttatcggtg gaggtaatat tacctcccca   1020

atttatggga gagaggccaa ccaggaacct ccacgtagtt tcactttcaa tggtccagtc   1080

tttcgtactt tgagcaaccc aactctgagg cttctccaac aaccttggcc agcacctcca   1140

ttcaatcttc gtggagttga aggtgtggag ttttccactc caaccaacag cttcacttat   1200

cgtggtagag gtactgtcga ctccttgacc gaacttccac ctgaggataa ctctgtgcca   1260

ccacgtgagg gttattcaca tcgtttgtgt cacgcaactt ttgttcagag aagtggcaca   1320

ccatttctga ctactggcgt ggtcttcagt tggacagatc gtagcgcaac tcttactaac   1380

acaatcgacc ctgaacgtat caatcaaatc ccactcgtca aaggttttcg tgtttgggga   1440

ggcacatccg ttatcactgg acctggtttc acaggtggcg atatccttcg aaggaacacc   1500
```

```
ttcggtgatt tcgtgagtct gcaagttaac atcaatagtc ccatcacaca aagatatcgt   1560
ctcagattca gatacgcatc atctcgtgat gcacgtgtca ttgtgcttac tggtgcagca   1620
tctactggag ttggtggtca agttagtgtc aatatgccac tgcaaaagac tatggaaatc   1680
ggcgagaact tgacatccag aacctttagg tacactgact tttccaatcc tttttcattc   1740
cgtgccaatc ctgacattat tggtatctcc gaacaaccac tttttggagc tggatcaatt   1800
tcatctggag aattgtacat tgacaagatt gagatcattc ttgctgatgc aacctttgaa   1860
gctgagtctg acctggaaag agcacaaaag gccgttaacg ccctcttcac ttcttccaac   1920
cagatcggat tgaaaacaga tgttacagac taccacattg accaggtgtc caatcttgtg   1980
gattgcttgt ctgatgaatt ctgtctcgat gagaagcgag aactctctga aaaggttaag   2040
cacgctaaga gactcagcga tgaacgaaac cttcttcagg acccaaattt caggggaatt   2100
aatagacaac cagatagagg ttggcgtgga tcaacagaca tcactatcca aggtggagac   2160
gatgttttta aggagaacta cgtgaccctt cctggtactg ttgacgagtg ctatcctacc   2220
tacctttacc agaagattga cgaatcaaag ctcaaagcat acactcgtta tgagcttcgt   2280
ggttacatcg aagattcaca agatcttgaa atctacctca tcagatacaa cgctaaacac   2340
gaaatcgtca acgttccagg tactggatct ctgtggccac tctctgcaca gtcacctatt   2400
ggcaagtgcg gtgagccaaa tagatgtgca ccacacctgg agtggaatcc cgatctggac   2460
tgtagttgtc gtgacgggga gaagtgcgct catcacagcc atcacttcac tcttgatatc   2520
gatgttggat gtaccgacct taatgaagac ctgggcgttt gggttatctt caagattaag   2580
acccaggatg gtcatgccag acttggtaat ctggagttcc ttgaagagaa acccttgttg   2640
ggtgaagctc tggccagagt caagcgtgct gagaagaaat ggcgtgataa acgtgaaaag   2700
ttgcaattgg agactaacat tgtctacaaa gaggcaaagg agtctgtgga tgccttgttc   2760
gtgaactctc agtacgaccg actccaagtg gataccaaca ttgctatgat tcatgctgct   2820
gacaaacgtg ttcaccgtat cagagaagcc tatctccctg aactgtcagt gatcccagga   2880
gtcaacgctg caatcttcga ggagcttgaa ggtcgaatct tcactgccta ttcactttac   2940
gatgcacgaa acgtgattaa gaatggggat tttaataacg ggttgttgtg ctggaatgtg   3000
aaggggcacg tggatgttga ggaacaaaac aaccaccgtt ccgtgcttgt tattcctgag   3060
tgggaagcag aggtgtctca ggaggttagg gtgtgtcctg gtagaggata tatcttgaga   3120
gtgactgcct ataaggaagg ctatggtgaa ggttgcgtga caatccacga gatcgaagac   3180
aacacagatg agcttaagtt ctctaactgc gttgaggagg aagtctaccc aaacaatacc   3240
gtcacttgta acaattacac aggcacacaa gaagagtacg aaggaaccta cacctcccga   3300
aatcagggtt atgatgaggc ctatggtaat aatccttctg tgcctgccga ttatgcttct   3360
gtttacgagg aaaagtctta cactgatggc cgtcgtgaga acccttgcga atccaaccgt   3420
ggatacggtg attacactcc acttccagca ggatacgtta ctaaggatct tgagtacttt   3480
ccagagactg ataaagtttg gatcgaaatc ggagagactg aaggcacatt catcgtggat   3540
tctgtggagc tcttgctcat ggaggaa                                       3567
```

<210> SEQ ID NO 32
<211> LENGTH: 600
<212> TYPE: PRT
<213> ORGANISM: Artificial Sequence
<220> FEATURE:
<223> OTHER INFORMATION: Cry1 variant

<400> SEQUENCE: 32

-continued

```
Ile Ser Thr Gly Asn Ser Ser Ile Asp Ile Ser Leu Ser Leu Val Gln
1               5                   10                  15

Phe Leu Val Ser Asn Phe Val Pro Gly Gly Gly Phe Leu Val Gly Leu
            20                  25                  30

Ile Asp Phe Val Trp Gly Ile Val Gly Pro Ser Gln Trp Asp Ala Phe
        35                  40                  45

Leu Val Gln Ile Glu Gln Leu Ile Asn Glu Arg Ile Ala Glu Phe Ala
    50                  55                  60

Arg Asn Ala Ala Ile Ala Asn Leu Glu Gly Leu Gly Asn Asn Phe Asn
65                  70                  75                  80

Ile Tyr Val Glu Ala Phe Lys Glu Trp Glu Glu Asp Pro Asn Asn Pro
                85                  90                  95

Glu Thr Arg Thr Arg Val Ile Asp Arg Phe Arg Ile Leu Asp Gly Leu
            100                 105                 110

Leu Glu Arg Asp Ile Pro Ser Phe Arg Ile Ser Gly Phe Glu Val Pro
        115                 120                 125

Leu Leu Ser Val Tyr Ala Gln Ala Ala Asn Leu His Leu Ala Ile Leu
    130                 135                 140

Arg Asp Ser Val Ile Phe Gly Glu Arg Trp Gly Leu Thr Thr Ile Asn
145                 150                 155                 160

Val Asn Glu Asn Tyr Asn Arg Leu Ile Arg His Ile Asp Glu Tyr Ala
                165                 170                 175

Asp His Cys Ala Asn Thr Tyr Asn Arg Gly Leu Asn Asn Leu Pro Lys
            180                 185                 190

Ser Thr Tyr Gln Asp Trp Ile Thr Tyr Asn Arg Leu Arg Arg Asp Leu
        195                 200                 205

Thr Leu Thr Val Leu Asp Ile Ala Ala Phe Phe Pro Asn Tyr Asp Asn
    210                 215                 220

Arg Arg Tyr Pro Ile Gln Pro Val Gly Gln Leu Thr Arg Glu Val Tyr
225                 230                 235                 240

Thr Asp Pro Leu Ile Asn Phe Asn Pro Gln Leu Gln Ser Val Ala Gln
                245                 250                 255

Leu Pro Thr Phe Asn Val Met Glu Ser Ser Arg Ile Arg Asn Pro His
            260                 265                 270

Leu Phe Asp Ile Leu Asn Asn Leu Thr Ile Phe Thr Asp Trp Phe Ser
        275                 280                 285

Val Gly Arg Asn Phe Tyr Trp Gly Gly His Arg Val Ile Ser Ser Leu
    290                 295                 300

Ile Gly Gly Gly Asn Ile Thr Ser Pro Ile Tyr Gly Arg Glu Ala Asn
305                 310                 315                 320

Gln Glu Pro Pro Arg Ser Phe Thr Phe Asn Gly Pro Val Phe Arg Thr
                325                 330                 335

Leu Ser Asn Pro Thr Leu Arg Leu Leu Gln Gln Pro Trp Pro Ala Pro
            340                 345                 350

Pro Phe Asn Leu Arg Gly Val Glu Gly Val Glu Phe Ser Thr Pro Thr
        355                 360                 365

Asn Ser Phe Thr Tyr Arg Gly Arg Gly Thr Val Asp Ser Leu Thr Glu
    370                 375                 380

Leu Pro Pro Glu Asp Asn Ser Val Pro Pro Arg Glu Gly Tyr Ser His
385                 390                 395                 400

Arg Leu Cys His Ala Thr Phe Val Gln Arg Ser Gly Thr Pro Phe Leu
                405                 410                 415

Thr Thr Gly Val Val Phe Ser Trp Thr Asp Arg Ser Ala Thr Leu Thr
```

```
            420                 425                 430

Asn Thr Ile Asp Pro Glu Arg Ile Asn Gln Ile Pro Leu Val Lys Gly
        435                 440                 445

Phe Arg Val Trp Gly Gly Thr Ser Val Ile Thr Gly Pro Gly Phe Thr
    450                 455                 460

Gly Gly Asp Ile Leu Arg Arg Asn Thr Phe Gly Asp Phe Val Ser Leu
465                 470                 475                 480

Gln Val Asn Ile Asn Ser Pro Ile Thr Gln Arg Tyr Arg Leu Arg Phe
                485                 490                 495

Arg Tyr Ala Ser Ser Arg Asp Ala Arg Val Ile Val Leu Thr Gly Ala
            500                 505                 510

Ala Ser Thr Gly Val Gly Gly Gln Val Ser Val Asn Met Pro Leu Gln
        515                 520                 525

Lys Thr Met Glu Ile Gly Glu Asn Leu Thr Ser Arg Thr Phe Arg Tyr
    530                 535                 540

Thr Asp Phe Ser Asn Pro Phe Ser Phe Arg Ala Asn Pro Asp Ile Ile
545                 550                 555                 560

Gly Ile Ser Glu Gln Pro Leu Phe Gly Ala Gly Ser Ile Ser Ser Gly
                565                 570                 575

Glu Leu Tyr Ile Asp Lys Ile Glu Ile Ile Leu Ala Asp Ala Thr Phe
            580                 585                 590

Glu Ala Glu Ser Asp Leu Glu Arg
        595                 600


<210> SEQ ID NO 33
<211> LENGTH: 3465
<212> TYPE: DNA
<213> ORGANISM: Bacillus thuringiensis

<400> SEQUENCE: 33

atggataaca atccgaacat caatgaatgc attccttata attgtttaag taaccctgaa      60

gtagaagtat taggtggaga aagaatagaa actggttaca ccccaatcga tatttccttg     120

tcgctaacgc aatttctttt gagtgaattt gttcccggtg ctggatttgt gttaggacta     180

gttgatataa tatggggaat tttggtccc tctcaatggg acgcatttct tgtacaaatt     240

gaacagttaa ttaaccaaag aatagaagaa ttcgctagga accaagccat ttctagatta     300

gaaggactaa gcaatcttta tcaaatttac gcagaatctt ttagagagtg ggaagcagat     360

cctactaatc cagcattaag agaagagatg cgtattcaat tcaatgacat gaacagtgcc     420

cttacaaccg ctattcctct tttgcagtt caaaattatc aagttcctct tttatcagta     480

tatgttcaag ctgcaaattt acatttatca gttttgagag atgtttcagt gtttggacaa     540

aggtggggat ttgatgccgc gactatcaat agtcgttata atgatttaac taggcttatt     600

ggcaactata cagatcatgc tgtacgctgg tacaatacgg gattagagcg tgtatgggga     660

ccggattcta gagattggat aagatataat caatttagaa gagaattaac actaactgta     720

ttagatatcg tttctctatt tccgaactat gatagtagaa cgtatccaat tcgaacagtt     780

tcccaattaa caagagaaat ttatacaaac ccagtattag aaaattttga tggtagtttt     840

cgaggctcgg ctcagggcat agaaggaagt attaggagtc cacatttgat ggatatactt     900

aacagtataa ccatctatac ggatgctcat agaggagaat attattggtc agggcatcaa     960

ataatggctt ctcctgtagg gttttcgggg ccagaattca cttttccgct atatggaact    1020

atgggaaatg cagctccaca acaacgtatt gttgctcaac taggtcaggg cgtgtataga    1080

acattatcgt ccactttata tagaagacct tttaatatag ggataaataa tcaacaacta    1140
```

-continued

```
tctgttcttg acgggacaga atttgcttat ggaacctcct caaatttgcc atccgctgta   1200
tacagaaaaa gcggaacggt agattcgctg gatgaaatac cgccacagaa taacaacgtg   1260
ccacctaggc aaggatttag tcatcgatta agccatgttt caatgtttcg ttcaggcttt   1320
agtaatagta gtgtaagtat aataagagct cctatgttct cttggataca tcgtagtgct   1380
gaatttaata atataattcc ttcatcacaa attacacaaa tacctttaac aaaatctact   1440
aatcttggct ctggaacttc tgtcgttaaa ggaccaggat ttacaggagg agatattctt   1500
cgaagaactt cacctggcca gatttcaacc ttaagagtaa atattactgc accattatca   1560
caaagatatc gggtaagaat tcgctacgct tctaccacaa atttacaatt ccatacatca   1620
attgacggaa gacctattaa tcaggggaat ttttcagcaa ctatgagtag tgggagtaat   1680
ttacagtccg gaagctttag gactgtaggt tttactactc cgtttaactt ttcaaatgga   1740
tcaagtgtat ttacgttaag tgctcatgtc ttcaattcag gcaatgaagt ttatatagat   1800
cgaattgaat ttgttccggc agaagtaacc tttgaggcag aatatgattt agaaaagagca   1860
caaaaggcgg tgaatgagct gtttacttct tccaatcaaa tcgggttaaa aacagatgtg   1920
acggattatc atattgatca agtatccaat ttagttgagt gtttatctga tgaattttgt   1980
ctggatgaaa aaaaagaatt gtccgagaaa gtcaaacatg cgaagcgact tagtgatgag   2040
cggaatttac ttcaagatcc aaactttaga gggatcaata gacaactaga ccgtggctgg   2100
agaggaagta cggatattac catccaagga ggcgatgacg tattcaaaga gaattacgtt   2160
acgctattgg gtacctttga tgagtgctat ccaacgtatt tatatcaaaa aatagatgag   2220
tcgaaattaa aagcctatac ccgttaccaa ttaagagggt atatcgaaga tagtcaagac   2280
ttagaaatct atttaattcg ctacaatgcc aaacacgaaa cagtaaatgt gccaggtacg   2340
ggttccttat ggccgctttc agccccaagt ccaatcggaa aatgtgccca tcattcccat   2400
catttctcct tggacattga tgttggatgt acagacttaa atgaggactt aggtgtatgg   2460
gtgatattca agattaagac gcaagatggc catgcaagac taggaaatct agaatttctc   2520
gaagagaaac cattagtagg agaagcacta gctcgtgtga aaagagcgga gaaaaaatgg   2580
agagacaaac gtgaaaaatt ggaatgggaa acaaatattg tttataaaga ggcaaaagaa   2640
tctgtagatg ctttatttgt aaactctcaa tatgatagat tacaagcgga taccaacatc   2700
gcgatgattc atgcggcaga taaacgcgtt catagcattc gagaagctta tctgcctgag   2760
ctgtctgtga ttccgggtgt caatgcggct atttttgaag aattagaagg gcgtattttc   2820
actgcattct ccctatatga tgcgagaaat gtcattaaaa atggtgattt taataatggc   2880
ttatcctgct ggaacgtgaa agggcatgta gatgtagaag aacaaaacaa ccaccgttcg   2940
gtccttgttg ttccggaatg ggaagcagaa gtgtcacaag aagttcgtgt ctgtccgggt   3000
cgtggctata tccttcgtgt cacagcgtac aaggagggat atggagaagg ttgcgtaacc   3060
attcatgaga tcgagaacaa tacagacgaa ctgaagttta gcaactgtgt agaagaggaa   3120
gtatatccaa acaacacggt aacgtgtaat gattatactg cgactcaaga agaatatgag   3180
ggtacgtaca cttctcgtaa tcgaggatat gacggagcct atgaaagcaa ttcttctgta   3240
ccagctgatt atgcatcagc ctatgaagaa aaagcatata cagatggacg aagagacaat   3300
ccttgtgaat ctaacagagg atatggggat tacacaccac taccagctgg ctatgtgaca   3360
aaagaattag agtacttccc agaaaccgat aaggtatgga ttgagatcgg agaaacggaa   3420
ggaacattca tcgtggacag cgtggaatta cttcttatgg aggaa                   3465
```

<210> SEQ ID NO 34
<211> LENGTH: 591
<212> TYPE: PRT
<213> ORGANISM: Bacillus thuringiensis

<400> SEQUENCE: 34

```
Ile Glu Thr Gly Tyr Thr Pro Ile Asp Ile Ser Leu Ser Leu Thr Gln
1               5                   10                  15

Phe Leu Leu Ser Glu Phe Val Pro Gly Ala Gly Phe Val Leu Gly Leu
            20                  25                  30

Val Asp Ile Ile Trp Gly Ile Phe Gly Pro Ser Gln Trp Asp Ala Phe
        35                  40                  45

Leu Val Gln Ile Glu Gln Leu Ile Asn Gln Arg Ile Glu Glu Phe Ala
    50                  55                  60

Arg Asn Gln Ala Ile Ser Arg Leu Glu Gly Leu Ser Asn Leu Tyr Gln
65                  70                  75                  80

Ile Tyr Ala Glu Ser Phe Arg Glu Trp Glu Ala Asp Pro Thr Asn Pro
                85                  90                  95

Ala Leu Arg Glu Glu Met Arg Ile Gln Phe Asn Asp Met Asn Ser Ala
            100                 105                 110

Leu Thr Thr Ala Ile Pro Leu Phe Ala Val Gln Asn Tyr Gln Val Pro
        115                 120                 125

Leu Leu Ser Val Tyr Val Gln Ala Ala Asn Leu His Leu Ser Val Leu
    130                 135                 140

Arg Asp Val Ser Val Phe Gly Gln Arg Trp Gly Phe Asp Ala Ala Thr
145                 150                 155                 160

Ile Asn Ser Arg Tyr Asn Asp Leu Thr Arg Leu Ile Gly Asn Tyr Thr
                165                 170                 175

Asp His Ala Val Arg Trp Tyr Asn Thr Gly Leu Glu Arg Val Trp Gly
            180                 185                 190

Pro Asp Ser Arg Asp Trp Ile Arg Tyr Asn Gln Phe Arg Arg Glu Leu
        195                 200                 205

Thr Leu Thr Val Leu Asp Ile Val Ser Leu Phe Pro Asn Tyr Asp Ser
    210                 215                 220

Arg Thr Tyr Pro Ile Arg Thr Val Ser Gln Leu Thr Arg Glu Ile Tyr
225                 230                 235                 240

Thr Asn Pro Val Leu Glu Asn Phe Asp Gly Ser Phe Arg Gly Ser Ala
                245                 250                 255

Gln Gly Ile Glu Gly Ser Ile Arg Ser Pro His Leu Met Asp Ile Leu
            260                 265                 270

Asn Ser Ile Thr Ile Tyr Thr Asp Ala His Arg Gly Glu Tyr Tyr Trp
        275                 280                 285

Ser Gly His Gln Ile Met Ala Ser Pro Val Gly Phe Ser Gly Pro Glu
    290                 295                 300

Phe Thr Phe Pro Leu Tyr Gly Thr Met Gly Asn Ala Ala Pro Gln Gln
305                 310                 315                 320

Arg Ile Val Ala Gln Leu Gly Gln Gly Val Tyr Arg Thr Leu Ser Ser
                325                 330                 335

Thr Leu Tyr Arg Arg Pro Phe Asn Ile Gly Ile Asn Asn Gln Gln Leu
            340                 345                 350

Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
```

```
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Ile Ile Pro Ser Ser Gln Ile Thr Gln Ile Pro Leu
        435                 440                 445

Thr Lys Ser Thr Asn Leu Gly Ser Gly Thr Ser Val Val Lys Gly Pro
    450                 455                 460

Gly Phe Thr Gly Gly Asp Ile Leu Arg Arg Thr Ser Pro Gly Gln Ile
465                 470                 475                 480

Ser Thr Leu Arg Val Asn Ile Thr Ala Pro Leu Ser Gln Arg Tyr Arg
                485                 490                 495

Val Arg Ile Arg Tyr Ala Ser Thr Thr Asn Leu Gln Phe His Thr Ser
            500                 505                 510

Ile Asp Gly Arg Pro Ile Asn Gln Gly Asn Phe Ser Ala Thr Met Ser
        515                 520                 525

Ser Gly Ser Asn Leu Gln Ser Gly Ser Phe Arg Thr Val Gly Phe Thr
    530                 535                 540

Thr Pro Phe Asn Phe Ser Asn Gly Ser Ser Val Phe Thr Leu Ser Ala
545                 550                 555                 560

His Val Phe Asn Ser Gly Asn Glu Val Tyr Ile Asp Arg Ile Glu Phe
                565                 570                 575

Val Pro Ala Glu Val Thr Phe Glu Ala Glu Tyr Asp Leu Glu Arg
            580                 585                 590


<210> SEQ ID NO 35
<211> LENGTH: 633
<212> TYPE: PRT
<213> ORGANISM: Bacillus thuringiensis

<400> SEQUENCE: 35

Met Gly Asn Ser Val Leu Asn Ser Gly Arg Thr Thr Ile Cys Asp Ala
1               5                   10                  15

Tyr Asn Val Ala Ala His Asp Pro Phe Ser Phe Gln His Lys Ser Leu
            20                  25                  30

Asp Thr Val Gln Lys Glu Trp Thr Glu Trp Lys Lys Asn Asn His Ser
        35                  40                  45

Leu Tyr Leu Asp Pro Ile Val Gly Thr Val Ala Ser Phe Leu Leu Lys
    50                  55                  60

Lys Val Gly Ser Leu Val Gly Lys Arg Ile Leu Ser Glu Leu Arg Asn
65                  70                  75                  80

Leu Ile Phe Pro Ser Gly Ser Thr Asn Leu Met Gln Asp Ile Leu Arg
                85                  90                  95

Glu Thr Glu Lys Phe Leu Asn Gln Arg Leu Asn Thr Asp Thr Leu Ala
            100                 105                 110

Arg Val Asn Ala Glu Leu Thr Gly Leu Gln Ala Asn Val Glu Glu Phe
        115                 120                 125

Asn Arg Gln Val Asp Asn Phe Leu Asn Pro Asn Arg Asn Ala Val Pro
    130                 135                 140

Leu Ser Ile Thr Ser Ser Val Asn Thr Met Gln Gln Leu Phe Leu Asn
145                 150                 155                 160

Arg Leu Pro Gln Phe Gln Met Gln Gly Tyr Gln Leu Leu Leu Leu Pro
                165                 170                 175

Leu Phe Ala Gln Ala Ala Asn Leu His Leu Ser Phe Ile Arg Asp Val
```

-continued

```
            180                 185                 190

Ile Leu Asn Ala Asp Glu Trp Gly Ile Ser Ala Ala Thr Leu Arg Thr
        195                 200                 205

Tyr Arg Asp Tyr Leu Lys Asn Tyr Thr Arg Asp Tyr Ser Asn Tyr Cys
    210                 215                 220

Ile Asn Thr Tyr Gln Ser Ala Phe Lys Gly Leu Asn Thr Arg Leu His
225                 230                 235                 240

Asp Met Leu Glu Phe Arg Thr Tyr Met Phe Leu Asn Val Phe Glu Tyr
                245                 250                 255

Val Ser Ile Trp Ser Leu Phe Lys Tyr Gln Ser Leu Leu Val Ser Ser
            260                 265                 270

Gly Ala Asn Leu Tyr Ala Ser Gly Ser Gly Pro Gln Gln Thr Gln Ser
        275                 280                 285

Phe Thr Ser Gln Asp Trp Pro Phe Leu Tyr Ser Leu Phe Gln Val Asn
    290                 295                 300

Ser Asn Tyr Val Leu Asn Gly Phe Ser Gly Ala Arg Leu Ser Asn Thr
305                 310                 315                 320

Phe Pro Asn Ile Val Gly Leu Pro Gly Ser Thr Thr Thr His Ala Leu
                325                 330                 335

Leu Ala Ala Arg Val Asn Tyr Ser Gly Gly Ile Ser Ser Gly Asp Ile
            340                 345                 350

Gly Ala Ser Pro Phe Asn Gln Asn Phe Asn Cys Ser Thr Phe Leu Pro
        355                 360                 365

Pro Leu Leu Thr Pro Phe Val Arg Ser Trp Leu Asp Ser Gly Ser Asp
    370                 375                 380

Arg Glu Gly Val Ala Thr Val Thr Asn Trp Gln Thr Glu Ser Phe Glu
385                 390                 395                 400

Thr Thr Leu Gly Leu Arg Ser Gly Ala Phe Thr Ala Arg Gly Asn Ser
                405                 410                 415

Asn Tyr Phe Pro Asp Tyr Phe Ile Arg Asn Ile Ser Gly Val Pro Leu
            420                 425                 430

Val Val Arg Asn Glu Asp Leu Arg Arg Pro Leu His Tyr Asn Glu Ile
        435                 440                 445

Arg Asn Ile Ala Ser Pro Ser Gly Thr Pro Gly Gly Ala Arg Ala Tyr
    450                 455                 460

Met Val Ser Val His Asn Arg Lys Asn Asn Ile His Ala Val His Glu
465                 470                 475                 480

Asn Gly Ser Met Ile His Leu Ala Pro Asn Asp Tyr Thr Gly Phe Thr
                485                 490                 495

Ile Ser Pro Ile His Ala Thr Gln Val Asn Asn Gln Thr Arg Thr Phe
            500                 505                 510

Ile Ser Glu Lys Phe Gly Asn Gln Gly Asp Ser Leu Arg Phe Glu Gln
        515                 520                 525

Asn Asn Thr Thr Ala Arg Tyr Thr Leu Arg Gly Asn Gly Asn Ser Tyr
    530                 535                 540

Asn Leu Tyr Leu Arg Val Ser Ser Ile Gly Asn Ser Thr Ile Arg Val
545                 550                 555                 560

Thr Ile Asn Gly Arg Val Tyr Thr Ala Thr Asn Val Asn Thr Thr Thr
                565                 570                 575

Asn Asn Asp Gly Val Asn Asp Asn Gly Ala Arg Phe Ser Asp Ile Asn
            580                 585                 590

Ile Gly Asn Val Val Ala Ser Ser Asn Ser Asp Val Pro Leu Asp Ile
        595                 600                 605
```

Asn Val Thr Leu Asn Ser Gly Thr Gln Phe Asp Leu Met Asn Ile Met
610 615 620

Leu Val Pro Thr Asn Ile Ser Pro Leu
625 630

<210> SEQ ID NO 36
<211> LENGTH: 592
<212> TYPE: PRT
<213> ORGANISM: Bacillus thuringiensis

<400> SEQUENCE: 36

Ile Glu Thr Gly Tyr Thr Pro Ile Asp Ile Ser Leu Ser Leu Thr Gln
1 5 10 15

Phe Leu Leu Ser Glu Phe Val Pro Gly Ala Gly Phe Val Leu Gly Leu
20 25 30

Val Asp Ile Ile Trp Gly Ile Phe Gly Pro Ser Gln Trp Asp Ala Phe
35 40 45

Leu Val Gln Ile Glu Gln Leu Ile Asn Gln Arg Ile Glu Glu Phe Ala
50 55 60

Arg Asn Gln Ala Ile Ser Arg Leu Glu Gly Leu Ser Asn Leu Tyr Gln
65 70 75 80

Ile Tyr Ala Glu Ser Phe Arg Glu Trp Glu Ala Asp Pro Thr Asn Pro
85 90 95

Ala Leu Arg Glu Glu Met Arg Ile Gln Phe Asn Asp Met Asn Ser Ala
100 105 110

Leu Thr Thr Ala Ile Pro Leu Phe Ala Val Gln Asn Tyr Gln Val Pro
115 120 125

Leu Leu Ser Val Tyr Val Gln Ala Ala Asn Leu His Leu Ser Val Leu
130 135 140

Arg Asp Val Ser Val Phe Gly Gln Arg Trp Gly Phe Asp Ala Ala Thr
145 150 155 160

Ile Asn Ser Arg Tyr Asn Asp Leu Thr Arg Leu Ile Gly Asn Tyr Thr
165 170 175

Asp Tyr Ala Val Arg Trp Tyr Asn Thr Gly Leu Glu Arg Val Trp Gly
180 185 190

Pro Asp Ser Arg Asp Trp Val Arg Tyr Asn Gln Phe Arg Arg Glu Leu
195 200 205

Thr Leu Thr Val Leu Asp Ile Val Ala Leu Phe Pro Asn Tyr Asp Ser
210 215 220

Arg Arg Tyr Pro Ile Arg Thr Val Ser Gln Leu Thr Arg Glu Ile Tyr
225 230 235 240

Thr Asn Pro Val Leu Glu Asn Phe Asp Gly Ser Phe Arg Gly Ser Ala
245 250 255

Gln Gly Ile Glu Arg Ser Ile Arg Ser Pro His Leu Met Asp Ile Leu
260 265 270

Asn Ser Ile Thr Ile Tyr Thr Asp Ala His Arg Gly Tyr Tyr Tyr Trp
275 280 285

Ser Gly His Gln Ile Met Ala Ser Pro Val Gly Phe Ser Gly Pro Glu
290 295 300

Phe Thr Phe Pro Leu Tyr Gly Thr Met Gly Asn Ala Ala Pro Gln Gln
305 310 315 320

Arg Ile Val Ala Gln Leu Gly Gln Gly Val Tyr Arg Thr Leu Ser Ser
325 330 335

Thr Leu Tyr Arg Arg Pro Phe Asn Ile Gly Ile Asn Asn Gln Gln Leu
340 345 350

-continued

```
Ser Val Leu Asp Gly Thr Glu Phe Ala Tyr Gly Thr Ser Ser Asn Leu
        355                 360                 365

Pro Ser Ala Val Tyr Arg Lys Ser Gly Thr Val Asp Ser Leu Asp Glu
    370                 375                 380

Ile Pro Pro Gln Asn Asn Asn Val Pro Pro Arg Gln Gly Phe Ser His
385                 390                 395                 400

Arg Leu Ser His Val Ser Met Phe Arg Ser Gly Phe Ser Asn Ser Ser
                405                 410                 415

Val Ser Ile Ile Arg Ala Pro Met Phe Ser Trp Ile His Arg Ser Ala
            420                 425                 430

Glu Phe Asn Asn Ile Ile Ala Ser Asp Ser Ile Thr Gln Ile Pro Ala
        435                 440                 445

Val Lys Gly Asn Phe Leu Phe Asn Gly Ser Val Ile Ser Gly Pro Gly
    450                 455                 460

Phe Thr Gly Gly Asp Leu Val Arg Leu Asn Ser Ser Gly Asn Asn Ile
465                 470                 475                 480

Gln Asn Arg Gly Tyr Ile Glu Val Pro Ile His Phe Pro Ser Thr Ser
                485                 490                 495

Thr Arg Tyr Arg Val Arg Val Arg Tyr Ala Ser Val Thr Pro Ile His
            500                 505                 510

Leu Asn Val Asn Trp Gly Asn Ser Ser Ile Phe Ser Asn Thr Val Pro
        515                 520                 525

Ala Thr Ala Thr Ser Leu Asp Asn Leu Gln Ser Ser Asp Phe Gly Tyr
    530                 535                 540

Phe Glu Ser Ala Asn Ala Phe Thr Ser Ser Leu Gly Asn Ile Val Gly
545                 550                 555                 560

Val Arg Asn Phe Ser Gly Thr Ala Gly Val Ile Ile Asp Arg Phe Glu
                565                 570                 575

Phe Ile Pro Val Thr Ala Thr Leu Glu Ala Glu Tyr Asn Leu Glu Arg
            580                 585                 590
```

*BACILLUS THURINGIENSIS* CRYSTAL POLYPEPTIDES, POLYNUCLEOTIDES, AND COMPOSITIONS THEREOF

CROSS-REFERENCE TO RELATED APPLICATIONS

This is a Divisional Application of U.S. patent application Ser. No. 11/953,648 filed Dec. 10, 2007, which has published as Publication No. US2008/0172762 and is incorporated herein in its entirety. U.S. patent application Ser. No. 11/953,648 is a non-provisional of U.S. Patent Application Ser. No. 60/873,849 filed Dec. 8, 2006, the contents of which are hereby incorporated by reference in its entirety.

FIELD OF THE INVENTION

The present invention relates generally to the field of pest control and provides insecticidal polypeptides related to *Bacillus thuringiensis* Cry1 polypeptides and the polynucleotides that encode them. The present invention also relates to methods and compositions for altering resistance of plants to insect predation including, but not limited to, transgenic plant production.

BACKGROUND OF THE INVENTION

Numerous commercially valuable plants, including common agricultural crops, are susceptible to attack by insect and nematode pests. These pests can cause substantial reductions in crop yield and quality. Traditionally, farmers have relied heavily on chemical pesticides to combat pest damage. However, the use of chemical pesticides raises its own set of problems, including the cost and inconvenience of applying the pesticides. Furthermore, chemical residues raise environmental and health concerns. For these and other reasons there is a demand for alternative insecticidal agents.

An environmentally friendly approach to controlling pests is the use of pesticidal crystal proteins derived from the soil bacterium *Bacillus thuringiensis* ("Bt"), commonly referred to as "Cry proteins." The Cry proteins are globular protein molecules which accumulate as protoxins in crystalline form during late stage of the sporulation of *Bacillus thuringiensis*. After ingestion by the pest, the crystals are solubilized to release protoxins in the alkaline midgut environment of the larvae. Protoxins (~130 kDa) are converted into mature toxic fragments (~66 kDa N terminal region) by gut proteases. Many of these proteins are quite toxic to specific target insects, but harmless to plants and other non-targeted organisms. Some Cry proteins have been recombinantly expressed in crop plants to provide pest-resistant transgenic plants. Among those, Bt-transgenic cotton and corn have been widely cultivated.

A large number of Cry proteins have been isolated, characterized and classified based on amino acid sequence homology (Crickmore et al., 1998, *Microbiol. Mol. Biol. Rev.*, 62: 807-813). This classification scheme provides a systematic mechanism for naming and categorizing newly discovered Cry proteins. The Cry1 classification is the best known and contains the highest number of cry genes which currently totals over 130.

It has generally been found that individual Cry proteins possess relatively narrow activity spectra. For example, Cry1Ac was the first toxin to be deployed in transgenic cotton for control of *H. virescens* and *H. zea* insect pests. This toxin is known for its high level toxicity to *H. virescens*. However, it is slightly deficient in its ability to control *H. zea* and has almost no activity on *Spodoptera* species. Additionally, Cry1Ab toxin has slightly less activity on *H. zea* than Cry1Ac but has far superior activity against *S. exigua*.

Second generation transgenic crops could be more resistant to insects if they are able to express multiple and/or novel Bt genes. Accordingly, new insecticidal proteins having broad activity spectra would be highly desirable.

SUMMARY OF THE INVENTION

The present invention relates to Cry polypeptides derived from *Bacillus thuringiensis* Cry1 polypeptides (e.g., Cry1Aa, Cry1Ab, Cry1Ac, Cry1Ad, Cry1Ae, Cry1Ag, and Cry1Ca) including, but not limited to, the Cry1-derived polypeptides of SEQ ID NOS:2, 4, 6, 8, 10, 12, 14, 16, 18, 20, 22, 24, 26, and 28. In addition to the polypeptide sequence of Cry1-derived polypeptides, it will be appreciated that polypeptides of the invention also encompass variants thereof, including, but not limited to, any fragment including the gut activated mature toxin fragment, analog, homolog, naturally occurring allele, or mutant thereof. Polypeptides of the invention also encompass those polypeptides that are encoded by any Cry1-derived nucleic acid of the invention. In one embodiment, shuffled polypeptides that have at least one Cry1 functional activity (e.g., insecticidal activity) and are at least 90%, 91%, 92%, 93%, 94%, 95%, 96% 97%, 98%, 99% or 99.5% identical to the mature toxin portion of polypeptide sequence of any of SEQ ID NOS: 2, 4, 6, 8, 10, 12, 14, 16, 18, 20, 22, 24, 26, 28, or variants thereof. In another embodiment, polypeptides that have at least one Cry1 functional activity (e.g., insecticidal activity) and are at least 99% or 99.5% identical to the mature toxin portion of polypeptide sequence of any of SEQ ID NOS: 2, 4, 6, 8, 10, 12, 14, 16, 18, 20, 22, 24, 26, 28, or variants thereof. Methods of production of the polypeptides of the invention, e.g., by recombinant means, are also provided. Compositions comprising one or more polypeptides of the invention are also encompassed.

The present invention also relates to Cry1-derived nucleic acid molecules of SEQ ID NOS: 1, 3, 5, 7, 9, 11, 13, 15, 17, 19, 21, 23, 25, and 27. Also encompassed by the present invention are fragments and analogs which encode polypeptides that are at least partially functionally active, i.e., they are capable of displaying one or more known functional activities associated with a wild type Cry1 polypeptide. In one embodiment, it encompasses an isolated shuffled nucleic acid molecule that is at least 90%, 91%, 92%, 93%, 94%, 95%, 96% 97%, 98%, 99% or 99.5% identical to any of SEQ ID NOS: 1, 3, 5, 7, 9, 11, 13, 15, 17, 19, 21, 23, 25, 27, or a compliment thereof. In another embodiment, it encompasses an isolated nucleic acid molecule that is are at least 99% or 99.5% identical to the mature toxin portion of polypeptide sequence of any of SEQ ID NOS: 1, 3, 5, 7, 9, 11, 13, 15, 17, 19, 21, 23, 25, 27, or a compliment thereof. Vectors comprising nucleic acids of the invention are also encompassed. Cells or plants comprising the vectors of the invention are also encompassed.

The present invention also relates to transgenic plants expressing a nucleic acid and/or polypeptide of the invention. The transgenic plants can express the transgene in any way known in the art including, but not limited to, constitutive expression, developmentally regulated expression, tissue specific expression, etc. Seed obtained from a transgenic plant of the invention is also encompassed.

Each of the purified protoxins was introduced into the diet of an insect and the $EC_{50}$ of each was determined. The $EC_{50}$ values were then converted to relative inverse values. The $EC_{50}$ of wild type Cry1Ca against *H. zea* was given a value of 1.0. The $EC_{50}$ of the remaining protoxins were assigned a relative value.

Figure 2:
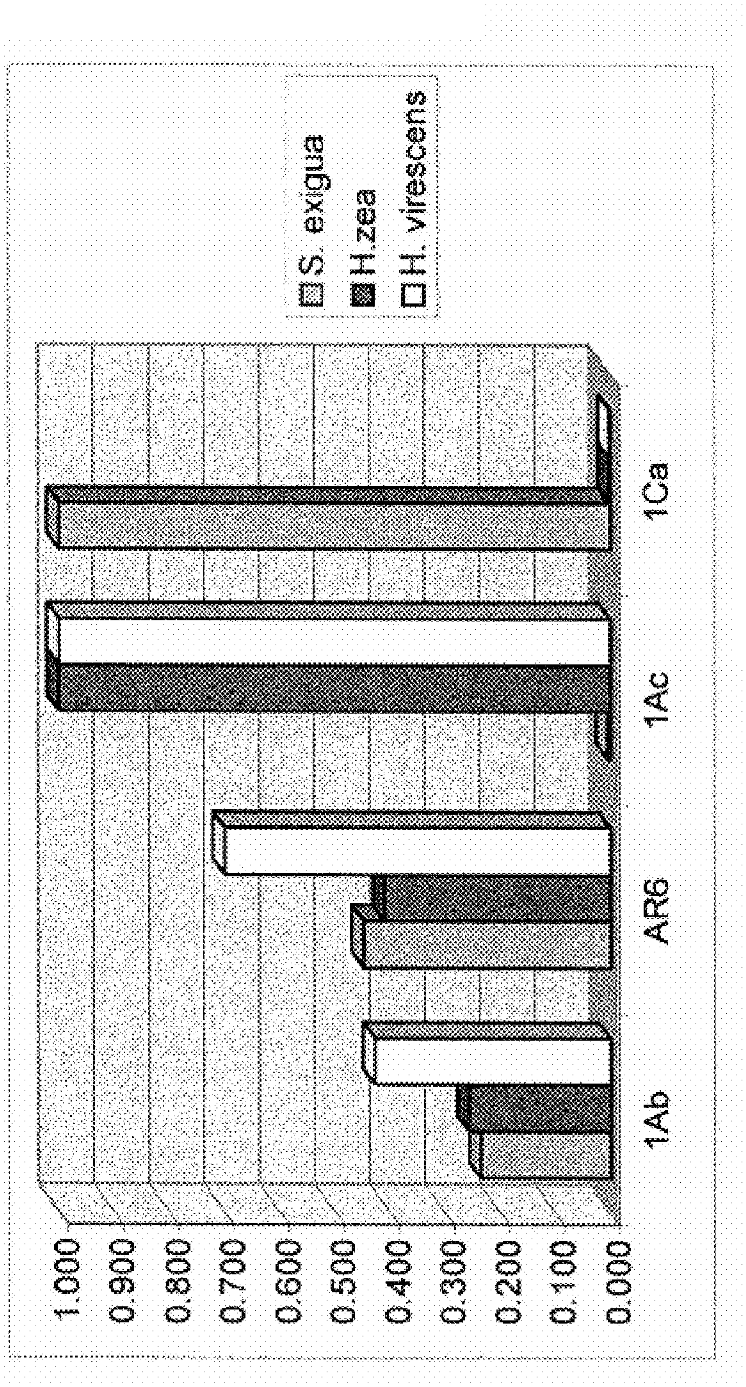

FIG. 2 shows a comparison of relative activity of protoxin encoded by shuffled variant AR6 with that of wild type Cry1Ab, Cry1Ac, and Cry1Ca on *Heliothis virescens, Helicoverpa zea*, and *Spodoptera exigua*. Each of the purified protoxins was introduced into the diet of an insect and the $EC_{50}$ of each was determined. The $EC_{50}$ values were then converted to relative inverse values. The protoxin showing the lowest $EC_{50}$ (highest specific activity) for each insect type was given a value of 1.0. The $EC_{50}$ of the remaining protoxins were assigned a lower relative value.

Figure 3:
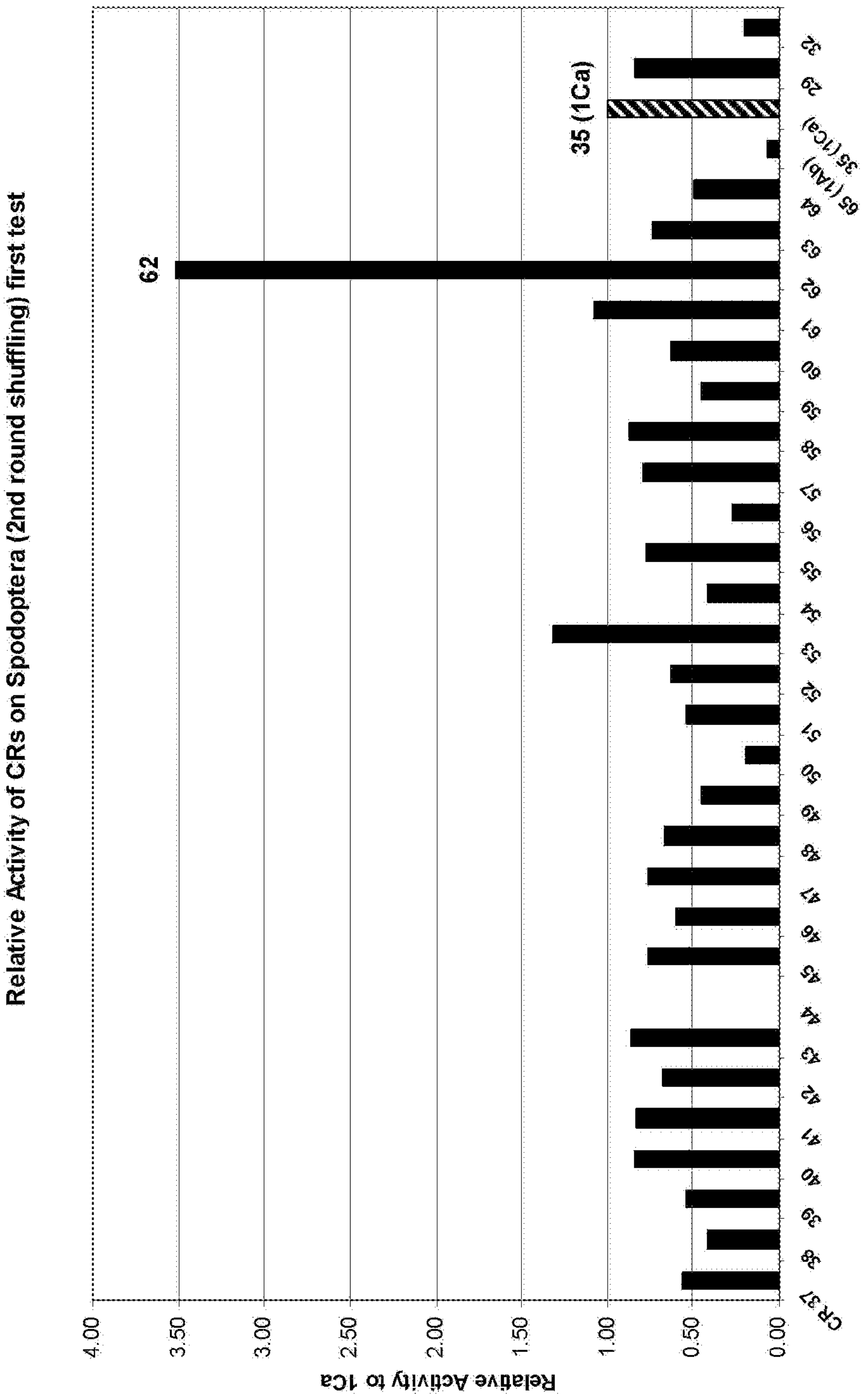

FIG. 3 shows the relative efficacy of Cry1Ca shuffled variants against *Spodoptera exigua*. Each of the purified protoxins was introduced into the diet of an insect and the $EC_{50}$ of each was determined. The $EC_{50}$ values were then converted to relative inverse values. The $EC_{50}$ of wild type Cry1Ca against *Spodoptera exigua* was given a value of 1.0. The $EC_{50}$ of the remaining protoxins were assigned a relative value.

Figure 4:
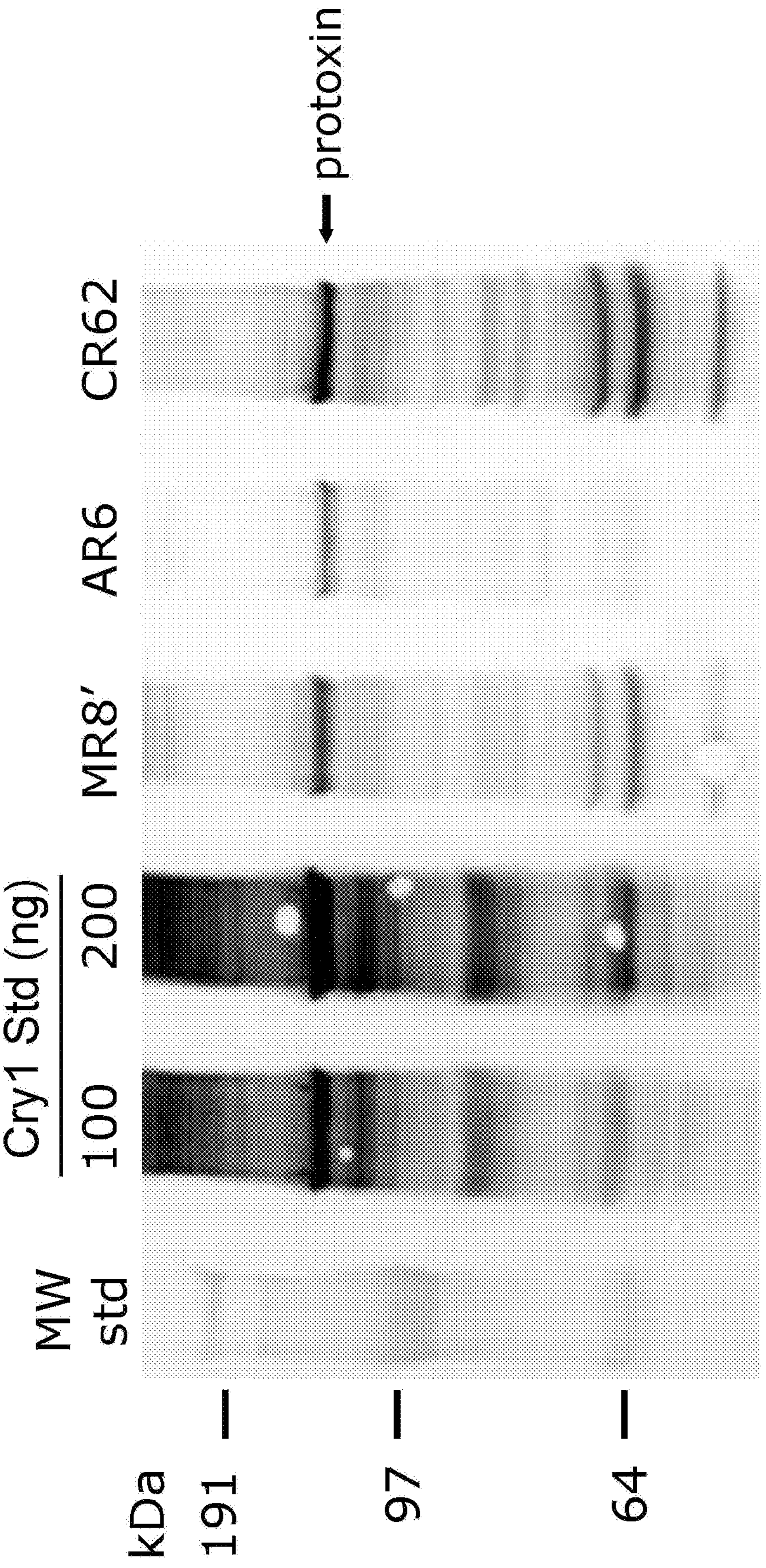

FIG. 4 shows the expression of synthetic AR6 (SEQ ID NO: 5), MR8' (SEQ ID NO: 11, and CR62 (SEQ ID NO: 9) genes in a transient leaf assay. The synthetic genes were expressed in *Nicotiana benthamiana* leaves using an *Agrobacterium* leaf infiltration assay. A western blot of resulting leaf extracts demonstrates the production of protoxin from the AR6, MR8', and CR62 synthetic genes. Lanes are as follows: molecular weight marker, 100 ng Cry1Ca protoxin standard, 200 ng Cry1Ca protoxin standard, extract from leaf expressing synthetic MR8', extract from leaf expressing synthetic AR6, extract from leaf expressing synthetic CR62. A rabbit polyclonal antiserum raised against purified Cry1Ca protein was used to probe the western blot (it had been predetermined that the Cry1Ca polyclonal antiserum cross-reacts strongly to AR6, CR62, and MR8' proteins).

Figure 5A:
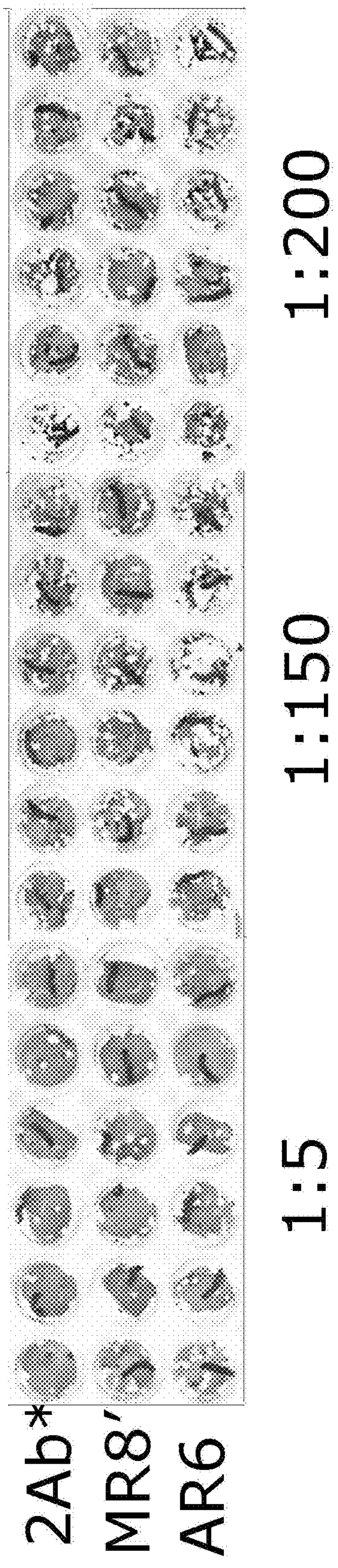
Figure 5B:
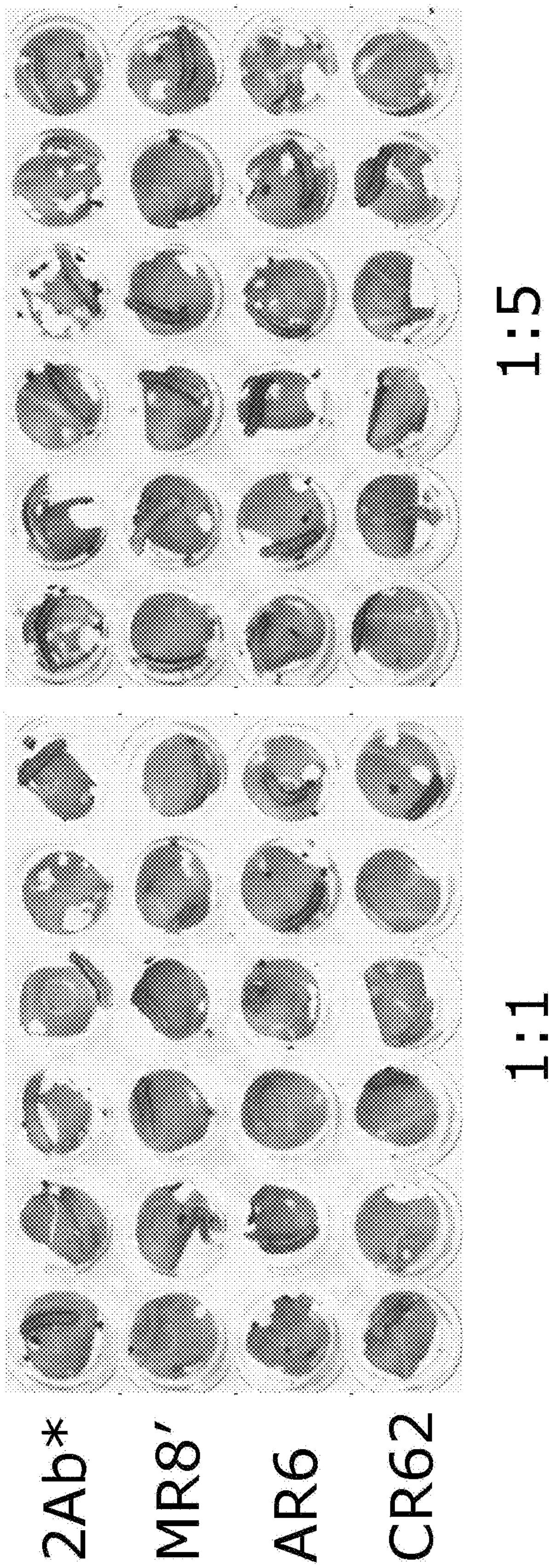

FIGS. 5A-5B show in planta insecticidal activity of synthetic AR6, MR8', and CR62 genes. Each variant was expressed in *N. benthamiana* using *Agrobacterium* infiltration. Each leaf disk was fed to (A) *H. zea* or (B) *S. exigua*. Following a 24-hour incubation period, the feeding activity was determined by visual observation. Positive controls for *H. zea* activity and *S. exigua* activity were a Cry2Ab-like polypeptide (SEQ ID NO: 35) and Cry1Ca shuffled gene CR62, respectively. The ratio shown for each panel refers to the relative amount of test *Agrobacterium* containing the gene of interest to *Agrobacterium* not containing a test gene. This dilution effectively reduces the level of test protein produced It should be noted that negative control leaves infiltrated with *Agrobacterium* not containing a test gene were completely consumed by the insect larvae during the assay period (not shown).

Figure 6:
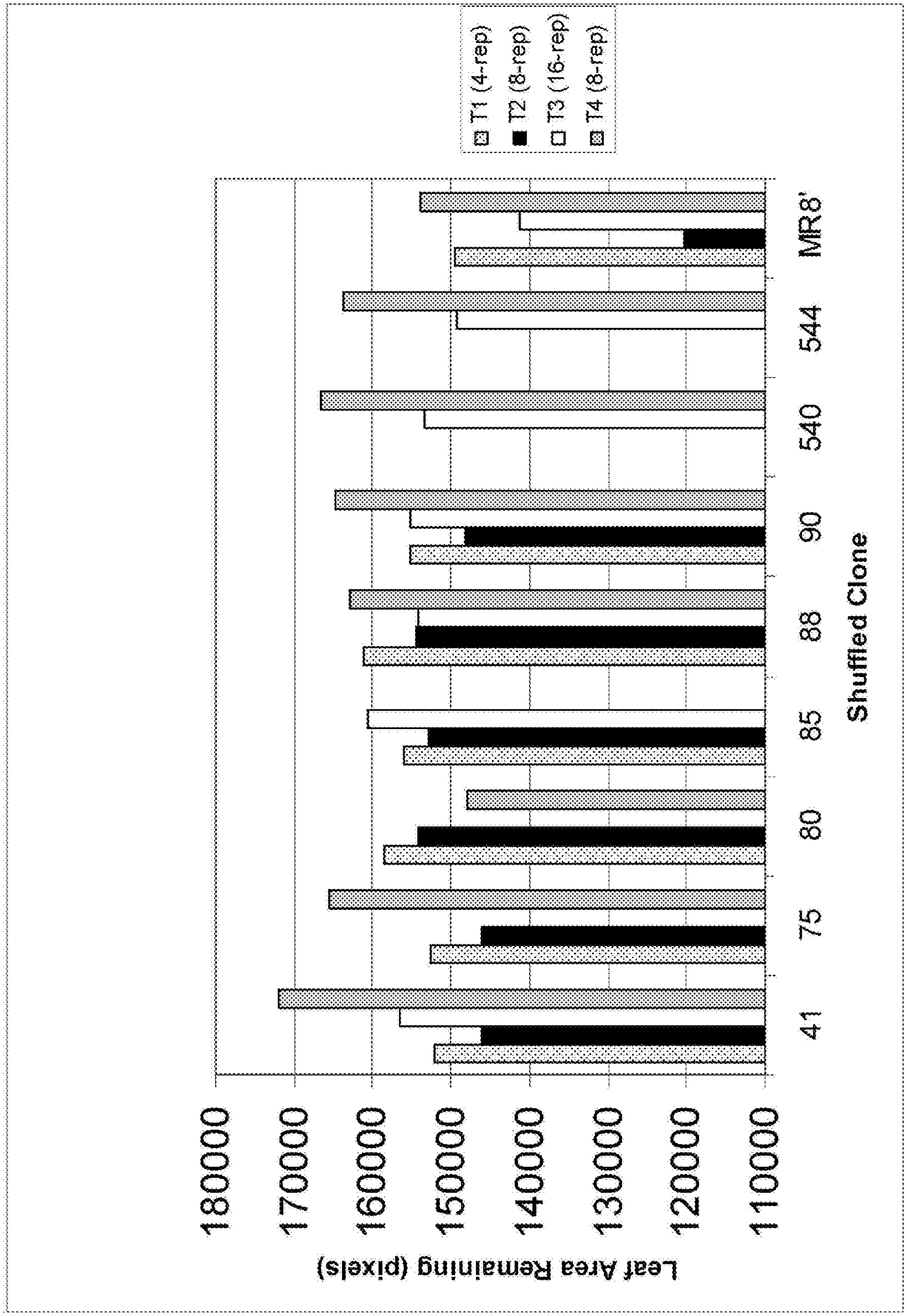

FIG. 6 shows in planta activity of MR8' shuffled variants against *H. zea*. The indicated variant was expressed in *N. benthamiana* leaves using *Agrobacterium* infiltration followed by a four day co-cultivation period. Each resulting leaf disk was fed to *H. zea*. Following a 24-hour incubation period, the feeding activity was determined by video capture of the leaf disk. The y-axis is the number of pixels present in the captured leaf disk image. The greater the number of pixels, the greater the amount of uneaten (protected) leaf remaining. The x-axis is the variant tested. The assay was repeated two to four times as indicated for each variant.

Figure 7:
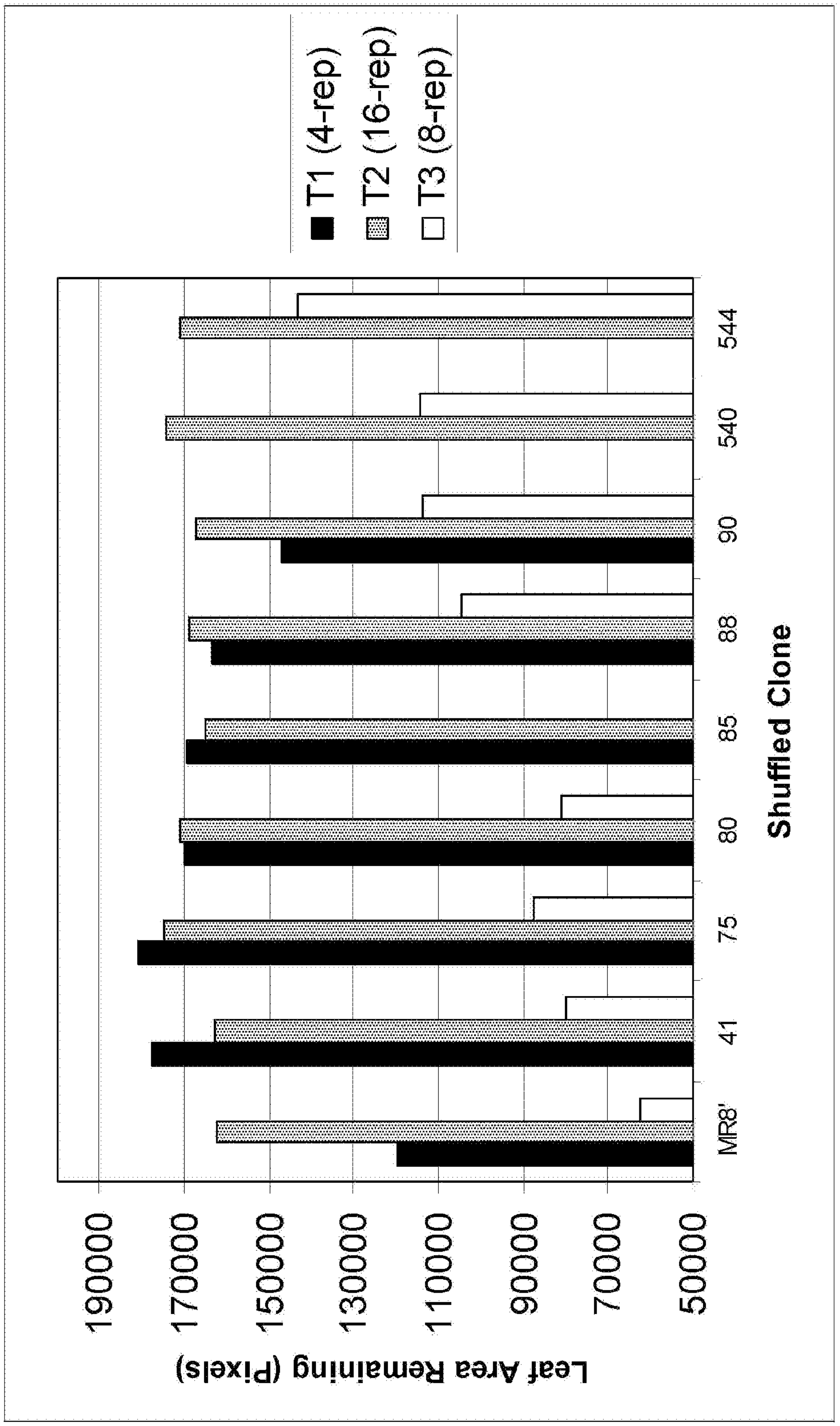

FIG. 7 shows in planta activity of MR8' shuffled variants against *S. exigua*. The indicated variant was expressed in *N. benthamiana* leaves using *Agrobacterium* infiltration followed by a four day co-cultivation period. Each resulting leaf disk was fed to *S. exigua*. Following a 24-hour incubation period, the feeding activity was determined by video capture of the leaf disk. The y-axis is the number of pixels present in the captured leaf disk image. The greater the number of pixels, the greater the amount of uneaten (protected) leaf remaining. The x-axis is the variant tested. The experiment was repeated 3 times.

DETAILED DESCRIPTION

The present invention provides insecticidal polypeptides related to *Bacillus* Cry1 polypeptides (e.g., Cry1Aa, Cry1Ab, Cry1Ac, Cry1Ad, Cry1Ae, Cry1Ag, and Cry1Ca). Nucleic acid molecules encoding the polypeptides of the invention are also provided. Methods for using the polypeptides and nucleic acids of the invention to enhance resistance of plants to insect predation are encompassed.

Polypeptides of the Invention

The present invention relates to Cry polypeptides derived from *Bacillus thuringiensis* Cry1 polypeptides (e.g., Cry1Aa, Cry1Ab, Cry1Ac, Cry1Ad, Cry1Ae, Cry1Ag, and Cry1Ca). In preferred embodiments, the Cry1-derived polypeptides represent the mature δ-endotoxin region and are selected from the group consisting of SEQ ID NOS: 2, 4, 6, 8, 10, 12, 14, 16, 18, 20, 22, 24, 26, 28. Polypeptides of the invention also encompass those polypeptides that are encoded by any Cry1-derived nucleic acid of the invention.

In addition to the polypeptide sequence of Cry1-derived polypeptides, it will be appreciated that polypeptides of the invention also encompass variants thereof, including, but not limited to, any substantially similar sequence, any fragment, analog, homolog, naturally occurring allele, or mutant thereof. Variants encompassed by the invention are polypeptides that are at least partially functionally active, i.e., they are capable of displaying one or more known functional activities associated with a wild type Cry1 polypeptide. Such functional activities include, but are not limited to, biological activities, such as insecticidal activity; antigenicity, i.e., an ability to bind or compete with a wild type Cry1 for binding to an anti-Cry1 antibody; immunogenicity, i.e., an ability to generate antibody which binds to a wild type Cry1 polypeptide. In some embodiments, the variants have at least one functional activity that is substantially similar to its parent polypeptide (e.g., a variant of Cry1-derived polypeptide will have at least one functional activity that is substantially similar to the Cry1-derived polypeptide to which it is most similar). As used herein, the functional activity of the variant will be considered "substantially similar" to its parent polypeptide if it is within one standard deviation of the parent.

In one embodiment, shuffled mature δ-endotoxin polypeptides that have at least one Cry1 functional activity (e.g., insecticidal activity) and are at least 90%, 91%, 92%, 93%, 94%, 95%, 96% 97%, 98%, 99% or 99.5% identical to the polypeptide sequence of any of SEQ ID NOS: 2, 4, 6, 8, 10, 12, 14, 16, 18, 20, 22, 24, 26, 28 are encompassed by the invention.

As used herein, where a sequence is defined as being "at least X % identical" to a reference sequence, e.g., "a polypeptide at least 95% identical to SEQ ID NO: 2," it is to be understood that "X % identical" refers to absolute percent identity, unless otherwise indicated. The term "absolute percent identity" refers to a percentage of sequence identity determined by scoring identical amino acids or nucleic acids as one and any substitution as zero, regardless of the similarity of mismatched amino acids or nucleic acids. In a typical sequence alignment the "absolute percent identity" of two sequences is presented as a percentage of amino acid or nucleic acid "identities." In cases where an optimal alignment of two sequences requires the insertion of a gap in one or both of the sequences, an amino acid residue in one sequence that aligns with a gap in the other sequence is counted as a mismatch for purposes of determining percent identity. Gaps can be internal or external, i.e., a truncation. Absolute percent identity can be readily determined using, for example, the Clustal W program, version 1.8, June 1999, using default parameters (Thompson et al., 1994, *Nucleic Acids Research* 22: 4673-4680).

In another embodiment, mature δ-endotoxin polypeptides that have at least one Cry1 functional activity (e.g., insecticidal activity), are at least 99% or 99.5% identical to the polypeptide sequence of any of SEQ ID NOS: 2, 4, 6, 8, 10, 12, 14, 16, 18, 20, 22, 24, 26, 28 and are encoded by a polynucleotide that hybridizes under stringent conditions to a nucleic acid that encodes any of SEQ ID NOS: 2, 4, 6, 8, 10, 12, 14, 16, 18, 20, 22, 24, 26, 28.

In a specific embodiment, a fragment of the invention corresponds to the length of the processed pro-toxin. The toxin corresponds to the N-terminal portion of the full length Cry1 polypeptide. In preferred embodiments, the N-terminal ~50 kDa-75 kDa fragment corresponds to the toxin. In more preferred embodiments, the N-terminal ~66 kDa fragment corresponds to the toxin. Polypeptides that correspond to this processed Cry1 fragment can be provided in the methods of the present invention directly to circumvent the need for pro-toxin processing.

The full protoxin nucleotide or polypeptide sequences are made up of the domain I, II, and III toxin regions in the context of the protoxin 5' or N-terminal and 3' or C-terminal protoxin regions. In some cases the protoxin and toxin regions are derived from the same Cry1-type molecule, such as CR62 being fully derived from Cry1Ca. In other cases the 5' or N-terminal region is derived primarily from one molecule while the C-terminal protoxin region is derived from another such as with AR6, MR8' and derivatives in which the 5' or N-terminal region is predominantly derived from Cry1Ab while the 3' or C-terminal region corresponding to the protoxin region is from Cry1Ca. It is recognized that the active 6-endotoxin region of the molecules could retain the exact activity in the context of a different set of protoxin sequences derived from other Cry1 molecules.

In another specific embodiment, a fragment of the invention corresponds to a Cry1 domain. Mature Cry1 toxin polypeptides have three domains including i) domain I which is involved in insertion into the insect apical midgut membrane and affects ion channel function, ii) domain II which is involved in receptor binding on the insect midgut epithelial cell membrane, and iii) domain III which is involved in ion channel function, receptor binding, and insertion into the membrane (Schnepf et al., 1998, *Microbiol. Molec. Biol. Rev.* 62:775-806).

In another embodiment, analog polypeptides are encompassed by the invention. Analog polypeptides may possess residues that have been modified, i.e., by the covalent attachment of any type of molecule to the Cry1-derived polypeptides. For example, but not by way of limitation, an analog polypeptide of the invention may be modified, e.g., by glycosylation, acetylation, pegylation, phosphorylation, amidation, derivatization by known protecting/blocking groups, proteolytic cleavage, linkage to a cellular ligand or other protein, etc. An analog polypeptide of the invention may be modified by chemical modifications using techniques known to those of skill in the art, including, but not limited to specific chemical cleavage, acetylation, formylation, synthesis in the presence of tunicamycin (an inhibitor of N-linked glycosylation and the formation of N-glycosidic protein-carbohydrate linkages), etc. Furthermore, an analog of a polypeptide of the invention may contain one or more non-classical amino acids.

Methods of production of the polypeptides of the invention, e.g., by recombinant means, are also provided.

Compositions comprising one or more polypeptides of the invention are also encompassed. The compositions of the invention can further comprise additional agents including, but not limited to, spreader-sticker adjuvants, stabilizing agents, other insecticidal additives, diluents, agents that optimize the rheological properties or stability of the composition, such as, for example, surfactants, emulsifiers, dispersants, and/or polymers.

Nucleic Acids of the Invention

The present invention also relates to Cry1-derived nucleic acid molecules. In preferred embodiments, the Cry1-derived nucleic acid molecules are selected from the group consisting of SEQ ID NOS: 1, 3, 5, 7, 9, 11, 13, 15, 17, 19, 21, 23, 25, and 27. Nucleic acid molecules of the invention also encompass those nucleic acid molecules that encode any Cry1-derived polypeptide of the invention.

In addition to the nucleic acid molecule of Cry1-derived nucleic acid molecules, it will be appreciated that nucleic acids of the invention also encompass variants thereof, including, but not limited to any substantially similar sequence, any fragment including the toxin fragment, homolog, naturally occurring allele, or mutant thereof. Variant nucleic acid molecules encompassed by the present invention encode polypeptides that are at least partially functionally active, i.e., they are capable of displaying one or more known functional activities associated with a wild type Cry1 polypeptide. Such functional activities include, but are not limited to, biological activities, such as insecticidal activity; antigenicity, i.e., an ability to bind or compete with a wild type Cry1 for binding to an anti-Cry1 antibody; immunogenicity, i.e., an ability to generate antibody which binds to a wild type Cry1 polypeptide. In some embodiments, the variants have at least one functional activity that is substantially similar to its parent nucleic acid molecule (e.g., a variant of a Cry1-derived nucleic acid molecule will encode a polypeptide that has at least one functional activity that is substantially similar to the polypeptide encoded for by the Cry1-derived nucleic acid molecule to which it most similar). As used herein, the functional activity of the variant will be considered "substantially similar" to its parent polypeptide if it is within one standard deviation of the parent.

In one embodiment, shuffled nucleic acid molecules that are at least 90%, 91%, 92%, 93%, 94%, 95%, 96% 97%, 98%, 99% or 99.5% identical to any of the nucleic acid molecules of SEQ ID NOS: 1, 3, 5, 7, 9, 11, 13, 15, 17, 19, 21, 23, 25, 27 are encompassed by the invention. In another embodiment, nucleic acid molecules that are at least 99% or 99.5% identical to any of the nucleic acid molecules of SEQ ID NOS: 1, 3, 5, 7, 9, 11, 13, 15, 17, 19, 21, 23, 25, 27 are encompassed by the invention.

To determine the percent identity of two nucleic acid molecules, the sequences are aligned for optimal comparison purposes (e.g., gaps can be introduced in the sequence of a first nucleic acid molecule for optimal alignment with a second or nucleic acid molecule). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A non-limiting example of a mathematical algorithm utilized for the comparison of two sequences is the algorithm of Karlin and Altschul (Karlin and Altschul, 1990, *Proc. Natl. Acad. Sci.* 87:2264-2268, modified as in Karlin and Altschul, 1993, *Proc. Natl. Acad. Sci.* 90:5873-5877). Such an algorithm is incorporated into the NBLAST and XBLAST programs (Altschul et al., 1990, *J. Mol. Biol.* 215: 403 and Altschul et al., 1997, *Nucleic Acid Res.* 25:3389-3402). Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=⁻4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989, PNAS, 89:10915).

The Clustal V method of alignment can also be used to determine percent identity (Higgins and Sharp, 1989, CABIOS. 5:151-153) and found in the Megalign program of the LASERGENE bioinformatics computing suite (DNASTAR Inc., Madison, Wis.). The "default parameters" are the parameters pre-set by the manufacturer of the program and for multiple alignments they correspond to GAP PENALTY=10 and GAP LENGTH PENALTY=10, while for pairwise alignments they are KTUPLE 1, GAP PENALTY=3, WINDOW=5 and DIAGONALS SAVED=5. After alignment of the sequences, using the Clustal V program, it is possible to obtain a "percent identity" by viewing the "sequence distances" table on the same program.

The percent identity between two sequences can be determined using techniques similar to those described above, with or without allowing gaps. In calculating percent identity, typically only exact matches are counted.

In another embodiment, nucleic acid molecules incorporating any of the herein-described nucleic acid molecules of Cry1-derived nucleic acid molecules are encompassed by the invention. Nucleic acid molecules are encompassed that have at least one Cry1 functional activity (e.g., insecticidal activity). In this regard, the described sequences encoding the toxin may be combined with domains from other Cry proteins to form the complete Cry protein.

In a specific embodiment, the combination corresponds to a nucleic acid molecule that encodes a complete Cry protein. The toxin corresponds to the N-terminal portion of the full length Cry1 polypeptide. Nucleic acid molecules encoding domain I and nucleic acid molecules encoding domain II may then be combined with the described nucleic acid molecules to form a nucleic acid molecule encoding a mature Cry protein.

In another specific embodiment, a fragment of the invention encodes a polypeptide that corresponds to any of domains I, II or III of a mature Cry1 toxin.

In another embodiment, a nucleic acid molecule that hybridizes under stringent conditions to any one of SEQ ID NOS: 1, 3, 5, 7, 9, 11, 13, 15, 17, 19, 21, 23, 25, 27 is encompassed by the invention. The phrase "stringent conditions" refers to hybridization conditions under which a nucleic acid will hybridize to its target nucleic acid, typically in a complex mixture of nucleic acid, but to essentially no other nucleic acids. Stringent conditions are sequence-dependent and will be different in different circumstances. Longer nucleic acids hybridize specifically at higher temperatures. Extensive guides to the hybridization of nucleic acids can be found in the art (e.g., Tijssen, *Techniques in Biochemistry and Molecular Biology—Hybridization with Nucleic Probes*, "Overview of principles of hybridization and the strategy of nucleic acid assays" (1993)). Generally, highly stringent conditions are selected to be about 5-10° C. lower than the thermal melting point ($T_m$) for the specific nucleic acid at a defined ionic strength and pH. Low stringency conditions are generally selected to be about 15-30° C. below the $T_m$. The $T_m$ is the temperature (under defined ionic strength, pH, and nucleic acid concentration) at which 50% of the probes complementary to the target hybridize to the target nucleic acid at equilibrium (as the target nucleic acids are present in excess, at $T_m$, 50% of the probes are occupied at equilibrium). Hybridization conditions are typically those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, and preferably 10 times background hybridization. In one embodiment, stringent conditions include at least one wash (usually 2) in 0.2×SSC at a temperature of at least about 50° C., usually about 55° C., or sometimes 60° C. or 65° C., for 20 minutes, or substantially equivalent conditions. In a specific embodiment, the nucleic acid molecule of the invention specifically hybridizes following at least one wash in 0.2×SSC at 55° C. for 20 minutes to a polynucleotide encoding the polypeptide of any of SEQ ID NOS:2, 4, 6, 8, 10, 12, 14, 16, 18, 20, 22, 24, 26, 28. In another embodiment, stringent conditions include hybridization in 6× sodium chloride/sodium citrate (SSC) at about 45° C. followed by one or more washes in 0.2×SSC, 0.1% SDS at 50-65° C.

The phrase "specifically hybridizes" refers to the binding, duplexing, or hybridizing of a molecule only to a particular nucleotide sequence under stringent hybridization conditions when that sequence is present in a complex mixture (e.g., total cellular or library DNA or RNA).

Vectors comprising nucleic acids of the invention are also encompassed. Cells or plants comprising the vectors of the invention are also encompassed.

The term "nucleic acid" or "nucleic acid molecule" herein refer to a single or double-stranded polymer of deoxyribonucleotide or ribonucleotide bases read from the 5' to the 3' end. It includes chromosomal DNA, self-replicating plasmids and DNA or RNA that performs a primarily structural role. The term "encoding" refers to a polynucleotide sequence encoding one or more amino acids. The term does not require a start or stop codon. An amino acid sequence can be encoded in any one of six different reading frames provided by a polynucleotide sequence and its complement.

Table 1 discloses Cry1-derived sequences and the corresponding sequence identity number.

Cry1-Derived Sequences

Cry1-derived polypeptides and nucleic acid molecules of the invention can be created by introducing one or more nucleotide substitutions, additions and/or deletions into the nucleotide sequence of a wild type Cry1 (e.g., Cry1Aa, Cry1Ab, Cry1Ac, Cry1Ad, Cry1Ae, Cry1Ag, and Cry1Ca) or related nucleic acids, such that one or more amino acid substitutions, additions and/or deletions are introduced into the encoded protein. Generally, Cry1-derived sequences are created in order to accentuate a desirable characteristic or reduce an undesirable characteristic of a wild type Cry1 polypeptide. In one embodiment, Cry1-derived polypeptides have improved insecticidal activity over the corresponding wild type Cry1 including, but not limited to, greater potency and/or increased insect pest range. In another embodiment, Cry1-derived polypeptides are expressed better than the corresponding wild type Cry1 in a microbial host or a plant host including, but not limited to, increased half life, less susceptible to degradation, and/or more efficient transcription or translation.

In one embodiment, *Bacillus thuringiensis* derived Cry1Ab (SEQ ID NO: 33) or Cry1Ca (SEQ ID NO: 29, coding region: 47-3616) nucleic acid molecules were used as a templates to create shuffled cry1 nucleotide fragments. In another embodiment, variants isolated from one round of alteration can be used as template for further rounds of alteration (e.g., AR6, CR62, or MR8'). In another embodiment, templates encoding Cry1 proteins to be altered or shuffled can be re-synthesized to have a different nucleic acid sequence to provide improved expression in host cells for screening and/or commercialization purposes. Each of the Cry 1-type molecules described herein whether derived from the 5' or N-terminal region of Cry1Ab or Cry1Ca contain the protoxin 3' or C-terminal region of Cry1Ca.

Sequence alterations can be introduced by standard techniques such as directed molecular evolution techniques e.g., DNA shuffling methods (see e.g., Christians et al., 1999, *Nature Biotechnology* 17:259-264; Crameri et al., 1998, *Nature,* 391:288-291; Crameri, et al., 1997, *Nature Biotechnology* 15:436-438; Crameri et al., 1996, *Nature Biotechnology* 14:315-319; Stemmer, 1994, *Nature* 370:389-391; Stemmer et al., 1994, *Proc. Natl. Acad. Sci.,* 91:10747-10751; U.S. Pat. Nos. 5,605,793; 6,117,679; 6,132,970; 5,939,250; 5,965,408; 6,171,820; International Publication Nos. WO 95/22625; WO 97/0078; WO 97/35966; WO 98/27230; WO 00/42651; and WO 01/75767); site directed mutagenesis (see e.g., Kunkel, 1985, *Proc. Natl. Acad. Sci.,* 82:488-492; Oliphant et al., 1986, *Gene* 44:177-183); oligonucleotide-directed mutagenesis (see e.g., Reidhaar-Olson et al., 1988, *Science* 241:53-57); chemical mutagenesis (see e.g., Eckert et al., 1987, *Mutat. Res.* 178:1-10); error prone PCR (see e.g., Caldwell & Joyce, 1992, *PCR Methods Applic.* 2:28-33); and cassette mutagenesis (see e.g., Arkin et al., *Proc. Natl. Acad. Sci.,* 1992, 89:7871-7815); (see generally, e.g., Arnold, 1993, *Curr. Opinion Biotechnol.* 4:450-455; Ling et al., 1997, *Anal. Biochem.,* 254(2):157-78; Dale et al., 1996, *Methods Mol. Biol.* 57:369-74; Smith, 1985, *Ann. Rev. Genet.* 19:423-462; Botstein et al., 1985, *Science,* 229:1193-1201; Carter, 1986, *Biochem. J.* 237:1-7; Kramer et al., 1984, *Cell* 38:879-887; Wells et al., 1985, *Gene* 34:315-323; Minshull et al., 1999, *Current Opinion in Chemical Biology* 3:284-290).

In one embodiment, DNA shuffling is used to create Cry1-derived nucleic acid molecules. DNA shuffling can be accomplished in vitro, in vivo, in silico, or a combination thereof. In silico methods of recombination can be performed in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis gene reassembly techniques. This approach can generate random, partially random or designed alterations. Many details regarding in silico recombination, including the use of genetic algorithms, genetic operators and the like in computer systems, combined with generation of corresponding nucleic acids as well as combinations of designed nucleic acids (e.g., based on cross-over site selection) as well as designed, pseudo-random or random recombination methods are described in the art (see e.g., International Publication Nos. WO 00/42560 and WO 00/42559).

In another embodiment, targeted mutagenesis is used to create Cry1-derived nucleic acid molecules by choosing particular nucleotide sequences or positions of the corresponding wild type Cry1 or related nucleic acid molecules for alteration. Such targeted mutations can be introduced at any position in the nucleic acid. For example, one can make nucleotide substitutions leading to amino acid substitutions at "non-essential" or "essential" amino acid residues. A "non-essential" amino acid residue is a residue that can be altered from the wild-type sequence without altering the biological activity, whereas an "essential" amino acid residue is required for at least one biological activity of the polypeptide. For example, amino acid residues that are not conserved or only semi-conserved among homologs of various species may be non-essential for activity. Alternatively, amino acid residues that are conserved among the homologs of various species may be essential for activity.

Such targeted mutations can be conservative or non-conservative. A "non-conservative amino acid substitution" is one in which the amino acid residue is replaced with an amino acid residue having a dissimilar side chain. Families of amino acid residues having similar side chains have been defined in the art. These families include amino acids with basic side chains (e.g., lysine, arginine, histidine), acidic side chains (e.g., aspartic acid, glutamic acid, asparagine, glutamine), uncharged polar side chains (e.g., glycine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

Alternatively or in addition to non-conservative amino acid residue substitutions, such targeted mutations can be conservative. A "conservative amino acid substitution" is one in which the amino acid residue is replaced with an amino acid residue having a similar side chain. Following mutagenesis, the encoded protein can be expressed recombinantly and the activity of the protein can be determined.

In another embodiment, random mutagenesis is used to create Cry1-derived nucleotides. Mutations can be introduced randomly along all or part of the coding sequence (e.g., by saturation mutagenesis or by error prone PCR). In certain embodiments, nucleotide sequences encoding other related polypeptides that have similar domains, structural motifs, active sites, or that align with a portion of the Cry1 of the invention with mismatches or imperfect matches, can be used in the mutagenesis process to generate diversity of sequences.

It should be understood that for each mutagenesis step in some of the techniques mentioned above, a number of iterative cycles of any or all of the steps may be performed to optimize the diversity of sequences. The above-described methods can be used in combination in any desired order. In many instances, the methods result in a pool of altered nucleic acid sequences or a pool of recombinant host cells comprising altered nucleic acid sequences. The altered nucleic acid sequences or host cells expressing an altered nucleic acid sequence with the desired characteristics can be identified by screening with one or more assays known in the art. The assays may be carried out under conditions that select for polypeptides possessing the desired physical or chemical characteristics. The alterations in the nucleic acid sequence can be determined by sequencing the nucleic acid molecule encoding the altered polypeptide in the variants.

Additionally, Cry1-derived nucleic acid molecules can be codon optimized, either wholly or in part. Because any one amino acid (except for methionine and tryptophan) is encoded by a number of codons (Table 2), the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art.

Methods of Assaying Insecticidal Activity

As used herein, the term "insecticidal activity" refers to the ability of a polypeptide to decrease or inhibit insect feeding and/or to increase insect mortality upon ingestion of the polypeptide. Although any insect may be affected, preferably insects of the Lepidopteran order including the *Helicoverpa, Heliothis*, or *Spodoptera* genera of insects are affected.

A variety of assays can be used to determine whether a particular polypeptide of the invention has insecticidal activity and, if so, to what degree. Generally, an insect pest is provided a polypeptide of the invention in any form that can be ingested. The reaction of the insect pest to ingestion of the polypeptide of the invention is observed (e.g., for about one to three days). A decrease or inhibition of feeding and/or an increase in insect pest mortality after ingestion of the polypeptide of the invention are indicators of insecticidal activity. A polypeptide of the invention with unknown insecticidal activity should be compared to a positive and/or negative control to assess more accurately the outcome of the assay.

In one embodiment, a polypeptide of the invention is purified (either in soluble form or in crystal form) and added to the insect diet.

In another embodiment, a polypeptide of the invention is expressed in a recombinant microbe (e.g., *E. coli*). The recombinant microbe is fed directly to the insect pests (see Moellenbeck et al., 2001, *Nat. Biotechnol.* 19:668).

In another embodiment, the polypeptide of the invention is expressed in a plant and the plant is fed to the insect pest. Following the incubation period, the feeding activity of the insect pest can be determined by visual observation (e.g., of approximate fraction of leaf area remaining) or video capture (e.g., number of pixels in a leaf area remaining) of the plant parts that would normally have been eaten by the insect pest. In a specific embodiment, expression of the polypeptide of the invention in the plant is transient. In such embodiments, a nucleic acid encoding a polypeptide of the invention is cloned into a plant expression vector and transfected into *Agrobacterium tumefaciens*. The transformed bacterial culture is co-cultivated with a leaf from *N. benthamiana* and, using forced infiltration, the leaf expresses the polypeptide of the invention. However, expression of the polypeptide is variable between leaf co-cultures. In another specific embodiment, expression of the polypeptide of the invention in the plant is stable. In such embodiments, a transgenic plant is made that expresses a polypeptide of the invention.

In another embodiment, insecticidal activity of a polypeptide of the invention can be assayed by measuring cell death and/or cell growth using cultured cells. Such assays typically involve the use of cultured insect cells that are susceptible to the particular toxin being screened, or cells that express a receptor for the particular toxin, either naturally or as a result of expression of a heterologous gene. Thus, in addition to insect cells, mammalian, bacterial, and yeast cells are among those cells useful in the in vitro assays. In vitro bioassays which measure toxicity against cultured cells are described in the art (e.g., Johnson, 1994, *J. Invertebr. Pathol.* 63:123-129).

In another embodiment, insecticidal activity of a polypeptide of the invention can be assayed by measuring pore formation in target insect-derived midgut epithelial membrane vesicles (Juttner and Ebel, 1998, *Biochim. Biophys. Acta* 1370:51-63; English et al., 1991, *Insect Biochem.* 21:177-184). Such an assay may constitute toxin conditional release of a ligand activated substrate from the lumen of the membrane vesicles. This requires that the ligand be on the outside of the vesicle. Alternatively the reverse scenario may be utilized whereby the ligand is in the vesicle lumen and the ready to be activated substrate is located on the outside of the vesicle. The higher the toxin activity the greater the number or size of pores formed.

Methods of Enhancing Insect Resistance in Plants

The present invention provides methods of enhancing plant resistance to insect pests including, but not limited to, members of the *Helicoverpa* ssp. (e.g., *Helicoverpa Zea* and *Heliothis virescens*) and/or *Spodoptera* ssp. (e.g., *Spodoptera exigua, Spodoptera frugiperda*) through the use of Cry1-derived insecticidal polypeptides. Any method known in the art can be used to cause the insect pests to ingest one or more polypeptides of the invention during the course of feeding on the plant. As such, the insect pest will ingest insecticidal amounts of the one or more polypeptides of the invention and may discontinue feeding on the plant. In some embodiments, the insect pest is killed by ingestion of the one or more polypeptides of the invention. In other embodiments, the insect pests are inhibited or discouraged from feeding on the plant without being killed.

In one embodiment, transgenic plants can be made to express one or more polypeptides of the invention. The transgenic plant may express the one or more polypeptides of the invention in all tissues (e.g., global expression). Alternatively, the one or more polypeptides of the invention may be expressed in only a subset of tissues (e.g., tissue specific expression), preferably those tissues consumed by the insect pest. Polypeptides of the invention can be expressed constitutively in the plant or be under the control of an inducible promoter. Polypeptides of the invention may be expressed in the plant cytosol or in the plant chloroplast either by protein targeting or by transformation of the chloroplast genome.

In another embodiment, a composition comprising one or more polypeptides of the invention can be applied externally to a plant susceptible to the insect pests. External application of the composition includes direct application to the plant, either in whole or in part, and/or indirect application, e.g., to the environment surrounding the plant such as the soil. The composition can be applied by any method known in the art including, but not limited to, spraying, dusting, sprinkling, or the like. In general, the composition can be applied at any time during plant growth. One skilled in the art can use methods known in the art to determine empirically the optimal time for administration of the composition. Factors that affect optimal administration time include, but are not limited to, the type of susceptible plant, the type of insect pest, which one or more polypeptides of the invention are administered in the composition.

The composition comprising one or more polypeptides of the invention may be substantially purified polypeptides, a cell suspension, a cell pellet, a cell supernatant, a cell extract, or a spore-crystal complex of *Bacillus thuringiensis* cells. The composition comprising one or more polypeptides of the invention may be in the form of a solution, an emulsion, a suspension, or a powder. Liquid formulations may be aqueous or non-aqueous based and may be provided as foams, gels, suspensions, emulsifiable concentrates, or the like. The formulations may include agents in addition to the one or more polypeptides of the invention. For example, compositions may further comprise spreader-sticker adjuvants, stabilizing agents, other insecticidal additives, diluents, agents that optimize the rheological properties or stability of the composition, such as, for example, surfactants, emulsifiers, dispersants, or polymers.

In another embodiment, recombinant hosts that express one or more polypeptides of the invention are applied on or near a plant susceptible to attack by an insect pest. The recombinant hosts include, but are not limited to, microbial hosts and insect viruses that have been transformed with and express one or more nucleic acid molecules (and thus polypeptides) of the invention. In some embodiments, the recombinant host secretes the polypeptide of the invention into its surrounding environment so as to contact an insect pest. In other embodiments, the recombinant hosts colonize one or more plant tissues susceptible to insect infestation.

Recombinant Expression

Nucleic acid molecules and polypeptides of the invention can be expressed recombinantly using standard recombinant DNA and molecular cloning techniques that are well known in the art (e.g., Sambrook, Fritsch, and Maniatis, *Molecular Cloning: A Laboratory Manual*; Cold Spring Harbor Laboratory Press: Cold Spring Harbor, 1989). Additionally, recombinant DNA techniques may be used to create nucleic acid constructs suitable for use in making transgenic plants.

Accordingly, an aspect of the invention pertains to vectors, preferably expression vectors, comprising a nucleic acid molecule of the invention, or a variant thereof. As used herein, the term "vector" refers to a polynucleotide capable of transporting another nucleic acid to which it has been linked. One type of vector is a "plasmid", which refers to a circular double stranded DNA loop into which additional DNA segments can be introduced. Another type of vector is a viral vector, wherein additional DNA segments can be introduced into the viral genome.

Certain vectors are capable of autonomous replication in a host cell into which they are introduced (e.g., bacterial vectors having a bacterial origin of replication and episomal vectors). Other vectors (e.g., non-episomal vectors) are integrated into the genome of a host cell upon introduction into the host cell, and thereby are replicated along with the host genome. In general, expression vectors of utility in recombinant DNA techniques are often in the form of plasmids (vectors). However, the invention is intended to include such other forms of expression vectors, such as viral vectors (e.g., replication defective retroviruses).

The recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably associated with the polynucleotide to be expressed. Within a recombinant expression vector, "operably associated" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described in the art (e.g., Goeddel, *Gene Expression Technology: Methods in Enzymology,* 1990, Academic Press, San Diego, Calif.). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, the area of the organism in which expression is desired, etc. The expression vectors of the invention can be introduced into host cells to thereby produce proteins or peptides, including fusion proteins or peptides, encoded by nucleic acids molecules as described herein.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, U.S. Pat. No. 5,565,350; International Patent Application No. PCT/US93/03868), or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell.

If polypeptide expression is desired in a eukaryotic system, it is generally desirable to include a polyadenylation region at the 3'-end of a polynucleotide coding region. The polyadenylation region for plant expression can be derived from the natural gene, from a variety of plant genes, or from *Agrobacterium* T-DNA. The 3' end sequence to be added can be derived from, for example, the nopaline synthase or octopine synthase genes, or alternatively from another plant gene, or less preferably from any other eukaryotic gene.

The recombinant expression vectors of the invention can be designed for expression of a polypeptide of the invention in prokaryotic (e.g., *Enterobacteriaceae*, such as *Escherichia;*

*Bacillaceae; Rhizoboceae*, such as *Rhizobium* and *Rhizobacter; Spirillaceae*, such as photobacterium; *Zymomonas; Serratia; Aeromonas; Vibrio; Desulfovibrio; Spirillum; Lactobacillaceae; Pseudomonadaceae*, such as *Pseudomonas* and *Acetobacter; Azotobacteraceae* and *Nitrobacteraceae*) or eukaryotic cells (e.g., insect cells using baculovirus expression vectors, yeast cells, plant cells, or mammalian cells) (see Goeddel, supra. For a discussion on suitable host cells). Alternatively, the recombinant expression vector can be transcribed and translated in vitro, for example using T7 promoter regulatory sequences and T7 polymerase.

Expression of proteins in prokaryotes is most often carried out in *E. coli* with vectors comprising constitutive or inducible promoters directing the expression of either fusion or non-fusion proteins. Fusion vectors add a number of amino acids to a protein encoded therein, usually to the amino terminus of the recombinant protein. Such fusion vectors typically serve at least three purposes: 1) to increase expression of the recombinant protein; 2) to increase the solubility of the recombinant protein; and/or 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corp., San Diego, Calif.), and pPicZ (Invitrogen Corp., San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell. Biol.* 3:2156-2165) and the pVL series (Lucklow and Summers, 1989, *Virology* 170:31-39).

In yet another embodiment, a nucleic acid of the invention is expressed in plant cells using a plant expression vector including, but not limited to, tobacco mosaic virus and potato virus expression vectors.

Other suitable expression systems for both prokaryotic and eukaryotic cells are known in the art (see, e.g., chapters 16 and 17 of Sambrook et al. 1990, *Molecular Cloning, A Laboratory Manual,* 2d ed., Cold Spring Harbor Laboratory, Cold Spring Harbor, N.Y.).

A number of promoters can be used in the practice of the invention. The promoters can be selected based on the desired outcome. The nucleic acids can be combined with constitutive, tissue-specific, inducible, or other promoters for expression in the host organism.

A "tissue-specific promoter" may direct expression of nucleic acids of the present invention in a specific tissue, organ or cell type. Tissue-specific promoters can be inducible. Similarly, tissue-specific promoters may only promote transcription within a certain time frame or developmental stage within that tissue. Other tissue specific promoters may be active throughout the life cycle of a particular tissue. One of ordinary skill in the art will recognize that a tissue-specific promoter may drive expression of operably linked sequences in tissues other than the target tissue. Thus, as used herein, a tissue-specific promoter is one that drives expression preferentially in the target tissue or cell type, but may also lead to some expression in other tissues as well. A number of tissue-specific promoters can be used in the present invention. With the appropriate promoter, any organ can be targeted, such as shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit. For instance, promoters that direct expression of nucleic acids in leaves, roots or flowers are useful for enhancing resistance to pests that infect those organs. For expression of a polynucleotide of the present invention in the aerial vegetative organs of a plant, photosynthetic organ-specific promoters, such as the RBCS promoter (Khoudi et al., Gene 197:343, 1997), can be used. Root-specific expression of polynucleotides of the present invention can be achieved under the control of a root-specific promoter, such as, for example, the promoter from the ANR1 gene (Zhang and Forde, *Science,* 279:407, 1998). Other exemplary promoters include the root-specific glutamine synthetase gene from soybean (Hirel et al., 1992, *Plant Molecular Biology* 20:207-218) and the root-specific control element in the GRP 1.8 gene of French bean (Keller et al., 1991, *The Plant Cell* 3:1051-1061).

A "constitutive promoter" is defined as a promoter which will direct expression of a gene in all tissues and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of ordinary skill in the art. Such genes include for example, ACT11 from *Arabidopsis* (Huang et al. 1996, *Plant Mol. Biol.* 33:125-139), Cat3 from *Arabidopsis* (GenBank Accession No. U43147, Zhong et al., 1996, *Mol. Gen. Genet.* 251:196-203), the gene encoding stearoyl-acyl carrier protein desaturase from *Brassica napus* (Genbank Accession No. X74782, Solocombe et al. 1994, *Plant Physiol.* 104:1167-1176), GPc1 from maize (GenBank Accession No. X15596, Martinez et al., 1989, *J. Mol. Biol.* 208:551-565), and Gpc2 from maize (GenBank Accession No. U45855, Manjunath et al., 1997, *Plant Mol. Biol.* 33:97-112). Any strong, constitutive promoter, such as the CaMV 35S promoter, can be used for the expression of polynucleotides of the present invention throughout the plant.

The term "inducible promoter" refers to a promoter that is under precise environmental or developmental control. Examples of environmental conditions that may effect transcription by inducible promoters include anaerobic conditions, elevated temperature, the presence of light, or spraying with chemicals/hormones.

Suitable constitutive promoters for use in a plant host cell include, for example, the core promoter of the Rsyn7 promoter and other related constitutive promoters (International Publication No. WO 99/43838 and U.S. Pat. No. 6,072,050); the core CaMV 35S promoter (Odell et al., 1985, *Nature* 313:810-812); rice actin (McElroy et al., 1990, *Plant Cell* 2:163-171); ubiquitin (Christensen et al., 1989, *Plant Mol. Biol.* 12:619-632 and Christensen et al., 1992, *Plant Mol. Biol.* 18:675-689); pEMU (Last et al., 1991, *Theor. Appl. Genet.* 81:581-588); MAS (Velten et al., 1984, *EMBO J.* 3:2723-2730); ALS promoter (U.S. Pat. No. 5,659,026), and the like (e.g., U.S. Pat. Nos. 5,608,149; 5,608,144; 5,604,121; 5,569,597; 5,466,785; 5,399,680; 5,268,463; 5,608,142; and 6,177,611).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Accordingly, the present invention provides a host cell having an expression vector comprising a nucleic acid of the invention, or a variant thereof. A host cell can be any prokaryotic (e.g., *E. coli, Bacillus thuringiensis* or other *Bacillus* spp.) or eukaryotic cell (e.g., insect cells, yeast or plant cells). The invention also provides a method for expressing a nucleic acid of the invention thus making the encoded polypeptide comprising the steps of i) culturing a cell comprising a nucleic acid molecule of the invention under conditions that allow production of the encoded polypeptide; and ii) isolating the expressed polypeptide.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid molecules into a host cell, including calcium phosphate or calcium chloride co-precipitation, DEAE-dextran-mediated transfection, lipofection, or electroporation. Suitable methods for transforming or transfecting host cells can be found in the art (e.g., Sambrook, et al. supra.).

Additionally, it is possible to target expression of the particular DNA into a particular location in a plant. For example, the genes in plants encoding the small subunit of RUBISCO (SSU) are often highly expressed, light regulated and sometimes show tissue specificity. These expression properties are largely due to the promoter sequences of these genes. It has been possible to use SSU promoters to express heterologous genes in transformed plants. Typically a plant will contain multiple SSU genes, and the expression levels and tissue specificity of different SSU genes will be different. The SSU proteins are encoded in the nucleus and synthesized in the cytoplasm as precursors that contain an N-terminal extension known as the chloroplast transit peptide (CTP). The CTP directs the precursor to the chloroplast and promotes the uptake of the SSU protein into the chloroplast. In this process, the CTP is cleaved from the SSU protein. These CTP sequences have been used to direct heterologous proteins into chloroplasts of transformed plants.

The SSU promoters might have several advantages for expression of heterologous genes in plants. Some SSU promoters are very highly expressed and could give rise to expression levels as high as or higher than those observed with other promoters. Because of the differing the tissue distribution of expression from SSU promoters, for control of some insect pests, it may be advantageous to direct the expression of crystal proteins to those cells in which SSU is most highly expressed.

For example, although relatively constitutive, in the leaf the CaMV35S promoter is more highly expressed in vascular tissue than in some other parts of the leaf, while most SSU promoters are most highly expressed in the mesophyll cells of the leaf. Some SSU promoters also are more highly tissue specific, so it could be possible to utilize a specific SSU promoter to express the protein of the present invention in only a subset of plant tissues, if for example expression of such a protein in certain cells was found to be deleterious to those cells. For example, for control of Colorado potato beetle in potato, it may be advantageous to use SSU promoters to direct crystal protein expression to the leaves but not to the edible tubers.

Utilizing SSU CTP sequences to localize crystal proteins to the chloroplast might also be advantageous. Localization of the *B. thuringiensis* crystal proteins to the chloroplast could protect these from proteases found in the cytoplasm. This could stabilize the proteins and lead to higher levels of accumulation of active toxin.cry genes containing the CTP may be used in combination with the SSU promoter or with other promoters such as CaMV35S.

It may also be advantageous for some purposes to direct the Cry proteins to other compartments of the plant cell, as such may result in reduced exposure of the proteins to cytoplasmic proteases, in turn leading to greater accumulation of the protein, which could yield enhanced insecticidal activity. Extracellular localization could lead to increased exposure of certain insects to the Cry proteins, which could also lead to enhanced insecticidal activity. If a particular Cry protein was found to harm plant cell function, then localization to a noncytoplasmic compartment could protect these cells from the protein.

By way of example, in plants as well as other eukaryotes, proteins that are to be localized either extracellularly or in several specific compartments are typically synthesized with an N-terminal amino acid extension known as the signal peptide. This signal peptide directs the protein to enter the compartmentalization pathway, and it is typically cleaved from the mature protein as an early step in compartmentalization. For an extracellular protein, the secretory pathway typically involves cotranslational insertion into the endoplasmic reticulum with cleavage of the signal peptide occurring at this stage. The mature protein then passes through the Golgi body into vesicles that fuse with the plasma membrane thus releasing the protein into the extracellular space. Proteins destined for other compartments follow a similar pathway. For example, proteins that are destined for the endoplasmic reticulum or the Golgi body follow this scheme, but they are specifically retained in the appropriate compartment. In plants, some proteins are also targeted to the vacuole, another membrane bound compartment in the cytoplasm of many plant cells. Vacuole targeted proteins diverge from the above pathway at the Golgi body where they enter vesicles that fuse with the vacuole.

A common feature of this protein targeting is the signal peptide that initiates the compartmentalization process. Fusing a signal peptide to a protein will in many cases lead to the targeting of that protein to the endoplasmic reticulum. The efficiency of this step may depend on the sequence of the mature protein itself as well. The signals that direct a protein to a specific compartment rather than to the extracellular space are not as clearly defined. It appears that many of the signals that direct the protein to specific compartments are contained within the amino acid sequence of the mature protein. This has been shown for some vacuole targeted proteins, but it is not yet possible to define these sequences precisely. It appears that secretion into the extracellular space is the "default" pathway for a protein that contains a signal sequence but no other compartmentalization signals. Thus, a strategy to direct Cry proteins out of the cytoplasm is to fuse the genes for synthetic Cry proteins to DNA sequences encoding known plant signal peptides. These fusion genes will give rise to cry proteins that enter the secretory pathway, and lead to extracellular secretion or targeting to the vacuole or other compartments.

Signal sequences for several plant genes have been described. One such sequence is for the tobacco pathogenesis related protein PR1b has been previously described (Cornelissen et al., 1986). The PR1b protein is normally localized to the extracellular space. Another type of signal peptide is contained on seed storage proteins of legumes. These proteins are localized to the protein body of seeds, which is a vacuole like compartment found in seeds. A signal peptide DNA sequence for the .beta.-subunit of the 7S storage protein of common bean (*Phaseolus vulgaris*), PvuB has been described (Doyle et al., 1986). Based on the published these published sequences, genes may be synthesized chemically using oligonucleotides that encode the signal peptides for PR1b and PvuB. In some cases to achieve secretion or compartmentalization of heterologous proteins, it may be necessary to include some amino acid sequence beyond the normal cleavage site of the signal peptide. This may be necessary to insure proper cleavage of the signal peptide.

Production of Transgenic Plants

Any method known in the art can be used for transforming a plant or plant cell with a nucleic acid molecule of the present invention. Nucleic acid molecules can be incorporated into plant DNA (e.g., genomic DNA or chloroplast DNA) or be maintained without insertion into the plant DNA (e.g., through the use of artificial chromosomes). Suitable methods of introducing nucleic acid molecules into plant cells include microinjection (Crossway et al., 1986, Biotechniques 4:320-334); electroporation (Riggs et al., 1986, *Proc. Natl. Acad. Sci.* 83:5602-5606; D'Halluin et al., 1992, *Plant Cell* 4:1495-1505); *Agrobacterium*-mediated transformation (U.S. Pat. Nos. 5,563,055 and 5,981,840, Osjoda et al., 1996, *Nature Biotechnology* 14:745-750; Horsch et al., 1984, *Science* 233: 496-498, Fraley et al., 1983, *Proc. Natl. Acad. Sci.* 80:4803, and *Gene Transfer to Plants*, Potrykus, ed., Springer-Verlag, Berlin 1995); direct gene transfer (Paszkowski et al., 1984, *EMBO J.* 3:2717-2722); ballistic particle acceleration (U.S. Pat. Nos. 4,945,050; 5,879,918; 5,886,244; 5,932,782; Tomes et al., 1995, "Direct DNA Transfer into Intact Plant Cells via Microprojectile Bombardment, in *Plant Cell, Tissue, and Organ Culture: Fundamental Methods*, ed. Gamborg and Phillips, Springer-Verlag, Berlin; and McCabe et al., 1988, *Biotechnology* 6:923-926); virus-mediated transformation (U.S. Pat. Nos. 5,889,191, 5,889,190, 5,866,785, 5,589,367 and 5,316,931); pollen transformation (De Wet et al., 1985, in *The Experimental Manipulation of Ovule Tissues*, ed. Chapman et al., Longman, N.Y., pp. 197-209); Lec 1 transformation (U.S. patent application Ser. No. 09/435,054; International Publication No. WO 00/28058); whisker-mediated transformation (Kaeppler et al., 1990, *Plant Cell Reports* 9:415-418; Kaeppler et al., 1992, *Theor. Appl. Genet.* 84:560-566); and chloroplast transformation technology (Bogorad, 2000, *Trends in Biotechnology* 18: 257-263; Ramesh et al., 2004, *Methods Mol. Biol.* 274:301-7; Hou et al., 2003, *Transgenic Res.* 12:111-4; Kindle et al., 1991, *Proc. Natl. Acad. Sci.* 88:1721-5; Bateman and Purton, 2000, *Mol Gen Genet.* 263:404-10; Sidorov et al., 1999, *Plant J.* 19:209-216).

The choice of transformation protocols used for generating transgenic plants and plant cells can vary depending on the type of plant or plant cell, i.e., monocot or dicot, targeted for transformation. Examples of transformation protocols particularly suited for a particular plant type include those for: potato (Tu et al., 1998, *Plant Molecular Biology* 37:829-838; Chong et al., 2000, *Transgenic Research* 9:71-78); soybean (Christou et al., 1988, *Plant Physiol.* 87:671-674; McCabe et al., 1988, *BioTechnology* 6:923-926; Finer and McMullen, 1991, *In Vitro Cell Dev. Biol.* 27P:175-182; Singh et al., 1998, *Theor. Appl. Genet.* 96:319-324); maize (Klein et al., 1988, *Proc. Natl. Acad. Sci.* 85:4305-4309; Klein et al., 1988, *Biotechnology* 6:559-563; Klein et al., 1988, *Plant Physiol.* 91:440-444; Fromm et al., 1990, *Biotechnology* 8:833-839; Tomes et al., 1995, "Direct DNA Transfer into Intact Plant Cells via Microprojectile Bombardment," in *Plant Cell, Tissue, and Organ Culture: Fundamental Methods*, ed. Gamborg (Springer-Verlag, Berlin)); cereals (Hooykaas-Van Slogteren et al., 1984, *Nature* 311:763-764; U.S. Pat. No. 5,736,369).

In some embodiments, more than one construct is used for transformation in the generation of transgenic plants and plant cells. Multiple constructs may be included in cis or trans positions. In preferred embodiments, each construct has a promoter and other regulatory sequences.

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in the art (e.g., Evans et al., *Protoplasts Isolation and Culture, Handbook of Plant Cell Culture*, pp. 124-176, MacMillilan Publishing Company, New York, 1983; and Binding, Regeneration of Plants, Plant Protoplasts, pp. 21-73, CRC Press, Boca Raton, 1985). Regeneration can also be oBtained from plant callus, explants, organs, or parts thereof. Such regeneration techniques are also described in the art (e.g., Klee et al. 1987, Ann. Rev. of Plant Phys. 38:467-486).

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in methods of the present invention includes the class of higher and lower plants amenable to transformation techniques, including angiosperms (monocotyledonous and dicotyledonous plants), gymnosperms, ferns, and multicellular algae. Plants of a variety of ploidy levels, including aneuploid, polyploid, diploid, haploid and hemizygous plants are also included.

The nucleic acid molecules of the invention can be used to confer desired traits on essentially any plant. Thus, the invention has use over a broad range of plants, including species from the genera *Agrotis, Allium, Ananas, Anacardium, Apium, Arachis, Asparagus, Athamantha, Atropa, Avena, Bambusa, Beta, Brassica, Bromus, Browaalia, Camellia, Cannabis, Carica, Ceratonia. Cicer, Chenopodium, Chicorium, Citrus, Citrullus, Capsicum, Carthamus, Cocos, Coffea, Coix, Cucumis, Cucurbita, Cynodon, Dactylis, Datura, Daucus, Dianthus, Digitalis, Dioscorea, Elaeis, Eliusine, Euphorbia, Festuca, Ficus, Fragaria, Geranium, Glycine, Graminae, Gossypium, Helianthus, Heterocallis, Hevea, Hibiscus, Hordeum, Hyoscyamus, Ipomoea, Lactuca, Lathyrus, Lens, Lilium, Linum, Lolium, Lotus, Lupinus, Lycopersicon, Macadamia, Macrophylla, Malus, Mangifera, Manihot, Majorana, Medicago, Musa, Narcissus, Nemesia, Nicotiana, Onobrychis, Olea, Olyreae, Oryza, Panicum, Panicum, Panieum, Pannisetum, Pennisetum, Petunia, Pelar-*

*gonium, Persea, Pharoideae, Phaseolus, Phleum, Picea, Poa, Pinus, Pistachia, Pisum, Populus, Pseudotsuga, Pyrus, Prunus, Pseutotsuga, Psidium, Quercus, Ranunculus, Raphanus, Ribes, Ricinus, Rhododendron, Rosa, Saccharum, Salpiglossis, Secale, Senecio, Setaria, Sequoia, Sinapis, Solanum, Sorghum, Stenotaphrum, Theobromus, Trigonella, Trifolium, Trigonella, Triticum, Tsuga, Tulipa, Vicia, Vitis, Vigna*, and *Zea*.

In specific embodiments, transgenic plants are maize, potato, rice, soybean, alfalfa, sunflower, canola, or cotton plants.

Transgenic plants may be grown and pollinated with either the same transformed strain or different strains. Two or more generations of the plants may be grown to ensure that expression of the desired nucleic acid molecule, polypeptide and/or phenotypic characteristic is stably maintained and inherited. One of ordinary skill in the art will recognize that after the nucleic acid molecule of the present invention is stably incorporated in transgenic plants and confirmed to be operable, it can be introduced into other plants by sexual crossing. Any of a number of standard breeding techniques can be used, depending upon the species to be crossed.

In certain embodiments the polynucleotides of the embodiments can be stacked with any combination of polynucleotide sequences of interest in order to create plants with a desired trait. For example, the polynucleotides of the embodiments may be stacked with any other polynucleotides encoding polypeptides having pesticidal and/or insecticidal activity, such as other Bt toxic proteins (described in, for example, U.S. Pat. Nos. 5,366,892; 5,747,450; 5,737,514; 5,723,756; 5,593,881; and Geiser et al. (1986) Gene 48:109), lectins (Van Damme et al. (1994) Plant Mol. Biol. 24:825, pentin (described in U.S. Pat. No. 5,981,722), and the like. The combinations generated can also include multiple copies of any one of the polynucleotides of interest. The polynucleotides of the embodiments can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) Eur. J. Biochem. 165:99-106; and WO 98/20122) and high methionine proteins (Pedersen et al. (1986) J. Biol. Chem. 261:6279; Kirihara et al. (1988) Gene 71:359; and Musumura et al. (1989) Plant Mol. Biol. 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the embodiments can also be stacked with traits desirable for disease or herbicide resistance (e.g., fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; genes encoding resistance to inhibitors of glutamine synthase such as phosphinothricin or basta (e.g., bar or PAT genes); and glyphosate resistance (EPSPS and GAT (glyphosate acetyl transferase) genes (Castle et al. (2004) Science 304:1151)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference. One could also combine the polynucleotides of the embodiments with polynucleotides providing agronomic traits such as male sterility (see, e.g., U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, e.g., WO 99/25821, WO 99/25854, WO 99/25840, WO 99/25855, and WO 99/25853, all of which are herein incorporated by reference.

Determination of Expression in Transgenic Plants

Any method known in the art can be used for determining the level of expression in a plant of a nucleic acid molecule of the invention or polypeptide encoded therefrom. For example, the expression level in a plant of a polypeptide encoded by a nucleic acid molecule of the invention can be determined by immunoassay, quantitative gel electrophoresis, etc. Expression of nucleic acid molecules of the invention can be measured directly by reverse transcription quantitative PCR (qRT-PCR) of isolated RNA form the plant. Additionally, the expression level in a plant of a polypeptide encoded by a nucleic acid molecule of the invention can be determined by the degree to which the plant phenotype is altered. In a specific embodiment, enhanced insect resistance is the phenotype to be assayed.

As used herein, "enhanced insect resistance" refers to increased resistance of a transgenic plant expressing a polypeptide of the invention to consumption and/or infestation by an insect pest as compared to a plant not expressing a polypeptide of the invention. Enhanced resistance can be measured in a number of ways. In one embodiment, enhanced resistance is measured by decreased damage to a plant expressing a polypeptide of the invention as compared to a plant not expressing a polypeptide of the invention after the same period of insect incubation. Insect damage can be assessed visually. For example in cotton plants, damage after infestation can be measured by looking directly at cotton plant bolls for signs of consumption by insects. In another embodiment, enhanced resistance is measured by increased crop yield from a plant expressing a polypeptide of the invention as compared to a plant not expressing a polypeptide of the invention after the same period of insect incubation. In particular embodiments, the insect pests are from the order of Lepidopteran insects including *Heliothine, Agrotis, Pseudoplusia, Chilo, Spodoptera* spp and others.

Determinations can be made using whole plants, tissues thereof, or plant cell culture.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, and/or defined in the appended claims, be interpreted as descriptive and illustrative of the present invention. Modifications and variations of the present invention are possible in light of the above teachings.

EXAMPLES

Example 1

Single Gene Shuffling

Cry1Ac toxin is currently the most potent toxin known for control of *Heliothis* insects in cotton. However, Cry1Ac has very little activity on secondary pests of the *Spodoptera* class. Cry1Ab toxin is an excellent starting activity for cotton insect pest control since it has slightly less activity on *H. zea* than Cry1Ac but far superior *S. exigua* activity. To meet this product deficiency, a Cry1Ab-like gene was shuffled to obtain Cry 1-derived polypeptides that have improved Heliothine activity while retaining essentially full *Spodoptera* potency. One method used to generate Cry1-derived polypeptides was ‘single gene shuffling’ (mutagenesis combined with shuffling), Shuffling of Cry1Ab was done as follows. Two overlapping fragments of a 5' portion of the Cry1Ab gene from the translation start to the kpnI site were amplified by two separate PCR reactions from a *Bt kurstaki* strain that contains a Cry1Abl gene. These fragments were further fragmented by endonuclease and assembled under certain mutational conditions to create a series or library of shuffled genes. This shuffled portion contains the region coding for the mature toxin. In order to clone and express the shuffled gene library, we constructed an *E. coli*-Bt shuttle vector that contains a tetracycline-resistant gene and two replicons for both hosts. The vector also contains the remaining (not shuffled) 3' portion of the cry1Ca gene from the KpnI site to the translation end along with the cry1Ca transcription promoter and cry1Ac terminator. When the shuffled gene library was cloned in this vector, the full-length 135-kDa proteins were produced. The shuffled gene library was expressed in a cry-minus Bt host called BtG8, which was derived from the HD1 strain by plasmid curing. A selection was made to assure a high transformation competency by electroporation which is required for making a diversified shuffled library. The selected host, BtG8, showed a level of competency over $10^6$ transformants per 1 ug DNA. A shuffled gene library was made by sequentially transforming *E. coli* XL-1 Blue, *E. coli* GM2163 and BtG8. XL-1 Blue was used for the high transformation efficiency. The plasmid was prepared from transformed XL-1 Blue cells, and a small portion was examined by gel electrophoresis to ensure no visible amount of vector molecules without the shuffled DNA. GM2163 was used to prepare unmethylated DNA for electroporation transformation of BtG8. The transformed BtG8 that grew on tetracycline plates were picked onto 96-well plates by robot. These plates were incubated until sporulation and cultures used as seeds for assay sample production. We used two-tier insect screening to obtain high throughput. The first tier was to eliminate variants without any detectable activity. The first tier assay samples were produced in CYS liquid medium as described in a publication by Yamamoto (Identification of entomocidal toxins of *Bacillus thuringiensis* by high-performance liquid chromatography. in Analytical chemistry of *Bacillus thuringiensis*. ed. Hickle, L. A. and Fitch, W. L., American Chemical Society, Washington D.C., USA, 46-60, 1990) in shallow, 96-well plates. At this stage, culture broth containing crystals and spores was assayed with neonate *H. zea* larvae in 96-well plates containing an artificial insect diet. Those variants showing the activity were selected for the next step. For the second tier screening, the crystal proteins were purified from 1 ml culture broth produced in deep 96-well plates by differential solubilization between pH 10.5 and pH 4.4. The crystals were solubilized at pH 10.5 with 2% 2-mercaptoethanol, and the solubilized crystal proteins were precipitated at pH 4.4. After protein concentrations were determined, serial dilutions were made and assayed against *H. zea* larvae using the insect diet incorporation assay. After screening several thousand variants, we found a substantial number of proteins showing improved *H. zea* activity over the parent Cry1Ab. These improved variants were then tested against *Spodoptera exigua*.

Figure 1:
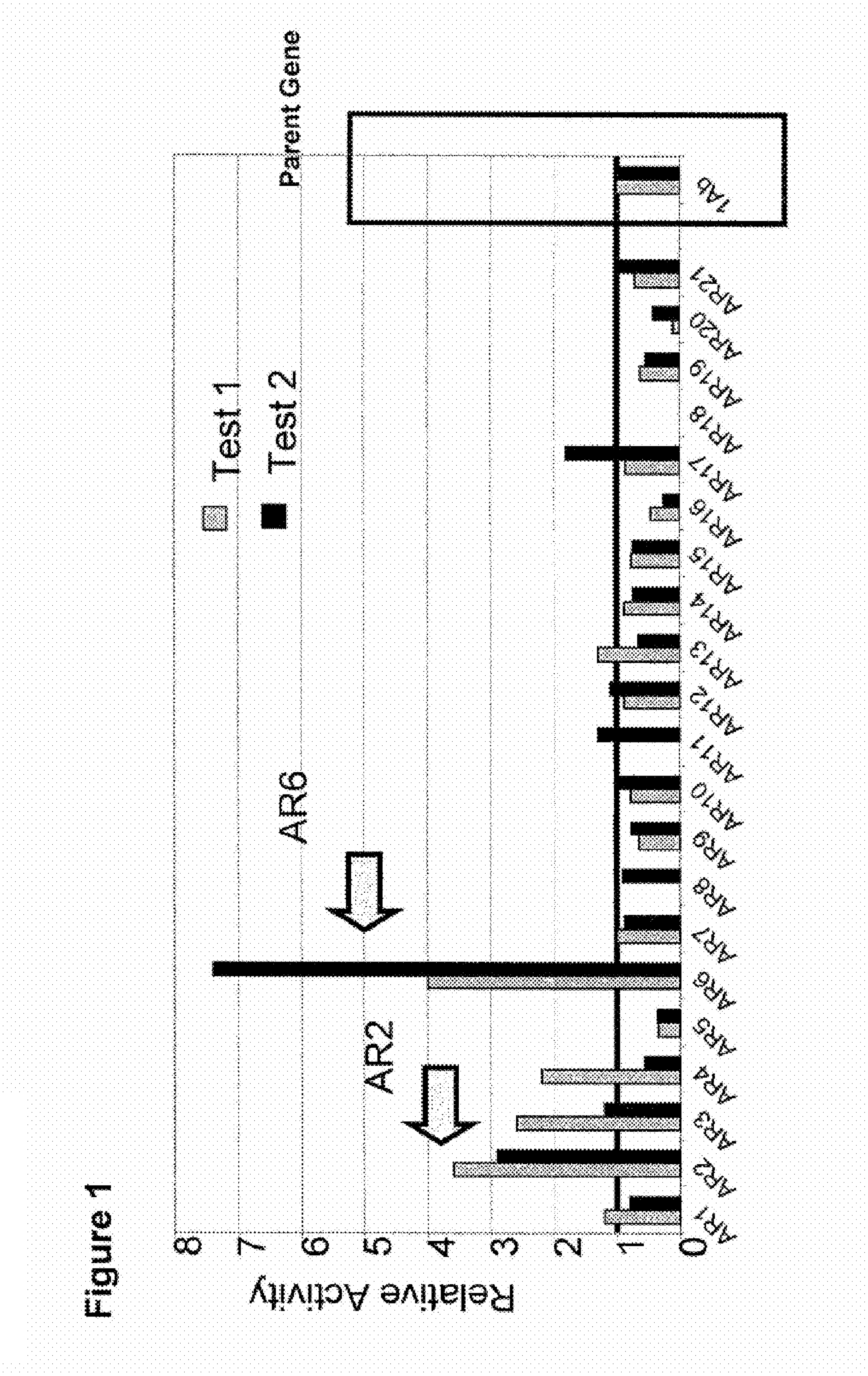
FIG. 1 shows insecticidal activity of variants isolated from single gene shuffling of Cry1Ab against *Helicorverpa zea*.

Polypeptides that resulted from the single gene shuffling were screened for increased *H. zea* activity relative to wild type Cry1Ab. AR2 (SEQ ID NOS:1 and 2) and AR6 (SEQ ID NOS:3 and 4) were identified as Cry1-derived polypeptides that showed improved activity against *H. zea* (FIG. 1). Activity of AR6 was further investigated by comparing relative inverse $EC_{50}$ values for protoxins of AR6, Cry1Ab, Cry1Ac, and Cry1Ca on *Heliothis virescens, Helicoverpa zea*, and *Spodoptera exigua* (FIG. 2). Purified Cry1Ab, AR6, Cry1Ac, and Cry1Ca protoxins were introduced into the artificial diet at six doses and in 24 replicates to determine the $EC_{50}$ of each protoxin against the three insects. The experiment was repeated three times and $EC_{50}$ values were expressed as an average of the three trials. The $EC_{50}$ values were then converted to relative inverse values. Since Cry1Ac had the lowest $EC_{50}$ (highest specific activity) on *Heliothis virescens* and *Helicoverpa zea* it was given a value of 1.0 for each of those respective insect pests. Other protoxin samples had higher $EC_{50}$ values for both *H. virescens* and *H. zea* (lower specific activity) and were converted to values relative to that of Cry1Ac. Likewise Cry1Ca had the lowest $EC_{50}$ value for *Spodoptera exigua* and so was given a relative value of ‘1.0’ on that pest. $EC_{50}$ values of other protoxins were higher (lower specific activity) and were assigned a lower relative value for this pest. These data showed that AR6 has nearly twice the specific activity as wild type Cry1Ab for both *H. zea* and *S. exigua* (FIG. 2). A description of the amino acid sequence differences between the parent toxin Cry1Ab and the shuffled clones is described in Table 3.

An additional single gene shuffling experiment was carried out to improve the *Spodoptera* activity of Cry1Ca. As was done for shuffling the cry1Ab gene, a cry1Ca DNA template was subjected to mutagenesis and DNA shuffling. Protein produced from the shuffled variants was screened for improved *S. exigua* activity. One of the variants, CR62 (SEQ ID NOS: 7 and 8), was found to have a ~3-fold improved $EC_{50}$ compared to the wild type Cry1Ca protein (FIG. 3).

Example 2

Construction of Synthetic CR62 Gene

The DNA sequences of CR62 and the parental gene, Cry1Ca, were modified using random codon usage to create fully synthetic plant expressible genes (SEQ ID NO: 9 and SEQ ID NO:31, respectively. Table 4 provides a description of the encoded amino acid sequence differences between these genes. Following construction of synthetic CR62 and Cry1Ca genes, the coding regions were cloned into binary vector behind a strong constitutive plant viral promoter and the subsequent plasmids transformed into *Agrobacterium tumefaciens* C58. These strains were tested for efficacy in planta using an *Agrobacterium* leaf infiltration based transient expression system followed by leaf disk bioassays with *Spodoptera exigua*. Using this assay it was shown that both genes expressed insecticidal activity although the shuffled CR62 gene performed better than the non-shuffled wild type parent (data not shown).

Example 3

Construction of Synthetic MR8' and AR6 Genes

The DNA sequence of AR6 was targeted for modification to create a synthetic version of the AR6 coding region (SEQ ID NOS: 5 and 6) as described for CR62 in section 6.2. However, in this instance only the 5' end of AR6 encoding the N-terminal protoxin and toxin domains were targeted for re-synthesis. This N-terminal encoding region was spliced to the already existing synthetic C-terminal protoxin encoding region from the synthetic CR62 gene to form a complete protoxin gene for plant expression. In the process of producing a synthetic AR6 gene a precursor gene was constructed. This gene, termed MR8' (SEQ ID NO:11), encodes eight amino acid residue differences from that of AR6 (SEQ ID NO:6) in the toxin portion and four amino acid differences in the protoxin portion of the protein (Table 3).

Example 4

In Planta Testing of the Synthetic AR6 Gene

Following construction of synthetic MR8' and AR6 genes, the coding regions were cloned into a binary vector with a strong constitutive plant viral promoter and the subsequent plasmids transformed into *Agrobacterium tumefaciens* C58. These strains were tested for efficacy in planta using an *Agrobacterium* leaf infiltration based transient expression system followed by leaf disk insect bioassays. Both synthetic AR6 and MR8' were expressed in the transient leaf assay as shown by Western Blot analysis (FIG. 4).

To test for in planta activity, a leaf disk expressing a polypeptide of interest was provided to a pest. Following a 24-hour incubation period, the feeding activity of the pest on the leaf disk was determined by visual observation. Positive controls for *H. zea* activity and *S. exigua* activity were genes encoding Cry2Ab-like (*) polypeptide and CR62, respectively. The results showed that both synthetic AR6 and MR8' confer high-level resistance to both *H. zea* (FIG. 5A) and *S. exigua* (FIG. 5B). Leaf disks infiltrated with *Agrobacterium* lacking a Cry gene were completely consumed by the insect larvae during the assay period (not shown).

Example 5

Further Shuffling Using MR8' as Parent

To further improve the activity of MR8', a second round of DNA shuffling was performed using MR8' as the parent clone. Shuffling was performed on a fragmented MR8' DNA template by directing added sequence diversity with oligonucleotides. As the MR8' gene encodes a protoxin, shuffling was limited to the active toxin region that is responsible for the insecticidal properties. Two kinds of sequence diversity were used to incorporate into the shuffling reactions: phylogenetic and computer generated random diversity. Phylogenetic diversity originated from aligning first round hits AR6, MR8', and wild type Cry1Aa, Cry1Ab, Cry1Ac, Cry1Ad, Cry1Ae, and Cry1Ag polypeptides. Random diversity was generated by choosing random amino acid positions and directing either conservative or non-conservative amino acid changes at those positions. Both kinds of diversity were incorporated into the parent MR8' gene and encoded protein on a domain by domain basis. Several libraries were constructed, each focusing on a selected type of diversity and applied to isolated toxin domain regions or the entire toxin region. Following DNA shuffling each PCR amplified library fragment was reintroduced into the remaining MR8' protoxin fragment by PCR stitching. The library of reconstructed protoxins was then cloned into a pUC like vector such that the Cry1-derived polypeptides were expressed in *E. coli* from the LacZ promoter.

In order to assess the activity of the Cry1-derived polypeptides against *H. zea*, high throughput screening using an artificial diet containing whole *E. coli* cells expressing each of the Cry1-derived polypeptides in an array format was performed (data not shown). Those variants having a high level of activity were then tested for in planta activity. The amino acid diversity present in the variants tested is shown in Table 5. The amino acid sequences of the shuffled toxin regions as well as nucleotide sequences encoding each protoxin are provided by SEQ ID NOS: 11-28.

To initiate the in planta assays, all highly active Cry1-derived variants were cloned into an *Agrobacterium tumefaciens* based plant expression vector. The binary plasmids were then transformed into a host *Agrobacterium*. The Cry1-derived polypeptides were then screened by co-cultivating each in four replicates with *N. benthamiana* leaves (using forced infiltration of each respective culture). Leaf disks were excised from the infiltrated leaf areas and infested with individual $3^{rd}$ instar *H. zea* or $4^{th}$ instar *S. exigua* larvae. After 24 hours feeding activity was determined by video capture of the remaining leaf area expressed in pixels.

FIG. 6 shows the activity of the indicated Cry1-derived polypeptides on *H. zea*. FIG. 7 shows the activity of the indicated Cry1-derived polypeptides on *S. exigua*. All of the tested Cry-1 derived polypeptides show improved activity against *H. zea* as compared to parent polypeptide MR8' while retaining activity against *S. exigua* that is at least as good as MR8'.

TABLE 1

| Cry1 and Cry 1-derived sequences | | | | | |
|---|---|---|---|---|---|
| Variant name | Full Protoxin Region | Shuffled Region | Mature Toxin Region | Sequence Type | SEQ ID NO |
| AR2 | 1-3543 bp | 1-2175 bp | 85-1857 bp | nucleic acid | 1 |
| AR2 | 1-1181 aa | 1-725 aa | 29-619 aa | polypeptide | 2 |
| AR6 | 1-3543 bp | 1-2175 bp | 85-1857 bp | nucleic acid | 3 |
| AR6 | 1-1181 aa | 1-725 aa | 29-619 | polypeptide | 4 |
| Synthetic AR6 | 1-3546 bp | 1-2178 bp | 88-1860 bp | nucleic acid | 5 |
| Synthetic AR6 | 1-1182 aa | 1-726 aa | 30-620 aa | polypeptide | 6 |
| CR62 | 1-3567 bp | 1-2199 bp | 82-1890 bp | nucleic acid | 7 |
| CR62 | 1-1189 aa | 1-733 aa | 28-630 aa | polypeptide | 8 |
| Synthetic CR62 | 1-3567 bp | 1-2199 bp | 82-1890 bp | nucleic acid | 9 |
| Synthetic CR62 | 1-1189 aa | 1-733 aa | 28-630 aa | polypeptide | 10 |
| MR8' | 1-3546 bp | 88-1860 bp | 88-1860 bp | nucleic acid | 11 |
| MR8' | 1-1182 aa | 30-620 aa | 30-620 aa | polypeptide | 12 |
| Variant 41 | 1-3546 bp | 88-1860 bp | 88-1860 bp | nucleic acid | 13 |
| Variant 41 | 1-1182 aa | 30-620 aa | 30-620 aa | polypeptide | 14 |
| Variant 75 | 1-3546 bp | 88-1860 bp | 88-1860 bp | nucleic acid | 15 |
| Variant 75 | 1-1182 aa | 30-620 aa | 30-620 aa | polypeptide | 16 |
| Variant 80 | 1-3546 bp | 88-1860 bp | 88-1860 bp | nucleic acid | 17 |
| Variant 80 | 1-1182 aa | 30-620 aa | 30-620 aa | polypeptide | 18 |
| Variant 85 | 1-3546 bp | 88-1860 bp | 88-1860 bp | nucleic acid | 19 |
| Variant 85 | 1-1182 aa | 30-620 aa | 30-620 aa | polypeptide | 20 |
| Variant 88 | 1-3546 bp | 88-1860 bp | 88-1860 bp | nucleic acid | 21 |
| Variant 88 | 1-1182 aa | 30-620 aa | 30-620 aa | polypeptide | 22 |
| Variant 90 | 1-3546 bp | 88-1860 bp | 88-1860 bp | nucleic acid | 23 |
| Variant 90 | 1-1182 aa | 30-620 aa | 30-620 aa | polypeptide | 24 |
| Variant 5-40 | 1-3546 bp | 88-1860 bp | 88-1860 bp | nucleic acid | 25 |
| Variant 5-40 | 1-1182 aa | 30-620 aa | 30-620 aa | polypeptide | 26 |
| Variant 5-44 | 1-3546 bp | 88-1860 bp | 88-1860 bp | nucleic acid | 27 |
| Variant 5-44 | 1-1182 aa | 30-620 aa | 30-620 aa | polypeptide | 28 |
| Cry1Ca reference | | — | | nucleic acid | 29 |
| Cry1Ca reference | | — | | polypeptide | 30 |
| Synthetic Cry1Ca | 1-3567 bp | — | 82-1890 bp | nucleic acid | 31 |
| Synthetic Cry1Ca | 1-1189 aa | — | 28-630 aa | polypeptide | 32 |
| Cry1Ab reference | | — | 85-1866 bp | nucleic acid | 33 |
| Cry1Ab reference | 1-1155 aa | — | 29-622 aa | polypeptide | 34 |
| Cry2Ab-like (*) reference | 1-633 aa | — | | polypeptide | 35 |
| Cry1Ac reference | 1-1178 aa | — | 29-623 | polypeptide | 36 |

Sources for all reference genes and proteins: http://www.lifesci.sussex.ac.uk/home/Neil_Crickmore/Bt/index.html Revision of the Nomenclature for the *Bacillus thuringiensis* Pesticidal Crystal Proteins N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813

TABLE 2

| Codon Table | | | |
|---|---|---|---|
| Amino acids | | | Codon |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |

TABLE 2-continued

| Codon Table | | | |
|---|---|---|---|
| Amino acids | | | Codon |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

TABLE 3

Comparison of amino acid sequence differences between Cry1Ab and 1st round shuffled hits

| | Amino acid sequence position | | | | | | | | | | | | | | | |
|---|---|---|---|---|---|---|---|---|---|---|---|---|---|---|---|---|
| SequenceName | 1 | 2 | 3 | 8 | 90 | 101 | 128 | 133 | 212 | 261 | 268 | 271 | 419 | 466 | 468 | 469 |
| Cry1Ab (SEQ ID NO: 33) | M | | D | I | E | L | R | I | Y | V | I | N | N | I | P | S |
| AR2 (SEQ ID NO: 1) | — | Gap | H | T | G | — | — | — | — | — | V | D | — | T | D | P |
| AR6 (SEQ ID NO: 3) | — | | H | T | — | — | — | — | — | — | V | D | D | T | D | P |
| Synthetic AR6 (SEQ ID NO: 5) | — | G | H | T | — | — | — | — | — | — | V | D | D | T | D | P |
| MR8′ (SEQ ID NO: 11) | — | G | H | — | — | V | K | T | H | A | — | — | — | T | D | P |

| | Amino acid sequence position | | | | | | | | | | | | | | |
|---|---|---|---|---|---|---|---|---|---|---|---|---|---|---|---|
| SequenceName | 470 | 471 | 473 | 598 | 624 | 626 | 627 | 629 | 654 | 666 | 671 | 679 | 691 | 697 | 724 |
| Cry1Ab (SEQ ID NO: 33) | S | Q | T | V | A | N | E | F | E | K | K | S | R | L | L |
| AR2 (SEQ ID NO: 1) | E | R | N | F | — | S | — | L | — | — | E | — | — | — | — |
| AR6 (SEQ ID NO: 3) | E | R | N | — | — | S | — | — | — | — | — | — | G | — | — |
| Synthetic AR6 (SEQ ID NO: 5) | E | R | N | — | — | S | — | — | D | R | — | — | — | P | P |
| MR8′ (SEQ ID NO: 11) | E | R | N | — | V | — | A | — | D | R | — | — | — | P | P |

Amino acid alignments derived from translation of listed DNA sequences. A gap at position 2 is inserted into non-synthetically derived amino acid sequences to accommodate insertion of a glycine residue at that position in the synthetically derived polypeptide sequences. Thus, the matching amino acid positions in SEQ IDNOs: 1, 3, and 33 would be one less than each of the above alignment coordinates beyond position 1.

TABLE 4

Comparison of amino acid sequence differences between Cry1Ca and shuffled hit clone CR62

| | Amino Acid Position: | | | | | | | |
|---|---|---|---|---|---|---|---|---|
| SequenceName | 124 | 268 | 294 | 312 | 398 | 453 | 485 | 586 |
| Synthetic Cry1Ca (SEQ ID NO: 31) | E | T | R | D | F | D | I | I |
| Synthetic CR62 (SEQ ID NO: 9) | A | A | A | G | L | H | V | T |
| CR62 (SEQ ID NO: 7) | A | A | A | G | L | H | V | T |

Amino acid alignments derived from translation of listed DNA sequences.

TABLE 5

Comparison of amino acid sequence differences between δ-endotoxin region for Cry1Ab and 2nd round shuffled hits

| SequenceName | Amino Acid position: 35 | 39 | 56 | 57 | 61 | 72 | 81 | 99 | 104 | 133 | 175 | 183 | 188 | 190 | 232 | 239 | 242 | 250 | 251 |
|---|---|---|---|---|---|---|---|---|---|---|---|---|---|---|---|---|---|---|---|
| Cry1Ab (SEQ ID NO: 34) | I | I | I | N | E | L | I | R | I | Y | Y | Y | E | V | V | I | N | G | S |
| MR8' (SEQ ID NO: 12) | - | - | - | - | - | V | - | K | T | - | - | H | - | - | A | - | - | - | - |
| Variant 41 (SEQ ID NO: 14) | - | - | - | S | - | V | - | K | - | - | - | - | - | - | - | V | - | A | - |
| Variant 75 (SEQ ID NO: 16) | V | V | - | - | - | V | - | K | T | - | - | H | G | - | A | - | - | - | - |
| Variant 80 (SEQ ID NO: 18) | V | - | - | - | - | V | - | K | T | - | F | H | - | I | A | - | - | - | - |
| Variant 85 (SEQ ID NO: 20) | - | - | V | - | - | V | V | K | T | - | - | H | - | I | A | - | - | - | - |
| Variant 88 (SEQ ID NO: 22) | V | - | - | - | - | V | - | K | T | - | - | H | - | I | A | - | - | - | - |
| Variant 90 (SEQ ID NO: 24) | - | - | - | - | - | V | - | K | T | F | F | H | - | I | A | - | - | - | - |
| Variant 5-40 (SEQ ID NO: 26) | - | - | - | - | - | V | - | K | T | - | - | H | - | - | A | - | - | - | - |
| Variant 5-44 (SEQ ID NO: 28) | - | - | - | - | - | V | - | K | T | - | - | H | - | - | A | - | - | - | - |

| SequenceName | Amino Acid position: 271 | 373 | 379 | 390 | 408 | 428 | 437 | 439 | 440 | 441 | 442 | 444 | 569 |
|---|---|---|---|---|---|---|---|---|---|---|---|---|---|
| Cry1Ab (SEQ ID NO: 34) | I | Y | V | N | F | I | I | P | S | S | Q | T | V |
| MR8' (SEQ ID NO: 12) | - | - | - | - | - | - | T | D | P | E | R | N | - |
| Variant 41 (SEQ ID NO: 14) | - | - | - | - | - | - | T | D | P | E | R | N | - |
| Variant 75 (SEQ ID NO: 16) | - | - | - | - | - | - | T | D | P | E | R | N | - |
| Variant 80 (SEQ ID NO: 18) | - | - | - | - | - | - | T | D | P | E | R | N | - |
| Variant 85 (SEQ ID NO: 20) | - | - | - | - | - | - | T | D | P | E | R | N | - |

TABLE 5-continued

| Comparison of amino acid sequence differences between δ-endotoxin region for Cry1Ab and 2nd round shuffled hits | | | | | | | | | | | | | |
|---|---|---|---|---|---|---|---|---|---|---|---|---|---|
| Variant 88 (SEQ ID NO: 22) | - | - | - | - | - | - | T | D | P | E | R | N | - |
| Variant 90 (SEQ ID NO: 24) | - | - | - | - | - | - | T | D | P | E | R | N | - |
| Variant 5-40 (SEQ ID NO: 26) | V | - | I | - | - | V | T | D | P | E | R | N | - |
| Variant 5-44 (SEQ ID NO: 28) | - | F | - | - | Y | V | T | D | P | E | R | N | - |

Amino acid positions are relative to +1 being the first residue of the mature toxin.

What is claimed is:

1. An isolated polypeptide comprising a first polypeptide sequence that is at least 99% identical to the polypeptide sequence of any one of SEQ ID NOS: 12, 14, 16, 18, 20, 22, 24, 26, or 28, wherein said polypeptide has insecticidal activity.

2. The polypeptide of claim 1 further comprising additional amino acids, said additional amino acids expressed in conjunction with said first polypeptide to create a protoxin.

3. The polypeptide of claim 2, wherein said additional amino acids are separated from said first polypeptide in an insect.

4. A polypeptide comprising the amino acid sequence of any one of SEQ ID NOS: 12, 14, 16, 18, 20, 22, 24, 26, or 28.

5. The polypeptide of claim 4 further comprising additional amino acids, said additional amino acids expressed in conjunction with said first polypeptide to create a protoxin.

6. The polypeptide of claim 5, wherein said additional amino acids are separated from said first polypeptide in an insect.

* * * * *